United States Patent
Cherney et al.

(10) Patent No.: US 11,337,970 B2
(45) Date of Patent: May 24, 2022

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: Emily Charlotte Cherney, Princeton, NJ (US); Weifang Shan, Princeton, NJ (US); Liping Zhang, Princeton, NJ (US); Susheel Jethanand Nara, Bangalore (IN); Audris Huang, Princeton, NJ (US); James Aaron Balog, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 502 days.

(21) Appl. No.: 16/328,449

(22) PCT Filed: Aug. 25, 2017

(86) PCT No.: PCT/US2017/048533
§ 371 (c)(1),
(2) Date: Feb. 26, 2019

(87) PCT Pub. No.: WO2018/039512
PCT Pub. Date: Mar. 1, 2018

(65) Prior Publication Data
US 2021/0290613 A1 Sep. 23, 2021

Related U.S. Application Data

(60) Provisional application No. 62/380,042, filed on Aug. 26, 2016.

(51) Int. Cl.
*A61K 31/4709* (2006.01)
*A61K 31/4375* (2006.01)
*A61K 31/5025* (2006.01)
*A61K 31/517* (2006.01)
*A61K 39/395* (2006.01)
*C07D 401/08* (2006.01)
*C07D 401/12* (2006.01)
*C07D 413/12* (2006.01)
*C07D 417/12* (2006.01)
*C07D 471/04* (2006.01)
*C07D 487/04* (2006.01)
*C07D 491/056* (2006.01)

(52) U.S. Cl.
CPC ...... *A61K 31/4709* (2013.01); *A61K 31/4375* (2013.01); *A61K 31/5025* (2013.01); *A61K 31/517* (2013.01); *A61K 39/3955* (2013.01); *C07D 401/08* (2013.01); *C07D 401/12* (2013.01); *C07D 413/12* (2013.01); *C07D 417/12* (2013.01); *C07D 471/04* (2013.01); *C07D 487/04* (2013.01); *C07D 491/056* (2013.01)

(58) Field of Classification Search
CPC combination set(s) only.
See application file for complete search history.

(56) References Cited

U.S. PATENT DOCUMENTS

| 6,224,849 B1 * | 5/2001 | Kennis ............... C07D 277/82 424/1.81 |
| 7,754,105 B2 | 7/2010 | Hirao et al. |
| 8,722,720 B2 | 5/2014 | Mautino et al. |
| 2001/0049379 A1 | 12/2001 | Lowe |

FOREIGN PATENT DOCUMENTS

| WO | 99/29310 A2 | 6/1999 |
| WO | 2004/094409 A1 | 11/2004 |
| WO | 2011/070024 A1 | 6/2011 |
| WO | 2011/107553 A1 | 9/2011 |
| WO | 2011/131407 A1 | 10/2011 |
| WO | 2011/140249 A1 | 11/2011 |
| WO | 2013/087699 A1 | 6/2013 |
| WO | 2013/119716 A1 | 8/2013 |
| WO | 2013/132044 A1 | 9/2013 |
| WO | 2013/169264 A1 | 11/2013 |
| WO | 2014/036357 A1 | 3/2014 |
| WO | 2015/031295 A1 | 3/2015 |

OTHER PUBLICATIONS

Jeankumar, V. et al., Eur. J. Med. Chem. 2016, vol. 122, pp. 216-231.*
Vlahos et al., "A specific inhibitor of phosphatidyleinositol 3-kinase, 2-(4-morpholinyl)-8-phenyl-4H-1-benzopyran-4-one (LY294002)", J. Biol. Chem, Feb. 18, 1994, 269(7), 5241-5248.
Serafini et al., "Myeloid suppressor cells in cancer: recruitment, phenotype, properties, and mechanisms of immune suppression", In Seminars in Cancer Biol., Feb. 1, 2006, 16(1), 53-65.
Sekulic et al., "A direct linkage between the phosphoinositide 3-kinase-AKT signaling pathway and the mammalian target of rapamycin in mitogen-stimulated and transformed cells", Cancer Res., Jul. 1, 2000, 60(13), 3504-3513.
Scheller et al., "Paclitaxel Balloon Coating, A Novel Method for Prevention and Therapy of Restenosis", Circulation, Aug. 17, 2004, 110(7), 810-814.
Sausville et al., "Cyclin-dependent kinase modulators studied at the NCI: pre-clinical and clinical studies", Curr. Med. Chem. Anti-Cancer Agents, Jan. 1, 2003, 3(1), 47-56.
Kohl et al., "Inhibition of farnesyltransferase induces regression of mammary and salivary carcinomas in ras transgenic mice", Nat. Med., Aug. 1995, 1(8), 792-797.

(Continued)

*Primary Examiner* — Heidi Reese
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

5 Claims, No Drawings

(56) References Cited

OTHER PUBLICATIONS

Goldstein et al., "Biological efficacy of a chimeric antibody to the epidermal growth factor receptor in human tumor xenograft model", Clin. Cancer Res., Nov. 1, 1995, 1(11): 1311-1318.
Brandacher, et al., Prognostic value of indoleamine 2, 3-dioxygenase expression in colorectal cancer: effect on tower-infiltrating T cells, Clin. Cancer Res., Feb. 15, 2006, 12(4), 1144-1151.
Ball, H.J. et al., Characterization of an indoleamine 2, 3-dioxygenase-like protein found in humans and mice, Gene, Jul. 1, 2007, 396(1), 203-213.

\* cited by examiner

INHIBITORS OF INDOLEAMINE 2,3-DIOXYGENASE AND METHODS OF THEIR USE

CROSS REFERENCE TO RELATED APPLICATIONS

This application is the National Stage Application of International Patent Application No. PCT/US2017/048533 filed Aug. 25, 2017, which claims the benefit of U.S. Provisional Application No. 62/380,042, filed Aug. 26, 2016. Each of these applications is incorporated by reference herein in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO, also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., Gene, 396(1):203-213 (Jul. 1, 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine: p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula I and formula II:

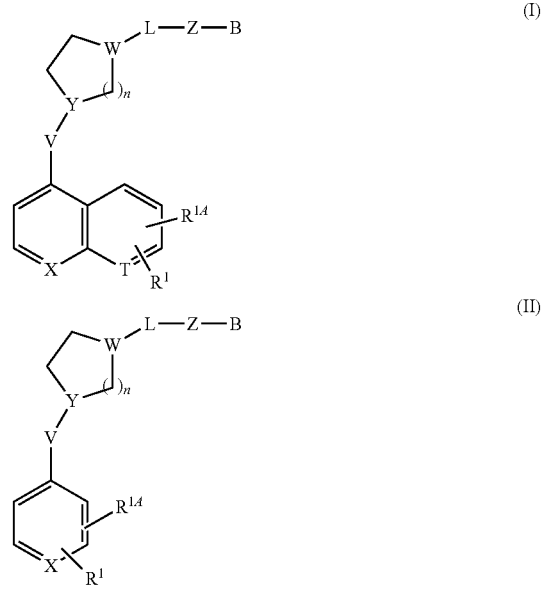

wherein X is CH or N; T is CH or N; V is a bond or O; Y is CH or N; W is —CH—, —C($C_1$-$C_6$alkyl)-, or N, n is 0, 1, 2, 3, or 4; L is a $C_1$-$C_6$alkylene optionally substituted with 1, 2, or 3 substituents independently selected from $C_1$-$C_6$alkyl, $C_1$-$C_6$haloalkyl, $C_1$-$C_6$alkenyl, and —$C_1$-

$C_6$alkO$C_1$-$C_6$alkyl; Z is a bond, —NH—, or —N($C_1$-$C_6$alkyl); B is benzoimidazolyl, imidazopyridinyl, benzothiazolyl, benzooxazolyl, triazolopyridinyl, pyrazolopyridinyl, quinazolinonyl, and imidazopyridazinyl, wherein the heteroaryl is optionally substituted with one, two, three, or four $R^2$ substituents independently selected from halo, $C_1$-$C_6$alkyl, $C_1$-$C_6$haloalkyl, —CN, —O$C_1$-$C_6$alkyl, —O$C_1$-$C_6$haloalkyl, —COOH, —COO$C_1$-$C_6$alkyl, and dioxolanyl; $R^1$ is H, halo, $C_1$-$C_6$alkyl, —O$C_1$-$C_6$alkyl, or $C_1$-$C_6$haloalkyl; and $R^{1A}$ is H, halo, $C_1$-$C_6$alkyl, —O$C_1$-$C_6$alkyl, or $C_1$-$C_6$haloalkyl.

Also within the scope of the invention are pharmaceutically acceptable salts, stereoisomers, tautomers, and solvates of the compounds of formula I and formula II.

The invention is also directed to pharmaceutical compositions comprising one or more compounds of formula I and/or formula II. The invention is also directed to methods of treating cancer using one or more compounds of formula I and/or formula II.

DETAILED DESCRIPTION OF THE
INVENTION COMPOUNDS OF THE
INVENTION

The disclosure is directed to compounds of formula I and formula II:

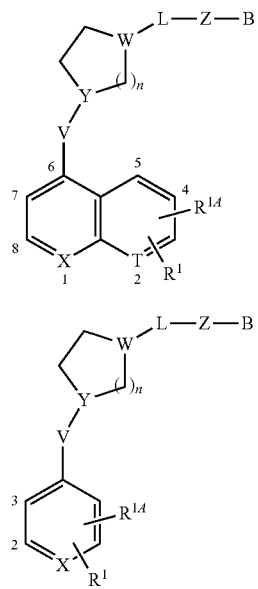

According to the disclosure, X is CH or N. In some embodiments, X is CH. In other embodiments, X is N.

According to the disclosure T is CH or N. In some aspects, T is CH. In other aspects, T is N.

In some embodiments, X is CH and T is CH. In other embodiments, X is N and T is CH. In other embodiments, X is CH and T is N. In other embodiments, X is N and T is N.

According to the disclosure, $R^1$ is H, halo, $C_1$-$C_6$alkyl, —O$C_1$-$C_6$alkyl, or $C_1$-$C_6$haloalkyl. In some aspects, $R^1$ is H. In some aspects, $R^1$ is halo (F, Cl, Br, or I), preferably F. In other aspects, $R^1$ is $C_1$-$C_6$alkyl, for example, methyl, ethyl, isopropyl, butyl, and t-butyl. In some aspects, $R^1$ is —O$C_1$-$C_6$alkyl, for example, methoxy, ethoxy, isopropoxy, butoxy. In yet other aspects. $R^1$ is $C_1$-$C_6$haloalkyl, for example, —$CF_3$. In some aspects, $R^1$ is halo, $C_1$-$C_6$alkyl, or $C_1$-$C_6$haloalkyl. In some aspects, $R^1$ is —O$C_1$-$C_6$alkyl. In yet other aspects, $R^1$ is halo, $C_1$-$C_6$alkyl, —O$C_1$-$C_6$alkyl, or $C_1$-$C_6$haloalkyl. In other aspects, $R^1$ is halo or $C_1$-$C_6$haloalkyl.

In those aspects of the disclosure comprising compounds of formula I, when $R^1$ is halo, $C_1$-$C_6$alkyl, —O$C_1$-$C_6$alkyl, or $C_1$-$C_6$haloalkyl, the $R^1$ is preferably present at the 4-carbon position of the naphthyl or quinoline ring. In other aspects of the disclosure comprising compounds of formula I, when $R^1$ is halo, $C_1$-$C_6$alkyl, —O$C_1$-$C_6$alkyl, or $C_1$-$C_6$haloalkyl, the $R^1$ can be present at the 2-carbon position of the naphthyl or quinoline ring. Preferably, in those aspects of the disclosure comprising compounds of formula I. $R^1$ is F or $CF_3$ at the 4-carbon position of the naphthyl or quinoline ring.

In those aspects of the disclosure comprising compounds of formula II, when $R^1$ is halo, $C_1$-$C_6$alkyl, —O$C_1$-$C_6$alkyl, or $C_1$-$C_6$haloalkyl, the $R^1$ is preferably present at the 2-carbon position of the phenyl or pyridyl ring. In other aspects of the disclosure comprising compounds of formula II, when $R^1$ is halo, $C_1$-$C_6$alkyl, —O$C_1$-$C_6$alkyl, or $C_1$-$C_6$haloalkyl, the $R^1$ can be present at the 3-carbon position of the phenyl or pyridyl ring. Preferably, in those aspects of the disclosure comprising compounds of formula II, $R^1$ is F or $CF_3$ at the 2-carbon position of the phenyl or pyridyl ring.

According to the disclosure, $R^{1A}$ is H, halo, $C_1$-$C_6$alkyl, —O$C_1$-$C_6$alkyl, or $C_1$-$C_6$haloalkyl. In preferred aspects, $R^{1A}$ is H. In some aspects, $R^{1A}$ is halo (F, Cl, Br, or I). In other preferred aspects, $R^{1A}$ is $C_1$-$C_6$alkyl, for example, methyl, ethyl, isopropyl, butyl, and t-butyl. In some aspects, $R^{1A}$ is —O$C_1$-$C_6$alkyl, for example, methoxy, ethoxy, isopropoxy, butoxy. In yet other aspects, $R^{1A}$ is $C_1$-$C_6$haloalkyl, for example, —$CF_3$.

According to the disclosure. Y is CH or N. In some aspects. Y is CH. In other aspects, Y is N. In alternative embodiments, Y is —C($C_1$-$C_6$alkyl), for example, —C($CH_3$)— or C($CH_2CH_3$).

According to the disclosure, W is CH, —C($C_1$-$C_6$alkyl)-, or N. In some aspects, W is CH. In other aspects, W is —C($C_1$-$C_6$alkyl)-, for example, —C($CH_3$)—. —C($CH_2CH_3$)—, —C(i-propyl), or —C(butyl)-. In other aspects, W is N. In some aspects, W is CH or —C($C_1$-$C_6$alkyl)-. In other aspects, W is CH or N. In yet other aspects, W is N or —C($C_1$-$C_6$alkyl)-.

In some aspects, Y is CH and W is CH. In other aspects. Y is CH and W is N. In other aspects, Y is N and W is CH. In still other aspects, Y is N and W is N. In some aspects, Y is CH and W is C($C_1$-$C_6$alkyl). In other aspects, Y is N and W is C($C_1$-$C_6$alkyl).

According to the disclosure, n is 0, 1, 2, 3, or 4. In preferred aspects, n is 2. In other aspects, n is 0. In other aspects, n is 1. In yet other aspects, n is 3. In still other aspects, n is 4. In some aspects, n is 0 to 2 or 1 to 2. In yet other aspects, n is 1 to 3.

According to the disclosure, L is unsubstituted $C_1$-$C_6$alkylene, for example, unsubstituted $C_1$-$C_5$alkylene, $C_1$-$C_4$alkylene, $C_1$-$C_3$alkylene, $C_1$-$C_2$alkylene, or $C_1$alkylene. In other aspects, L is $C_1$-$C_6$alkylene, for example, $C_1$-$C_5$alkylene, $C_1$-$C_4$alkylene, $C_1$-$C_3$alkylene, $C_1$-$C_2$alkylene, or $C_1$alkylene, substituted with one, two, or three, preferably one or two substituents, independently selected from $C_1$-$C_6$alkyl (e.g., methyl, ethyl, propyl, isopropyl, butyl, s-butyl, t-butyl, pentyl, or hexyl), $C_1$-$C_6$haloalkyl (e.g., $CF_3$), $C_1$-$C_6$alkenyl (e.g., —CH=$CH_2$ or —$CH_2$—CH=$CH_2$), and —$C_1$-$C_6$alkO$C_1$-$C_6$alkyl, for example, —$C_1$-$C_5$alkO$C_1$-$C_6$alkyl, —$C_1$-$C_4$alkO$C_1$-$C_6$alkyl, —$C_1$-$C_3$alkO$C_1$-$C_6$alkyl, —$C_1$-$C_2$alkO$C_1$-$C_6$alkyl, —C₁alkOC₁-C₆alkyl, —C₁-C₆alkOC₁-C₆alkyl, —C₁-C₆alkOC₁-C₄alkyl, —C₁-C₆alkOC₁-C₃alkyl, —C₁-C₆alkOC₁-C₂alkyl, or —C₁-C₆alkOC₁alkyl. In a preferred aspect, L is unsubstituted C₁alkylene. In another preferred aspect, L is a C₁alkylene substituted with one or two, preferably one, C₁-C₆alkyl (e.g., methyl or ethyl) substituents.

According to the disclosure, Z is a bond, —NH—, or —N(C₁-C₆alkyl)-. In some aspects, Z is a bond. In other aspects, Z is —NH—. In yet other aspects, Z is —N(C₁-C₆alkyl)-, for example —N(CH₃)—, —N(CH₂CH₃)—, —N(i-propyl)-, and —N(t-butyl)-.)-. In some aspects, Z is —NH— or —N(C₁-C₆alkyl). In other aspects, Z is a bond or —NH—.

According to the disclosure, B is an unsubstituted or substituted heteroaryl moiety. In preferred aspects, the heteroaryl is selected from benzoimidazolyl, imidazopyridinyl, benzothiazolyl, benzooxazolyl, triazolopyridinyl, pyrazolopyridinyl, quinazolinonyl, and imidazopyridazinyl. In some aspects, B is unsubstituted or substituted benzoimidazolyl. In some aspects, B is unsubstituted or substituted imidazopyridinyl. In some aspects, B is unsubstituted or substituted benzothiazolyl. In some aspects, B is unsubstituted or substituted benzooxazolyl. In some aspects, B is unsubstituted or substituted triazolopyridinyl. In some aspects, B is unsubstituted or substituted pyrazolopyridinyl. In some aspects, B is unsubstituted or substituted quinazolinonyl. In some aspects, B is unsubstituted or substituted imidazopyridazinyl. The heteroaryl moiety can be attached to the compound of formula I or formula II through any available carbon or nitrogen atom of the heteroaryl moiety. Preferably, the heteroaryl is attached to the compound of formula I or formula II through an available carbon atom. In those embodiments wherein the heteroaryl is substituted, it can be substituted with one, two, three, or four, preferably one or two, R² substituents independently selected from halo, C₁-C₆alkyl, C₁-C₆haloalkyl, —CN, —OC₁-C₆alkyl, —OC₁-C₆haloalkyl, —COOH, —COOC₁-C₆alkyl, and dioxolanyl.

A preferred benzoimidazolyl moiety is

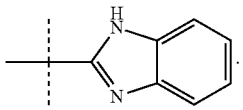

Preferred imidazopyridinyl moieties include

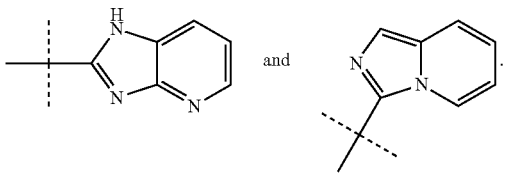 and

A preferred benzothiazolyl moiety is

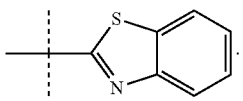

A preferred benzooxazolyl moiety is

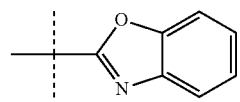

A preferred triazolopyridinyl moiety is

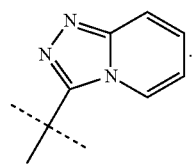

A preferred pyrazolopyridinyl moiety is

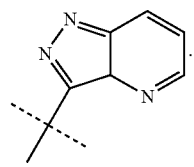

Preferred quinazolinonyl moieties include

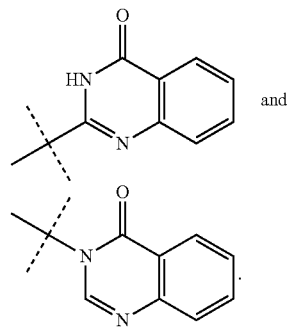 and

Preferred imidazopyridazinyl moieties include

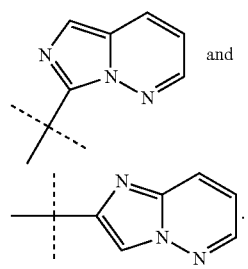 and

In some embodiments, the heteroaryl is substituted with at least one or two R² that is halo (e.g., F, Cl, or Br). In some embodiments, the heteroaryl is substituted with at least one or two R² that is C₁-C₆alkyl (e.g., methyl, ethyl, isopropyl, butyl, t-butyl, etc.). In some embodiments, the heteroaryl is substituted with at least one or two R² that is C₁-C₆haloalkyl (e.g., CF₃). In some embodiments, the heteroaryl is substituted with at least one or two R² that is —CN. In some embodiments, the heteroaryl is substituted with at least one or two R² that is —OC₁-C₆alkyl (e.g., methoxy, ethoxy, isopropoxy, etc.). In some embodiments, the heteroaryl is substituted with at least one or two R² that is —OC₁-C₆haloalkyl (e.g., —OCF₃). In some embodiments, the heteroaryl is substituted with at least one or two R² that is —COOH. In some embodiments, the heteroaryl is substituted with at least one or two R² that is —COOC₁-C₆alkyl (e.g., COOMe, —COOEt, etc.). In some embodiments, the heteroaryl is substituted with an R² that is dioxolanyl.

The invention also encompasses the pharmaceutically acceptable salts, stereoisomers, tautomers, and solvates of formulas I and II.

Sub-formulas of formula I include formulas wherein V is a bond, Y is CH, W is CH, n is 2, L is C₁alkylene, and Z is a bond, for example:

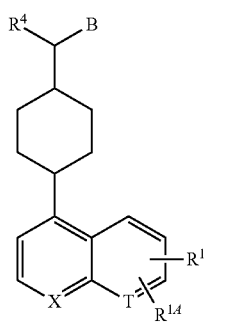

(I-A)

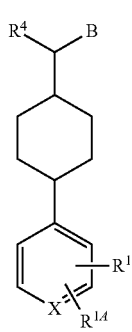

(II-A)

wherein X is CH and R⁴ is C₁-C₂alkyl. Other embodiments of formulas I-A and II-A include those wherein X is N and R⁴ is C₁-C₂alkyl. In other aspects, X is CH and T is CH. In some aspects, X is N and T is CH. In other aspects, X is CH and T is N. In other aspects, X is N and T is N. The invention also encompasses the pharmaceutically acceptable salts, stereoisomers, tautomers, and solvates of formulas I-A and II-A.

Sub-formulas of formula I include formulas wherein V is a bond, Y is N, W is CH, n is 2, L is C₁alkylene, and Z is a bond, for example:

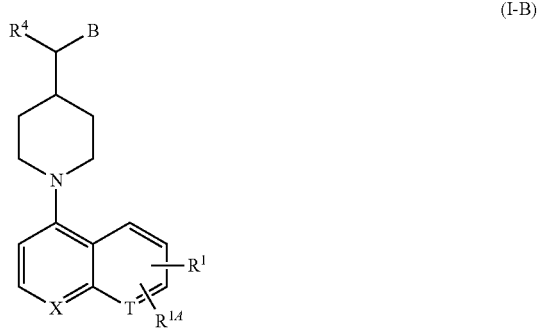

(I-B)

(II-B)

wherein X is CH and R⁴ is C₁-C₂alkyl. Other embodiments of formulas I-B and II-B include those wherein X is N and R⁴ is C₁-C₂alkyl. In other aspects, X is CH and T is CH. In some aspects, X is N and T is CH. In other aspects, X is CH and T is N. In other aspects, X is N and T is N. The invention also encompasses the pharmaceutically acceptable salts, stereoisomers, tautomers, and solvates of formulas I-B and II-B.

Sub-formulas of formula I include formulas wherein V is a bond, Y is CH, W is CH, n is 2, L is C₁alkylene, and Z is NH, for example:

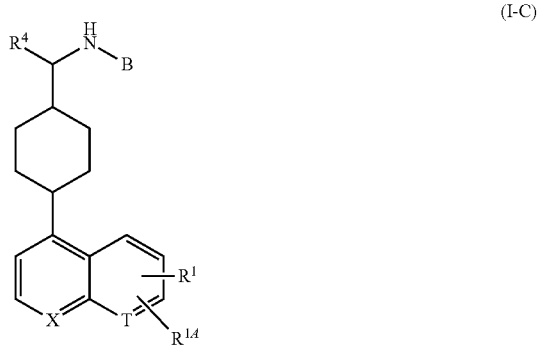

(I-C)

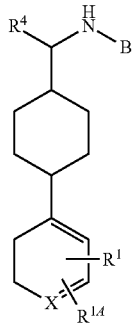

(II-C)

wherein X is CH and $R^4$ is $C_1$-$C_2$alkyl. Other embodiments of formulas I-C and II-C include those wherein X is N and $R^4$ is $C_1$-$C_2$alkyl. In other aspects, X is CH and T is CH. In some aspects, X is N and T is CH. In other aspects, X is CH and T is N. In other aspects, X is N and T is N. The invention also encompasses the pharmaceutically acceptable salts, stereoisomers, tautomers, and solvates of formulas I-C and II-C.

Sub-formulas of formula I include formulas wherein V is a bond, Y is N, W is CH, n is 2, L is $C_1$alkylene, and Z is NH, for example:

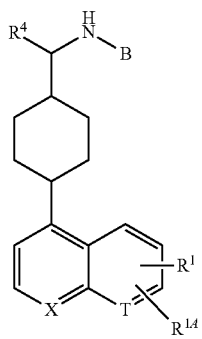

(I-D)

(II-D)

wherein X is CH and $R^4$ is $C_1$-$C_2$alkyl. Other embodiments of formulas I-D and II-D include those wherein X is N and $R^4$ is $C_1$-$C_2$alkyl. In other aspects, X is CH and T is CH. In some aspects, X is N and T is CH. In other aspects, X is CH and T is N. In other aspects, X is N and T is N. The invention also encompasses the pharmaceutically acceptable salts, stereoisomers, tautomers, and solvates of formulas I-D and II-D.

Sub-formulas of formula I include formulas wherein V is —O—, Y is CH, W is CH, n is 2, L is $C_1$alkylene, and Z is a bond, for example:

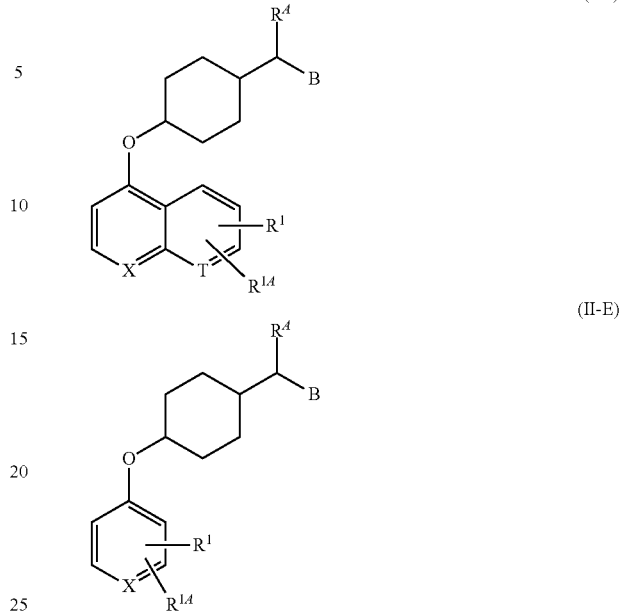

(I-E)

(II-E)

wherein X is CH and $R^4$ is $C_1$-$C_2$alkyl. Other embodiments of formulas I-E and II-E include those wherein X is N and $R^4$ is $C_1$-$C_2$alkyl. In other aspects, X is CH and T is CH. In some aspects, X is N and T is CH. In other aspects, X is CH and T is N. In other aspects. X is N and T is N. The invention also encompasses the pharmaceutically acceptable salts, stereoisomers, tautomers, and solvates of formulas I-E and II-E.

In another embodiment, the compounds of the invention have human IDO $IC_{50}$ values >50 nM. In another embodiment, the compounds of the invention have human IDO $IC_{50}$ values ≤50 nM. In another embodiment, the compounds of the invention have human IDO $IC_{50}$ values <5 nM.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgecnix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of Formula I or formula II is administered with one or more immuno-oncology agents. The immuno-oncology agents used herein, also known as cancer immunotherapies, are effective to enhance, stimulate, and/or upregulate immune responses in a subject.

In one aspect, the compound of Formula I or formula II is sequentially administered prior to administration of the immuno-oncology agent. In another aspect, the Compound of Formula I or formula II is administered concurrently with the immunology-oncology agent. In yet another aspect, the Compound of Formula I or formula II is sequentially administered after administration of the immuno-oncology agent.

In another aspect, the Compound of Formula I or formula II may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the Compound of Formula I or formula II and one or more of (i) an antagonist of a protein that inhibits T cell activation (e.g., immune checkpoint inhibitors) such as CTLA-4, PD-1. PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of Formula I or formula II for the treatment of cancer include antagonists of inhibitory receptors on NK cells or agonists of activating receptors on NK cells. For example, the Compound of Formula I or formula II can be combined with antagonists of KIR, such as lirilumab.

Yet other agents for combination therapies include agents that inhibit or deplete macrophages or monocytes, including but not limited to CSF-IR antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of Formula I or formula II can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MED14736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I and/or Formula II, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example. Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol ⸻ or ⟊ a is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" is intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). The term "alkenyl" refers to an alkyl group having one or more double bonds.

As used herein, "alkylene" (also referred to as "alk") denotes an alkylene having the specified number of carbon atoms. For example, "C$_1$-C$_6$alkylene" denotes an alkylene having 1 to 6 carbon atoms. Example alkylene groups include, but are not limited to, methylene (—CH$_2$—), ethylene (—CH$_2$CH$_2$—), and the like.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

As used herein, the term "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

As referred to herein, the term "substituted" means that at least one hydrogen atom is replaced with a non-hydrogen group, provided that normal valencies are maintained and that the substitution results in a stable compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012). The disclosure of which is hereby incorporated by reference.

In addition, compounds of formula I and formula II may have prodrug forms. Any compound that will be converted in vivo to provide the bioactive agent (i.e., a compound of formula I or II) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991):
c) Bundgaard, H., *Adv. Drug Deliv. Rev.*, 8:1-38 (1992):
d) Nielsen, N. M. et al., *J. Pharm. Si.*, 77:285 (1988);
e) Kakeya, N. et al., *Chem. Pharm. Bull.*, 32:692 (1984); and
g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I or formula II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or formula II include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*. The Royal Society of Chemistry. Cambridge, UK (Second Edition, reproduced, 2006); Testa, B. et al., *Hydrolysis in Drug and Prodrug Metabolism. Chemistry. Biochemistry and Enzymology*, VCHA and Wiley-VCH, Zurich, Switzerland (2003): Wermuth, C. G., ed., *The Practice of Medicinal Chemistry*, Third Edition, Academic Press. San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent. i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that arc non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Publication Nos. WO2016/073738, WO2016/073770, and WO2016/073774.

References to many of these chemical transformations employed herein can be found in Smith. M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Schemes 1-7 and 9 depict methods for preparing compounds of formula I. These methods can also be applied to the preparation of compounds of formula II as depicted in Scheme 8.

Treatment of a ketone (III) with an electrophilic triflating reagent such as triflic anhydride in the presense of an organic base such as 2,6-di-tert-butyl-4-methyl pyridine can give vinyl triflates of the general structure IV. For ketone III, other cyclic and acyclic ketal protecting groups could be employed in addition to the ethylene glycol-derived ketal shown. Alternatively, ketones of type III can be treated with a strong base just as LiHMDS and the resulting lithium enolate can be treated with N-phenyltrifluoromethanesulfonamide or other electrophilic triflating reagents. Conversion of the vinyl triflate IV to vinyl boronic ester V can be accomplished used standard conditions developed by Miyaura (T. Ishiyama, M. Murata, N. Miyaura, *J. Org. Chem.*, 1995, 60, 7508-7510.) Vinyl boronic esters such as V will participate in Suzuki couplings with a variety of coupling partners including but not limited to aryl and vinyl Scheme 1

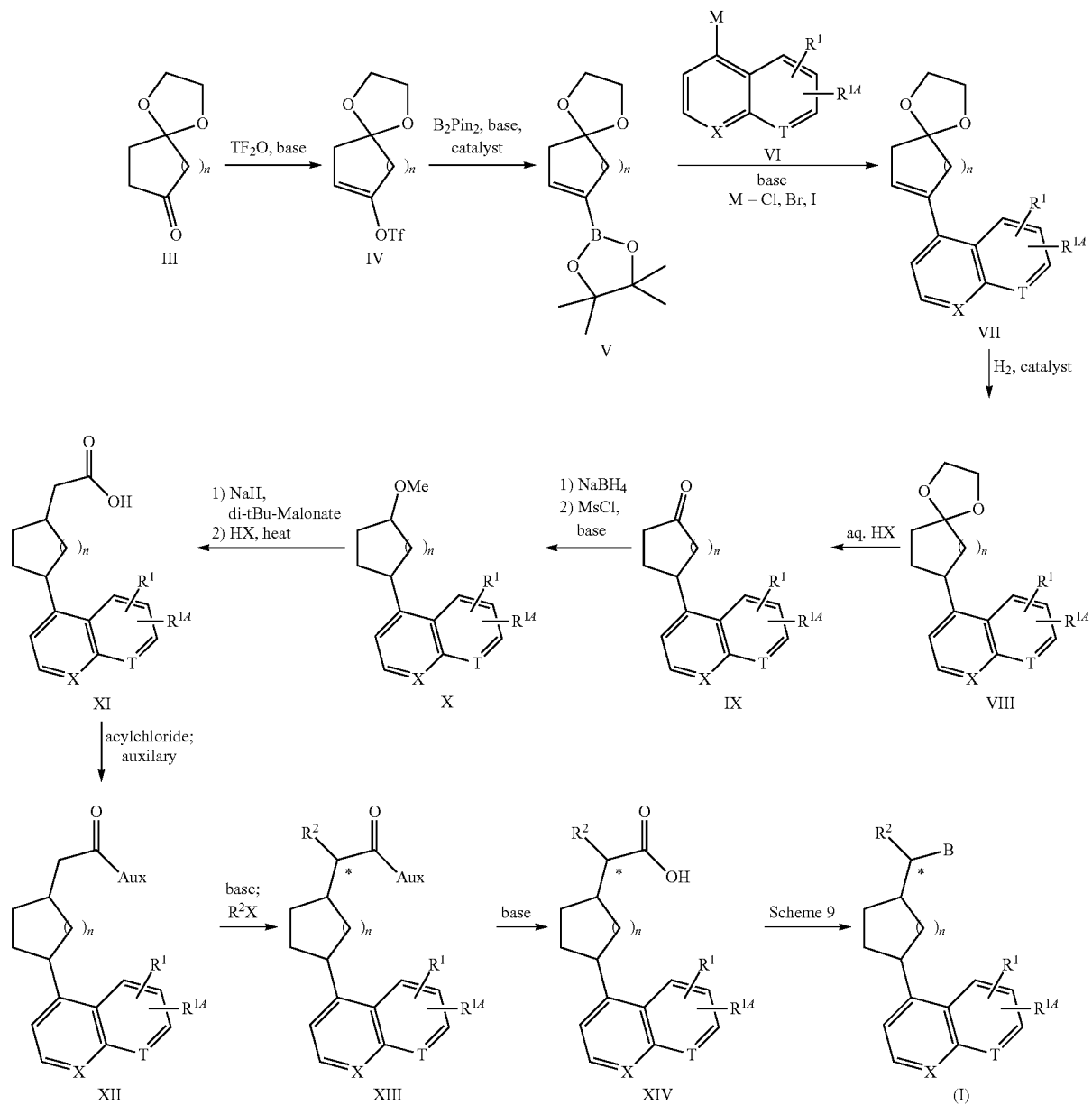

halides and aryl and vinyl triflates and more specifically a coupling partner such as VI. In addition to the pinacol boronic ester shown, boronic acids and other derivatized boron species have also been employed successfully in Suzuki couplings. Many variations of the Suzuki coupling are known, but generally they involve heating the two coupling partners in the presence of a base such as aq. potassium carbonate in a solvent such as DMF with a catalyst such as Pd(PPh$_3$)$_4$. Reduction of the olefin intermediate in the presence of a catalyst such as palladium on carbon in a solvent such a ethyl acetate under hydrogen at or above atmospheric pressure will give intermediates such as VIII. Ketal hydrolysis can be accomplished by stirring with an aqueous acid such as HCl with or without heating in the presence of co-solvents like THF or acetone. Ketone IX can be reduced to an alcohol with a variety of reducing agents including sodium borohydride and the resulting alcohol can be converted into a leaving group by treatment with an appropriate electrophile (in this case mesylchloride) in the presence of a base such as pyridine. Mesylate X can then be displaced by many nucleophiles including deprotonated di-tert-butyl malonate. In this case, the malonate was deprotonated with sodium hydride, but other bases can achieve this deprotonation. After displacement, hydrolysis of the tert-butyl ester can be affected with aqueous acid such as acetic acid and decarboxylation can occur upon heating under acidic conditions to provide carboxylic acids like XI. Installation of a chiral auxiliary onto the acid XI can be brought about by first treating with an acyl chloride, such as pivaloyl chloride, to form a mixed anhydride followed by adding into this a deprotonated auxiliary such as an Evan's oxazolidinone (D. A. Evans, M. D. Ennis, D. J. Mathre; *J. Am. Chem. Soc.* 1982, 104, 1737-1739). Deprotonation of the resulting chiral imide XII with a base such as NaHMDS followed by treatment of the resulting enolate with a suitable electrophile R$^2$X can proceed with predictable control and in high diastereoselectivity at the newly-formed chiral center to provide materials XIII. Cleavage of the auxiliary can, in the cases of Evan's oxazolidinone based auxiliarys occur by treatment with aqueous base such as LiOH with or without the addition of hydrogen peroxide. For installation of a variety of fused heterocycles onto intermediate XIV, refer to Scheme 9.

Scheme 2

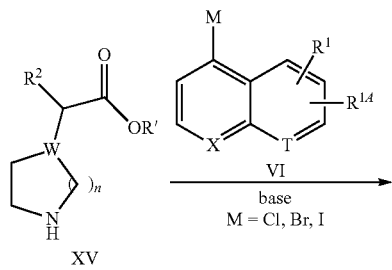

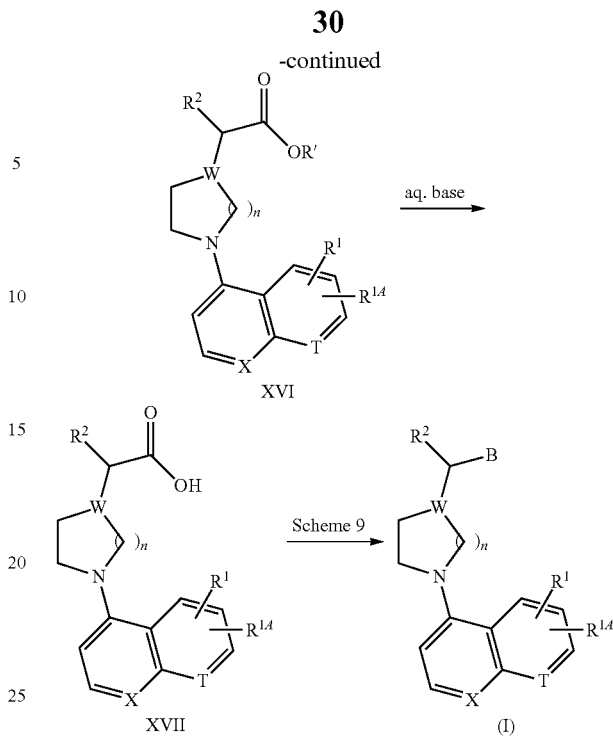

Piperidine, piperazine, and pyrrolidine derived esters XV are known compounds that can undergo S$_N$Ar reactions with or without the addition of a base such as DIPEA. The resulting esters XVI can be hydrolyzed under a variety of conditions usually employing aqueous base or acid to give carboxylic acids XVII. For installation of a variety of fused heterocycles onto intermediate XVII, refer to Scheme 9.

Scheme 3

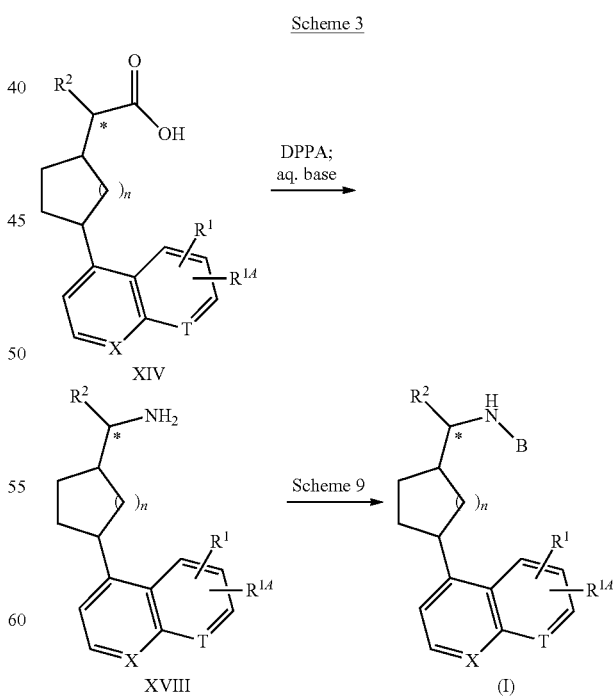

Alternatively, acids like intermediate XIV can be converted to amine XVIII upon treatment with diphenylphosphorylazide (DPPA) followed by interception and subsequent decarboxylation of the resulting isocyanate with a basic aqueous solution such as LiOH. For installation of a variety of fused heterocycles onto intermediate XVIII, refer to Scheme 9.

Scheme 4

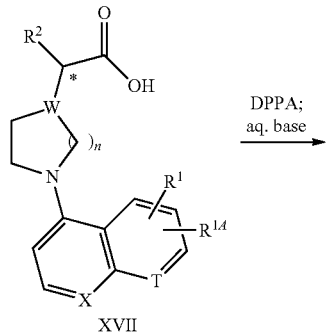

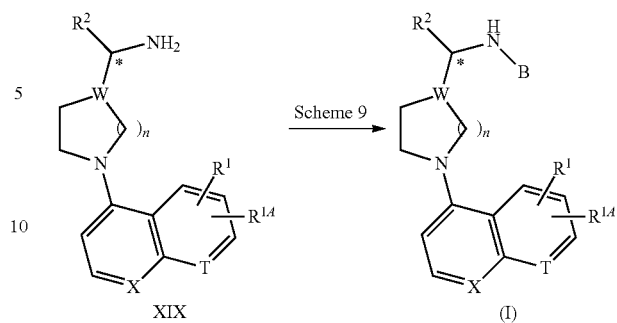

Similarly to Scheme 3, intermediates XVII in cases where W=—CH— or —C(C$_1$-C$_6$alkyl)- can also be treated with DPPA followed by treatment with a basic aqueous solution to give amines XIX. For installation of a variety of fused heterocycles onto intermediate XIX, refer to Scheme 9.

Scheme 5

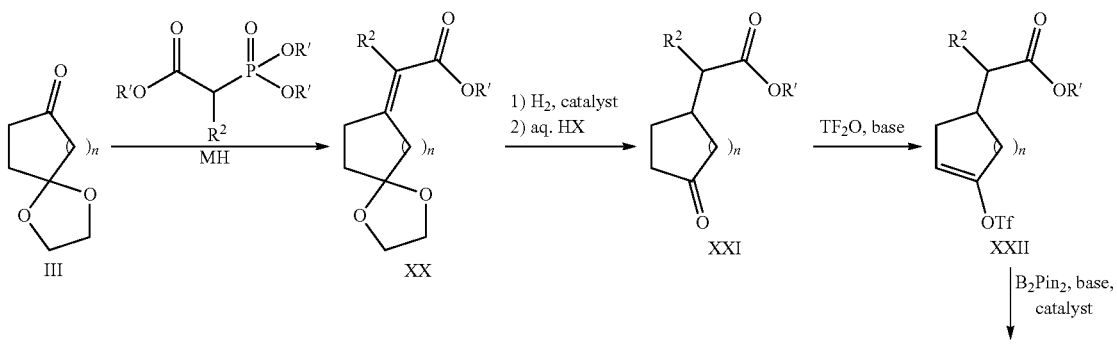

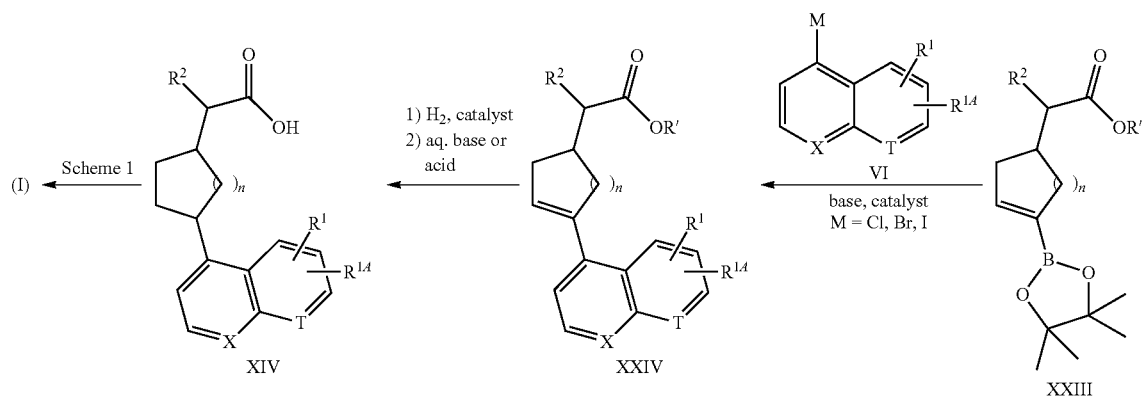

Treatment of a phosphonoacetate ester with a based such as sodium hydride in a solvent such as THF followed by a ketone of general structure III affords a tri- (when $R^2$=H) or tetrasubstituted olefin XX. Alternative methods for olefination and the transformations described below are known and will be selected by one skilled in the art based on their applicability to the specific substrate under consideration. Reduction of the olefin XX is accomplished by stirring or shaking a solution of the olefin in a suitable solvent under an atmosphere or more of hydrogen gas in the presence of a catalyst, normally palladium on carbon. Hydrolysis of the ketal group affords a ketone of the general structure XXI. Typically this is accomplished by heating with an aqueous acid such as HCl in the presence of a co-solvent such as THF or acetone. In addition to the cyclic ethylene glycol-based ketal shown, other cyclic and acyclic ketal protection groups could be employed. Conversion of the ketone to the triflate XXII, to the boronic ester XXIII, to the Suzuki product XXIV can proceed as outlined in Scheme 1. Suzuki product XXIV can be reduced under hydrogenation conditions as discussed previously and the resulting ester can be hydrolysed to acid XIV upon treatment with either basic or acidic aqueous media depending on the nature of R'. For installation of a variety of fused heterocycles onto intermediate XIV, refer to Scheme 9.

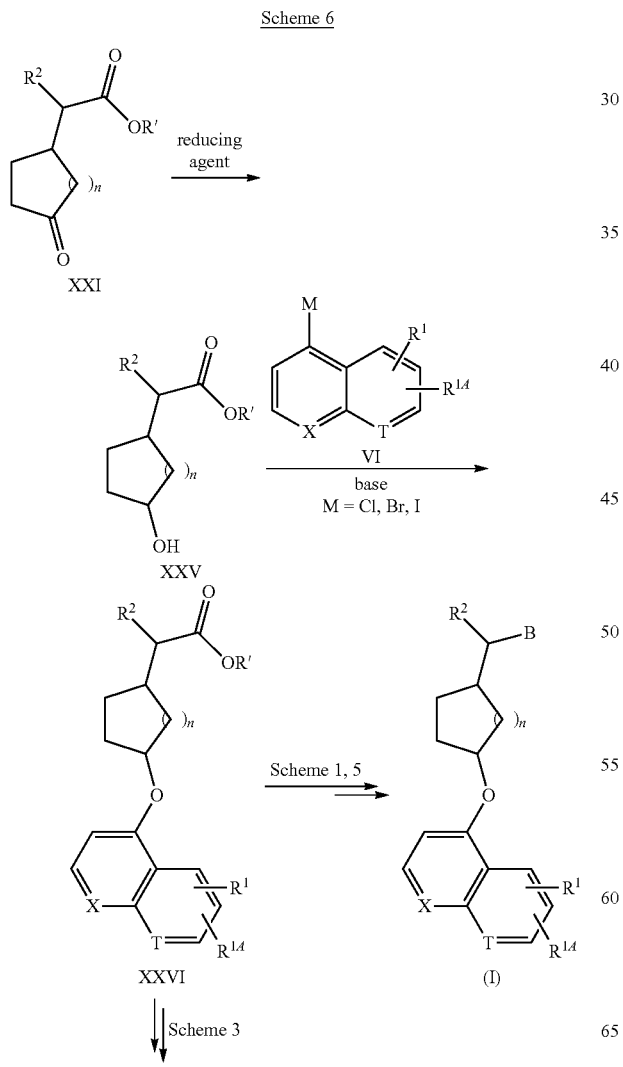

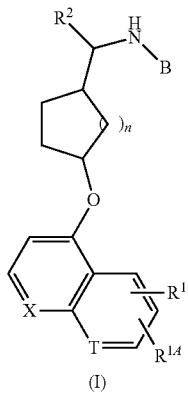

Alternatively, ketones XXI can be reduced with several reducing agents preferably sodium borohydride in a suitable solvent like ethanol to give rise to alcohols like XXV. These alcohols can, in a similar fashion to piperidines and piperazines discussed in Scheme 2, also undergo $S_NAr$ reactions with substrates such as VI in the presence of a base such as sodium tert-butoxide in an appropriate polar aprotic solvent such as DMF to give ethers of type XXVI. These ethers can be elaborated to a variety of structures described by formula I using chemistry depicted in Schemes 1, 3, and 5. For installation of a variety of fused heterocycles, refer to Scheme 9.

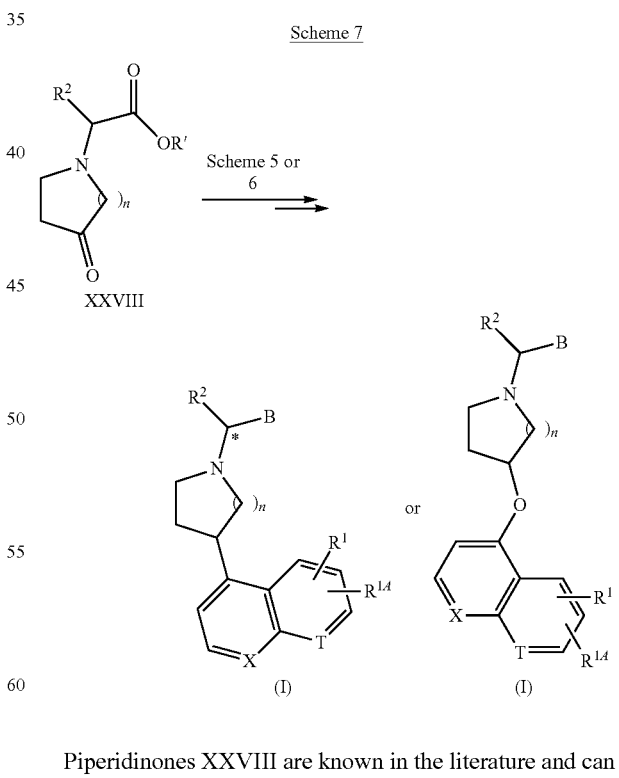

Piperidinones XXVIII are known in the literature and can be elaborated to either directly linked or ether linked compounds of formula I using chemistry depicted in Schemes 5 or 6. For installation of a variety of fused heterocycles, refer to Scheme 9.

Scheme 8

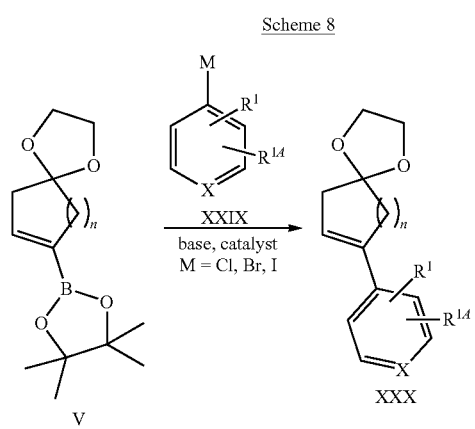

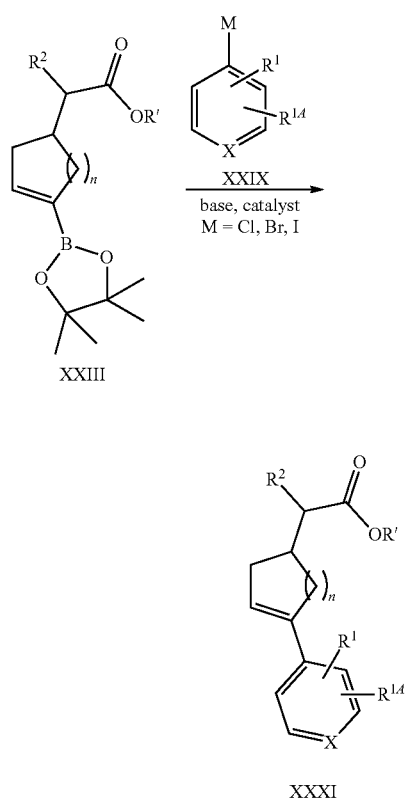

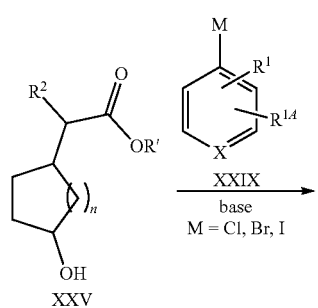

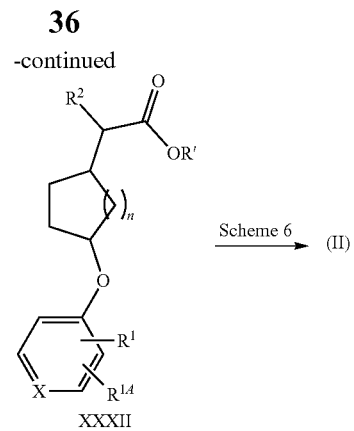

Using intermediates described previously (such as V, XXIII, and XXV), compounds of formula II can be synthesized by utilizing a coupling partner and electrophile of type XXIX to give olefins XXX or XXXI as well as ethers XXXII. These can, again, be elaborated to compounds of formula II utilizing the same sequence of reactions outlines in Schemes 1, 5, and 6. For installation of fused heterocycles, refer to Scheme 9.

Scheme 9

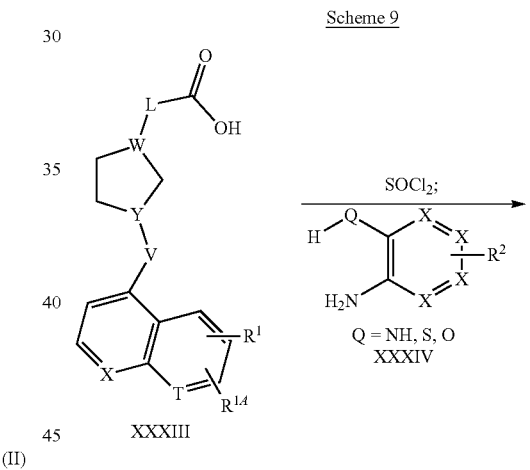

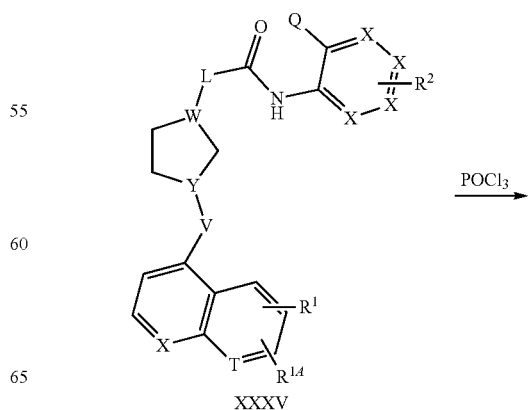

-continued
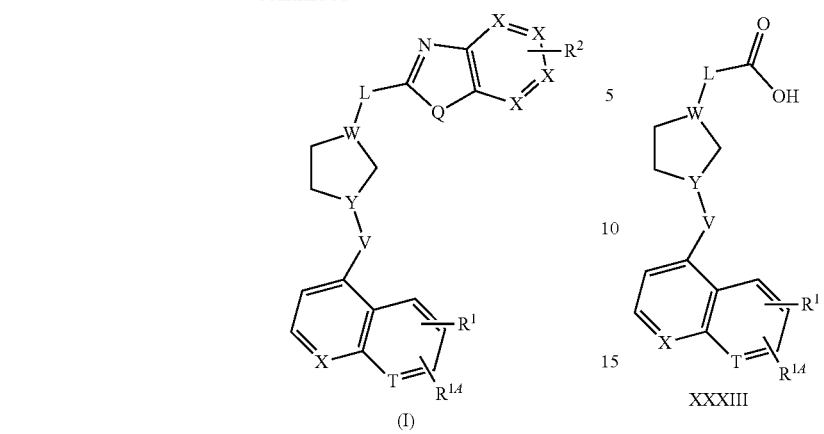
(I)
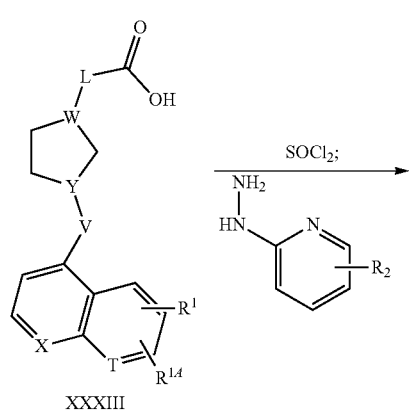
XXXIII
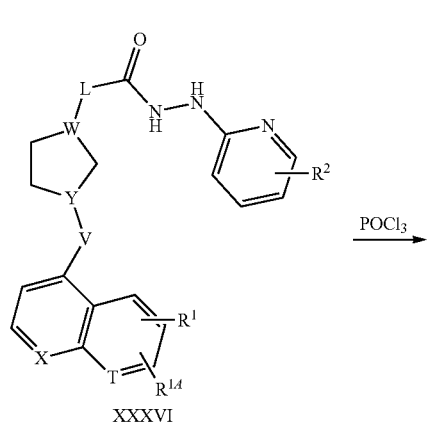
XXXVI
-continued
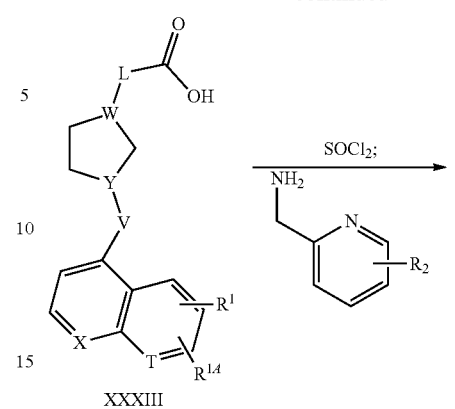
XXXIII
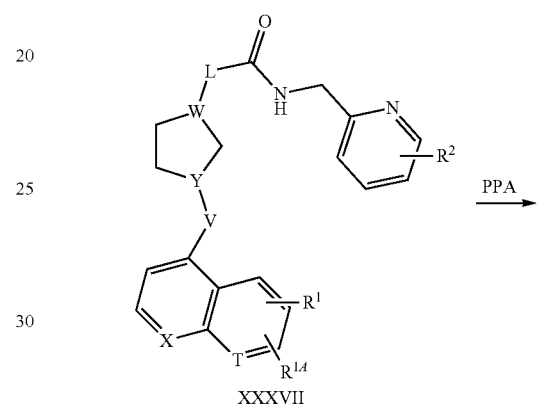
XXXVII
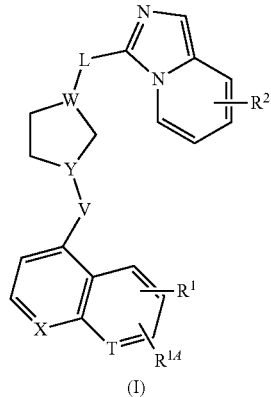
(I)
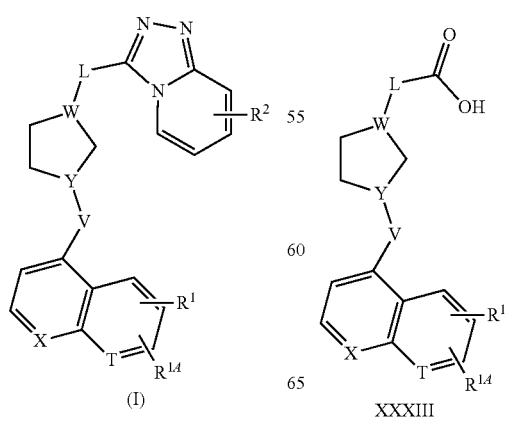
XXXIII -continued
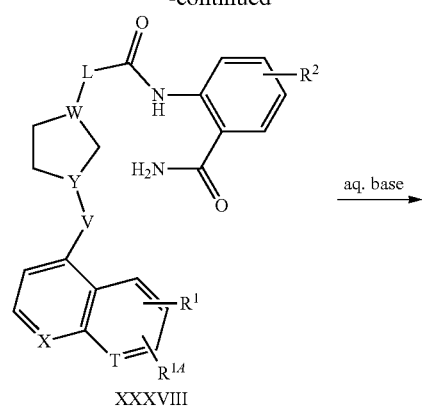
XXXVIII
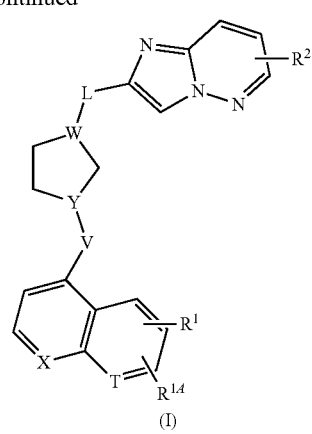
(I)
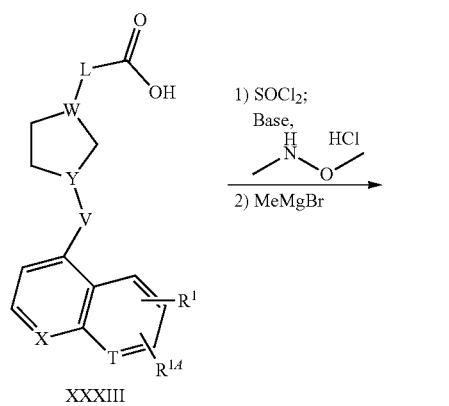
(I)
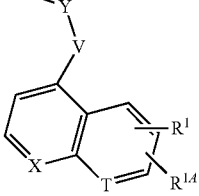 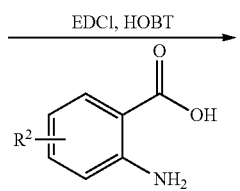
XL
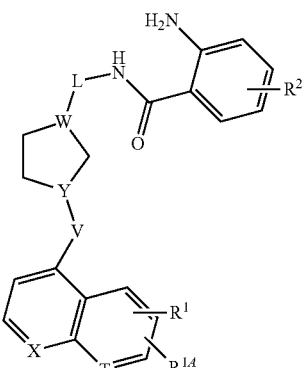
XXXIII
XLI
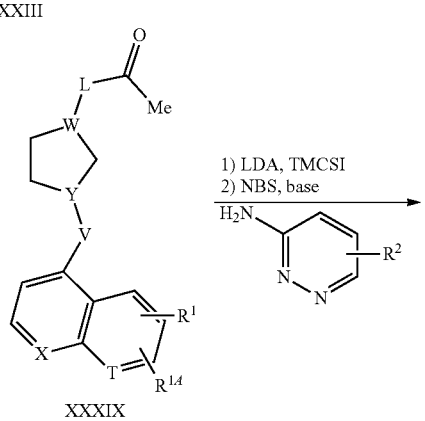
XXXIX
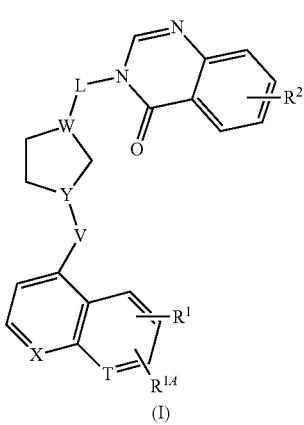
(I)

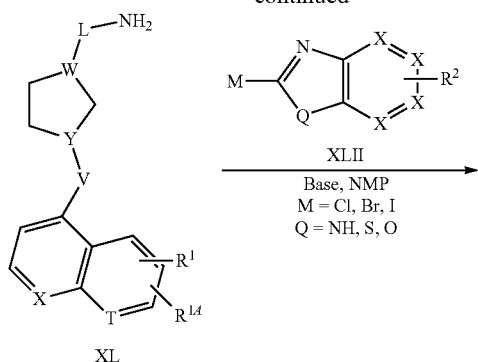

XL

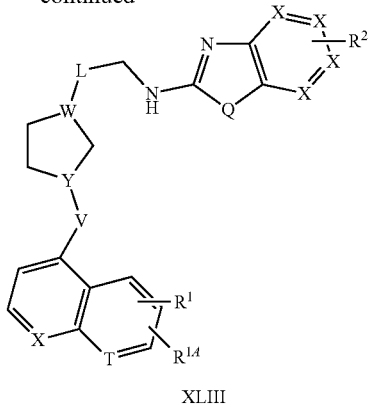

XLIII

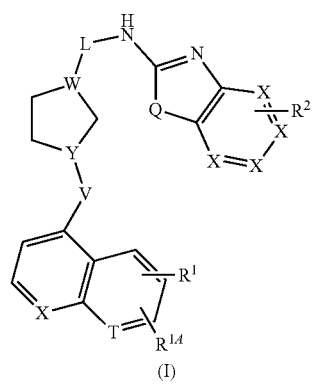

(I)

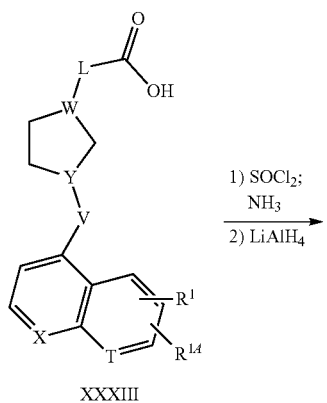

XXXIII

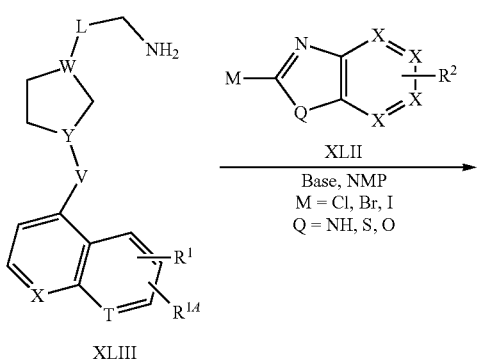

XLIII

An advanced intermediate of type XXXIII can be elaborated into a variety of fused heterocyclic compounds of formula (I) and these sequences could also be applied to an advanced intermediate that would lead to compounds of formula (II). Intermediate XXXIII can be converted to an acyl chloride and quenched with an appropriate nucleophile of type XXXIV to give amides XXXV. Amides XXXV can be treated with acidic, activating, or dehydrating agents, preferably phosphorous oxychloride, to give compounds of formula (I). The acyl chloride of intermediate XXXIII can also be intercepted with 2-hydroazino-pyridines or 2-methylamino-pyridines to give intermediate XXXVI or XXXVII respectively. These can also be treated with a suitable acidic, activating, or dehydrating agent to give compounds of formula (I). If the acyl chloride of intermediate XXXIII is trapped with an anthranilamide to give amides like XXXVIII, treatment with aqueous base, such as sodium hydroxide, in the presence of a co-solvent such as ethanol, will provide compounds of formula (I) as well. In another application, the acyl chloride of intermediate XXXIII can be converted to the Weinreb amide, followed by treatment with methyl magnesium bromide to give a methyl ketone XXXIX. This methyl ketone can be brominated and treated with 3-amino-pyridazines to also give compounds of formula (I). If an amine of type XL is made (as resulting from Schemes 3 and 4) it can be coupled with anthranilic acid under standard amide bond forming conditions using a wide variety of coupling reagents including EDCI and HOBT to give an amide XLI. Treatment of this amide with an orthoformate in the presence of acid and heat will lead to compounds of formula (I). This amine XL can also competently undergo $S_NAR$ reactions with electrophiles of type XLII in the presense of a base such as diisopropylethyl amine in the presence of suitable polar, aprotic solvent such as NMP to give compounds of formula (I). Finally, the acyl chloride of intermediate XXXIII can be trapped with ammonia followed by treatment with a strong reducing agent such as lithium aluminum hydride to give a primany amine XLIII. This amine can also competently undergo $S_NAR$ reactions with electrophiles of type XLII in the presense of a base such as diisopropylethyl amine in the presence of suitable polar, aprotic solvent such as NMP to give compounds of formula (I). It should be noted that Scheme 9 merely represents a small selection of possible transformations yielding fused heterocycles from intermediate that can be obtained in Schemes 1-8. Many other fused heterocycles beyond those depicted in Scheme 9 could be derived from intermediates obtained in Schemes 1-8.

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

Analytical HPLC/MS was performed using the following methods:

Method A: Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Method B: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B: Flow: 1.00 ml/min; Detection: UV at 220 nm.

Method C: Preparative Chromatographic Conditions: Instrument: Berger Prep SFC MGII (LVL-L4021 Lab); Column: Chiral IC 25×3 cm ID, 5 µm; Flow rate: 85.0 ml/min; Mobile Phase: 74/26 $CO_2$/MeOH; Detector Wavelength: 220 nm.

Method D: Preparative Chromatographic Conditions: Instrument: Berger Prep SFC MGII (LVL-L4021 Lab); Column: Chiral Phenomenex Cellulose-4 25×3 cm ID, 5 µm; Flow rate: 85.0 mL/min; Mobile Phase: 70/30 $CO_2$/MeOH; Detector Wavelength: 220 nm.

Method E: Preparative Chromatographic Conditions: Instrument: Berger Prep SFC MGII (LVL-L4021 Lab); Column: Chiral Phenomenex Cellulose-4 25×3 cm ID, 5 µm; Flow rate: 85.0 mL/min; Mobile Phase: 70/30 $CO_2$/MeOH w/0.1% DEA; Detector Wavelength: 220 nm.

Method G: Berger Prep SFC MGII (LVL-L4021 Lab); Column: Chiral AD 25×3 cm, 5 µm; Flow rate: 85.0 mL/min; Mobile Phase: 80/20 $CO_2$/MeOH; Detector Wavelength: 220 nm; Sample Prep and Inj. Volume: 500 µL of 21.3 mg dissolved in 4 mL MeOH Method H: Aurora analytical SFC (LVL-L4021 Lab), Column: Chiral AD 250×4.6 mm ID, 5 µm; Flow rate: 2.0 ml/min; Mobile Phase: 80/20 $CO_2$/MeOH Method I: Column: Chiralpak AD-H, 30×250 mm, 5 micron; Flow Rate: 100 mL/min; Oven Temperature: 40° C.; BPR Setting: 120 bar; UV wavelength: 220; Mobile Phase: 75% CO2/25% Isopropanol-0.1% DEA (isocratic); Injection: 1250 uL of 19 mg/2 mL Methanol Method J; Column: Chiralpak AD-H, 4.6×100 m, 5 micron (analytical); Flow Rate: 2 mL/min; Oven Temperature: 40° C.; BPR setting; 1700 psi; UV wavelength: 220 nm; Mobile Phase: 75% $CO_2$/25% Isopropanol-0.1% DEA (isocratic)

Method K: Instrument: Berger Prep SFC MGII (LVL-L4021 Lab)Column; Phenomenex Cellulose-4 25×3 cm, 5 µm Flow rate: 85.0 mL/min; Mobile Phase: 80/20 $CO_2$/MeOH/ACN 50:50; Detector Wavelength: 220 nm; Sample Prep and Inj. Volume: 2000 µL of 6.0 mg dissolved in 3 mL MeOH Method L: Instrument: Aurora analytical SFC (LVL-L4021 Lab); Column: Phenomenex Cellulose-4l 250×4.6 mm ID, 5 µm; Flow rate: 2.0 mL/min; Mobile Phase: 80/20 $CO_2$/MeOH/CAN 50:50

Method M: Column: Chiralpak AD, 30×250 mm, 5 micron; Flow Rate: 100 mL/min; Oven Temperature: 40° C.; BPR Setting: 120 bar; UV wavelength: 220 nm; Mobile Phase: 80% $CO_2$/20% Methanol-0.1% DEA (isocratic); Injection: 2100 uL of 12 mg/3 mL Methanol Method N: Column: Chiralpak AD, 4.6×100 m, 5 micron (analytical); Flow Rate: 2 mL/min.; Oven Temperature: 40° C.; BPR setting: 1700 psi; UV wavelength: 220 nm; Mobile Phase: 80% $CO_2$/20% Methanol-0.1% DEA (isocratic)

Method O: Column: Chiralcel OD, 30×250 mm, 5 micron; Flow Rate: 100 mL/min; Oven Temperature: 40° C.; BPR Setting: 120 bar; UV wavelength: 220 nm; Mobile Phase: 90% $CO_2$/10% Methanol-0.1% DEA (isocratic); Injection: 500 uL of 9.9 mg/2.0 mL Methanol Method P: Chiralcel OD 4.6×100 mm, 5 micron (analytical); Flow Rate: 2 mL/min.; Oven Temperature: 40° C.; BPR setting: 1700 psi; UV wavelength: 220 nm; Mobile Phase: 90% CO2/10% Methanol-0.1% DEA (isocratic)

Method Q: Column: Chiralpak IC, 21×250 mm, 5 micron; Flow Rate: 60 mL/min; Oven Temperature: 40° C.; BPR Setting: 120 bar; UV wavelength: 220 nm; Mobile Phase: 75% $CO_2$/25% Isopropanol-0.10% DEA (isocratic); Injection: 350 uL of 19 mg/3 mL Methanol Method R: Column: Chiralpak IC, 4.6×100 mm, 5 micron (analytical); Flow Rate: 2 mL/min.; Oven Temperature: 40° C.; BPR setting: 1700 psi; UV wavelength: 220 nm; Mobile Phase: 75% $CO_2$/25% Isopropanol-0.1% DEA (isocratic)

Method S: Column: Chiralpak AD. 30×250 mm, 5 micron; Flow Rate: 100 mL/min; Oven Temperature: 40° C.; BPR Setting: 120 bar; UV wavelength: 220 nm; Mobile Phase: 80% $CO_2$/20% Isopropanol-0.1% DEA (isocratic); Injection: 1500 uL of 13 mg/3 mL Methanol Method T: Column: Chiralpak AD, 4.6×100 mm, 5 micron (analytical); Flow Rate: 2 mL/min.; Oven Temperature: 40° C.; BPR setting: 1700 psi; UV wavelength: 220 nm; Mobile Phase: 80% $CO_2$/20% Isopropanol-0.1% DEA (isocratic)

Method U: Column: Chiralpak AD, 30×250 mm, 5 micron; Flow Rate: 100 mL/min; Oven Temperature: 40° C.; BPR Setting: 120 bar; UV wavelength: 220 nm; Mobile Phase: 85% CO$_2$/15% Methanol-0.1% DEA (isocratic); Injection: 1500 uL of 19 mg/3 mL Methanol Method V: Column: Chiralpak AD, 4.6×100 mm, 5 micron (analytical); Flow Rate: 2 mL/min.; Oven Temperature: 40° C.; BPR setting: 1700 psi; UV wavelength: 220 nm; Mobile Phase: 85% CO$_2$/15% Methanol-0.1% DEA (isocratic)

Example 1

4-((cis)-4-((R)-1-(1H-benzo[d]imidazol-2-yl)ethyl)cyclohexyl)-6-fluoroquinoline

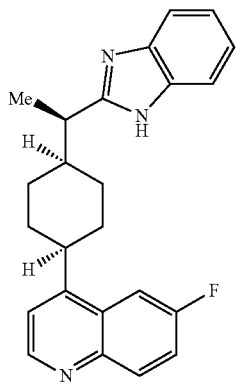 [SMILES: C[C@@H](c1nc2ccccc2[nH]1)[C@H]1CC[C@@H](c2ccnc3ccc(F)cc32)CC1]

Example 1: 4-((cis)-4-((R)-1-(1H-benzo[d]imidazol-2-yl)ethyl)cyclohexyl)-6-fluoroquinoline Preparation 1A:

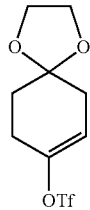

To a stirred solution of 1,4-dioxaspiro[4.5]decan-8-one (300 g, 1920.86 mmol, 1.0 eq) and N-phenyltrifluoromethanesulfonimide (823.47 g, 2305.03 mmol, 1.2 eq) in MTBE (7.5 L) under N$_2$ at −78° C. was added 2.0 M NaHMDS in THF (1152.2 mL, 2305.03 mmol, 1.2 eq) over 70 minutes, and the mixture was stirred for an additional 60 minutes. The reaction mixture was warmed to room temperature and stirred overnight until TLC showed complete consumption of the starting material. The mixture was quenched with aqueous KHSO$_4$ (100 ml), filtrated to remove the solid and concentrated the filtrate completely. To the residue was added 3 L MTBE, then washed with 5% NaOH (1.5 L×3). The organic phase was concentrated to obtain 567 g crude Preparation 1A (light yellow oil, yield 102%). The crude can be used directly in next step without further purification.

Preparation 1A: $^1$H NMR (400 MHz, CDCl$_3$): δ (ppm) 5.65 (t, J=4.0 Hz, 1H), 3.98 (d, J=1.5 Hz, 4H), 2.53 (s, 2H), 2.40 (s, 2H), 1.90 (t, J=6.6 Hz, 2H)

Preparation 1B:

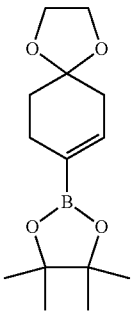

A mixture of crude Preparation 1A (600 g, 2.08 mol, 1 eq), B$_2$Pin$_2$ (687.1 g, 2.71 mol, 1.3 eq), KOAc (613 g, 6.24 mol, 3 eq), NaBr (86 g, 0.833 mol, 0.4 eq) and Pd(dppf)Cl$_2$ (76 g, 0.1 mol, 0.05 eq) in dioxane (6.5 L) was heated to reflux overnight. Once the reaction was complete, the mixture was concentrated and purified by FCC (2%→10%→20% EtOAc/PE) to give Preparation 1B (369 g, 66%).

Preparation 1B: LC-MS: 267.1 (M+1)+, $^1$H NMR (400 MHz, CDCl$_3$) δ 6.46 (s, 1H). 3.98 (s, 4H). 2.37-2.35 (m, 4H), 1.74-1.60 (t, 2H), 1.24 (s, 12H).

Preparation 1C:

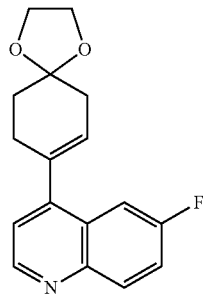 [SMILES: Fc1ccc2nccc(C3=CCC4(CC3)OCCO4)c2c1]

A mixture of Preparation 1B (368 g, 1.38 mol, 1.3 eq), 4-chloro-6-fluoroquinoline (195 g, 1.07 mol, 1 eq), K$_2$CO$_3$ (445 g, 3.22 mol, 3 eq) and Pd(PPh$_3$)$_4$ (25 g, 22 mmol, 0.02 eq) in dioxane-water (3 L, 4:1) was heated to reflux overnight. The solution was then concentrated and extracted with EtOAc. Purification by FCC (38% EtOAc/petroleum ether) gave Preparation 1C (236 g, 77%).

Preparation 1C: LC-MS: 286.1 (M+1)+, $^1$H NMR (400 MHz, CDCl$_3$) δ 8.80-8.29 (d, 1H), 8.11-8.07 (q, 1H), 7.63-7.61 (q, 1H), 7.47-7.46 (q, 1H), 7.26-7.22 (m, 1H), 5.75-5.74 (m, 1H), 4.08-4.05 (m, 4H), 2.63-2.59 (m, 2H), 2.59-2.53 (m, 2H), 2.0-1.97 (m, 2H).

Preparation 1D:

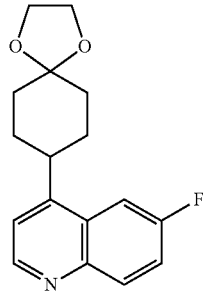 [SMILES: Fc1ccc2nccc(C3CCC4(CC3)OCCO4)c2c1]

To Preparation 1C (125 g, 0.44 mol) in IPA (2 L) at 55° C. was added 10% Pd/C and the mixture was stirred under an atmosphere of H₂ overnight. The mixture was filtered and concentrated to give crude Preparation 1D (130 g), which was used directly in the next step.

Preparation 1E:

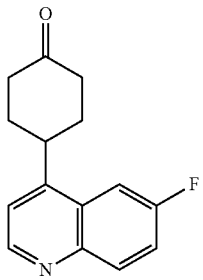 [SMILES: O=C1CCC(c2ccnc3ccc(F)cc23)CC1]

Preparation 1D (100 g, 0.348 mol) was treated with 4 N HCl (300 mL) in acetone (1200 mL) at 45° C. overnight. The mixture was monitored by TLC. Then the solution was then concentrated in vacuo. The residue was adjusted to pH 9 with 6 N NaOH and the mixture was partitioned between ethyl acetate and water. The organic layer was washed with brine, dried over anhydrous Na₂SO₄, filtered and concentrated to give light yellow solid, which was then purified by silica gel column using hexanes and ethyl acetate (from 20 percent ethyl acetate to 70% ethyl acetate) to afford Preparation 1E as a white solid, (47 g+20 g mixture, yield >55%). Preparation 1E: LC-MS: 244.0 (M+1)+, ¹H NMR (400 MHz, CDCl₃) δ 8.84 (d, J=4.6 Hz, 1H), 8.16 (dd, J=9.3, 5.7 Hz, 1H), 7.72 (dd, J=10.3, 2.8 Hz, 1H), 7.52 (ddd, J=9.2, 7.8, 2.7 Hz, 1H), 7.29 (d, J=4.6 Hz, 1H), 3.69 (ddd, J=12.1, 9.0, 3.3 Hz, 1H), 2.77-2.54 (m, 4H), 2.37 (ddd, J=13.4, 5.9, 3.0 Hz, 2H), 2.04 (qd, J=12.6, 5.3 Hz, 2H).

Preparation 1F:

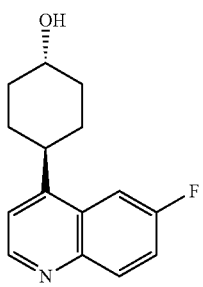 [SMILES: O[C@H]1CC[C@H](c2ccnc3ccc(F)cc32)CC1]

Intermediate 1E (57.8 g, 237.8 mmol) was dissolved in EtOH (240 mL) and cooled to 0° C. NaBH₄ (9.94 g, 261.6 mmol) was added portionwise maintaining the temperature within a range of 0-10° C. (exothermic reaction). The resulting suspension was stirred for 20 minutes. An LC/MS of an aliquot of the reaction mixture indicated consumption of ketone (m/z (M+H)+=244). The reaction was quenched at 0° C. by the slow addition of acetone (58 mL) over 15 minutes (exotherm). The reaction was poured slowly onto 500 mL of saturated aqueous ammonium chloride and 500 g of ice. The resulting aqueous solution was extracted with EtOAc (3×300 mL) and the combined organic fractions were washed with saturated aqueous ammonium chloride (250 mL) and saturated aqueous sodium chloride (250 mL). The organic portion was dried over anhydrous sodium sulfate and concentrated under reduced pressure. Sufficient silica to adsorb the oil was added and diluted with 10% MeOH in CH₂Cl₂. A similar quantity of silica was used as a silica plug to purify the material. The silica plug was washed with 10% MeOH in CH₂Cl₃ until UV-active material no longer could be detected by TLC (7:3 EtOAc/Hexanes, R_f=0.4). The filtrate was concentrated then suspended in 500 mL of toluene and concentrated again. Crude Preparation 1F was isolated as a yellow solid (58.2 g) that was used in the subsequent step without further purification.

Preparation 1G

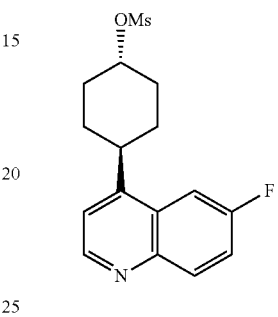

To Preparation 1F (58.2 g, 237.8 mmol) was added MeCN (125 mL) and pyridine (38.7 mL, 480 mmol) and the reaction mixture was cooled to 5° C. using an ice/water bath. Methanesulfonyl chloride (26.0 mL, 336 mmol) was added dropwise at 5° C. (exothermic reaction), the reaction mixture stirred for 1 hr at 5° C. and then brought up to room temperature and stirred for an additional 16 h during which time a white precipitate formed. The heterogeneous mixture was quenched by the addition of saturated aqueous ammonium chloride (200 mL) and extracted with CH₂Cl₂ (3×300 mL). The combined organic fractions were dried over anhydrous sodium sulfate and concentrated under reduced pressure. Excess pyridine was removed by azeotroping from toluene (3×300 mL). The crude material was recrystallized from H₂O/MeOH as follows: 1 mL/mmol of H₂O was added and the slurry was heated to 120° C. in an oil bath. MeOH was added until the solids went into solution (~0.5 L). After cooling white crystals were collected by filtration to give Preparation 1G (58.6 g, >20:1 dr, 76% over two steps). m/z (M+H)+=324.1. H-NMR (400 MHz; CDCl₃): δ 8.82 (dd, J=4.6, 0.2 Hz, 1H), 8.15-8.11 (m, 1H), 7.64-7.61 (m, 1H), 7.52-7.46 (m, 1H), 7.25 (s, 1H), 4.78 (tt, J=10.9, 5.2 Hz, 1H), 3.24-3.16 (m, 1H), 3.07 (d, J=1.0 Hz, 3H), 2.42-2.38 (m, 2H), 2.16-2.12 (m, 2H), 1.93-1.66 (m, 4H).

Preparation 1H:

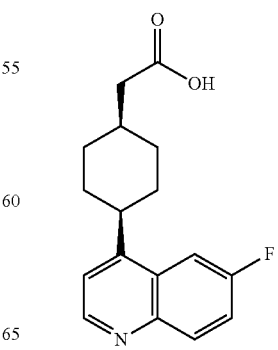

Di-tert-butyl malonate (33.5 mL, 150 mmol) was added dropwise to a stirred suspension of NaH (6.0 g, 60% suspension in oil, 150 mmol) in 1,2-dimethoxyethane (100 mL) under Ar, cooled in a water-ice bath. After stirring for 10 min, Preparation 1G (16.2 g, 50 mmol) was added and the reaction was heated at 85° C. for 20 h. After this time, acetic acid (100 mL) was added, the reaction flask was fitted with a distillation head and the temperature was raised to 130° C. 1,2-dimethoxyethane was distilled off under atmospheric pressure until the distillate was acidic (~100 mL). The distillation head was removed, a reflux condenser was attached, water (20 mL) was added and the reaction heated at 130° C. for 12 h. The reaction was concentrated under reduced pressure and poured onto 200 g of ice and 100 mL of saturated aqueous NaOAc. Preparation 1H was isolated as a white solid by filtration and further dried by refluxing with toluene in a Dean-Stark apparatus (11.0 g, 76%). m/z (M+H)=288.2. $^1$H-NMR (400 MHz; DMSO-$d_6$): δ 12.05 (bs, 1H), 8.79 (d, J=4.5 Hz, 1H), 8.06 (dd, J=9.2, 5.8 Hz, 1H), 7.94 (dd, J=11.0, 2.8 Hz, 1H), 7.66-7.61 (m, 1H), 7.50 (d, J=4.6 Hz, 1H), 2.41 (d, J=7.6 Hz, 2H), 2.28-2.23 (m, 1H), 1.87-1.78 (m, 2H), 1.73-1.64 (m, 6H).

Preparation 1I:

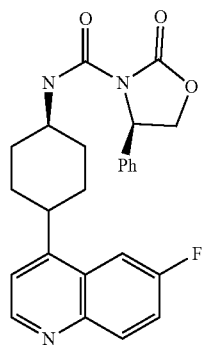

To a solution of Preparation 1H (1.4 g, 4.8 mmol) in THF (15 mL) was added NEt$_3$ (1.3 mL, 9.6 mmol). The reaction mixture was cooled to 0° C. and trimethylacetyl chloride (0.713 mL, 5.8 mmol) was added dropwise and the resulting solution stirred for 30 min at 0° C. In a separate flask, (R)-4-phenyloxazolidin-2-one (3, 1.01 g, 6.24 mmol) in THF (45 mL) at 0° C. was treated with 1 M LiHMDS solution in THF (dropwise addition of 6.24 mL, 6.24 mmol) and stirred at 0° C. The lithiated was added via cannula to the first flask. The reaction mixture was allowed to warm to rt and was stirred for 3 hours. LC/MS indicated the complete consumption of the starting carboxylic acid and formation of the desired imide. The reaction mixture was poured onto saturated aqueous ammonium chloride (50 mL) and the layers were separated. The aqueous layer was extracted with EtOAc (3×50 mL). The combined organic extracts were dried over anhydrous sodium sulfate and chromatographed on silica using EtOAc/Hexanes 0 to 100% gradient to give Preparation 1I as a white foam in 83% yield. m/z (M+H)= 433.3. $^1$H-NMR (400 MHz; CDCl$_3$): δ 8.80 (d, J=4.5 Hz, 1H), 8.11 (dd, J=9.1, 5.7 Hz, 1H), 7.63 (dd, J=10.5, 2.5 Hz, 1H), 7.48-7.43 (m, 1H), 7.40-7.30 (m, 6H), 5.47-5.44 (m, 1H), 4.71 (t, J=8.9 Hz, 114), 4.31-4.28 (m, 1H), 3.20-3.11 (m, 3H), 2.49-2.46 (m, 1H), 1.82-1.67 (m, 614).

Preparation 1J:

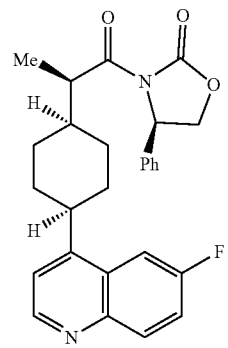 [SMILES: C[C@@H](C(=O)N1C(=O)OC[C@H]1c1ccccc1)[C@H]1CC[C@@H](c2ccnc3ccc(F)cc32)CC1]

A solution of Preparation 1I (21.6 g, 50 mmol) in anhydrous THF (200 mL) was cooled to −40° C. (using acetonitrile/dry ice bath, some precipitation occurs) and 2 M NaHMDS solution in THF (30 mL, 60 mmol) was added over 5 min (a 5-8° C. rise in temperature was observed). The resulting yellow reaction mixture was stirred for 10 min, became homogeneous, and MeI (10.6 g, 75 mmol) was added dropwise over 2 min (a 10° C. rise in temperature was observed). The reaction mixture was stirred for 1 h at −40° C. and LC/MS indicated the complete consumption of the starting material and formation of the desired methyl imide. The reaction mixture was rapidly diluted with saturated aqueous ammonium chloride solution (400 mL) and the biphasic mixture was stirred for 15 min. $^i$PrOAc (100 mL) was added, the layers were separated, and the aqueous layer was extracted with $^i$PrOAc (3×50 mL). The combined organic extracts were dried over anhydrous magnesium sulfate filtered, and concentrated. The resulting residue was recrystallized by dissolving in 400 mL hot acetone and adding H$_2$O until a milky solution formed followed to re-dissolving with heating (~3:1 acetone/H$_2$O). Preparation 1J was obtained as white needles (15.04 g, 2 crops, 68%). m/z (M+H)$^+$=447.3. $^1$H-NMR (400 MHz; CDCl$_3$): δ 8.81 (d, J=4.6 Hz, 1H), 8.10 (dd, J=9.2, 5.7 Hz, 1H), 7.65 (dd, J=10.6, 2.7 Hz, 1H), 7.47-7.42 (m, 1H), 7.41-7.29 (m, 6H), 5.47 (dd, J=8.8, 3.8 Hz, 1H), 4.69 (t, J=8.9 Hz, 1H), 4.38-4.30 (m, 1H), 4.26 (dd, J=8.9, 3.9 Hz, 1H), 3.26-3.21 (m, 1H), 2.18-2.15 (m, 1H), 1.93-1.64 (m, 8H), 1.09 (d, J=6.9 Hz, 3H).

Preparation 1K:

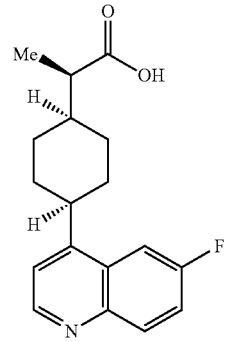

To a solution of Preparation 1J (82.0 g, 183.6 mmol) in THF (610 mL) at 0° C. was added aqueous H$_2$O$_2$ (35 wt %, 82 mL) and LiOH (7.04 g, 293.8 mmol) in H$_2$O (189 mL). The resulting reaction mixture was allowed to slowly warm to rt and stirred overnight. The reaction was cooled to 0° C.

and saturated aqueous sodium bisulfite solution (250 mL) was added. After stirring for 30 min, the THF was removed under reduced pressure. Acetic acid (34 mL) was added followed by EtOAc (300 mL). The layers were separated, and the aqueous layer was extracted with EtOAc (3×500 mL). The combined organic extracts were dried over anhydrous $Na_2SO_4$, filtered, and concentrated under reduced pressure. The brown crude reaction mixture was suspended in MeCN (400 mL) and the suspension was brought to reflux with vigorous stirring. After cooling to rt, the solids were collected by filtration washing with additional MeCN. Preparation 1K was obtained as a white solid (45.4 g, 82%). m/z $(M+H)^+$=302.2. $^1$H-NMR (400 MHz; DMSO-$d_6$): δ 12.10 (s, 1H), 8.79 (d, J=4.5 Hz, 1H), 8.07 (dd, J=9.2, 5.9 Hz, 1H), 7.97-7.94 (m, 1H), 7.67-7.62 (m, 1H), 7.49 (d, J=4.5 Hz, 1H), 3.41-3.36 (m, 1H), 2.73-2.65 (m, 1H), 1.83-1.61 (m, 9H), 1.08 (d, J=6.8 Hz, 3H). Chiral HPLC, >99% ee (ChiralPak IC-3, 3 µM, 4.6×250 mm, 15 min isocratic 70% heptane 30% i-PrOH with 230 nm detection) at a flow rate of 0.75 mL/min the desired enantiomer had a retention time of 8.6 min with the undesired enantiomer eluting at 9.5 min.

Example 1: 4-((cis)-4-((R)-1-(1H-benzo[d]imidazol-2-yl)ethyl)cyclohexyl)-6-fluoroquinoline Preparation 1K (30 mg, 0.100 mmol) was dissolved in THF (498 µl). Then, Hunig's Base (43.5 µl, 0.249 mmol), PYBROP (69.6 mg, 0.149 mmol), and benzene-1,2-diamine (21.53 mg, 0.199 mmol) were added. Reactions stirred at room temperature for 20 hours and then heated to 70° C. for 4 hours The reaction was diluted with 5:1 water/sat $NaHCO_3$ and extracted with EtOAc. Organics dried with sodium sulfate filtered and concentrated in vacuo. The residue was taken up in Acetic Acid (498 µl) and heated to 110° C. After 1 hour at 110° C. the reaction was diluted with water and quenched with sat $NaHCO_3$ and extracted with EtOAc. Organics dried with sodium sulfate, filtered and concentrated in vacuo.

The crude residue was taken up in Toluene (0.5 mL) and Tosic Acid (5 equiv) was added. Reaction was refluxed overnight. Reaction concentrated, taken up in 2 mL DMF, filtered and purified via preparative HPLC to give Example 1. (7.0 mg, 0.018 mmol, 18% yield) LC-MS Anal. Calc'd for $C_{24}H_{24}FN_3$ 373.20, found [M+H] 374.1 $T_r$=1.736 min (Method B). $^1$H NMR (500 MHz, DMSO-$d_6$) δ: 8.91 (d, J=4.6 Hz, 1H), 8.13 (dd, J=9.1, 5.7 Hz, 1H), 8.05 (d, J=11.0 Hz, 1H), 7.81 (dd, J=6.0, 3.1 Hz, 2H), 7.69-7.77 (m, 1H), 7.55 (dd, J=6.1, 2.9 Hz, 2H), 7.14 (d, J=8.7 Hz, 1H), 6.94 (d, J=8.3 Hz, 1H), 3.69-3.80 (m, 1H), 2.22 (br. s., 1H), 2.06 (br. s., 1H), 1.84-2.00 (m, 2H), 1.63-1.84 (m, 5H), 1.59 (d, J=10.4 Hz, 1H), 1.49 (d, J=6.8 Hz, 3H).

Examples 2-7

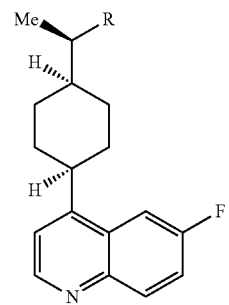

Examples 2-7 were prepared from Preparation 1K utilizing the procedure from Example 1 and the corresponding phenylene diamines.

| Ex. No. | Name | R | Tr (min) (Method B) | [M + H]⁺ |
|---|---|---|---|---|
| 2 | 4-((cis)-4-((R)-1-(6-chloro-1H-benzo[d]imidazol-2-yl)ethyl)cyclohexyl)-6-fluoroquinoline | | 1.966 | 408.1 |
| 3 | 6-fluoro-4-((cis)-4-((R)-1-(6-fluoro-1H-benzo[d]imidazol-2-yl)ethyl)cyclohexyl)quinoline | | 1.835 | 392.3 |
| 4 | 6-((R)-1-((cis)-4-(6-fluoroquinolin-4-yl)cyclohexyl)ethyl)-5H-[1,3]dioxolo[4',5':4,5]benzo[1,2-d]imidazole | | 1.734 | 418.1 |

| Ex. No. | Name | R | Tr (min) (Method B) | [M + H]+ |
|---|---|---|---|---|
| 5 | 4-((cis)-4-((R)-1-(1H-imidazo[4,5-c]pyridin-2-yl)ethyl)cyclohexyl)-6-fluoroquinoline | | 1.461 | 375.3 |
| 6 | 4-((cis)-4-((R)-1-(6-chloro-1H-imidazo[4,5-b]pyridin-2-yl)ethyl)cyclohexyl)-6-fluoroquinoline | | 1.748 | 409.2 |
| 7 | 4-((cis)-4-((R)-1-(1H-imidazo[4,5-b]pyridin-2-yl)ethyl)cyclohexyl)-6-fluoroquinoline | | 1.521 | 375.3 |

Example 8

6-chloro-N—((R)-1-((cis)-4-(6-fluoroquinolin-4-yl)cyclohexyl)ethyl)benzo[d]thiazol-2-amine

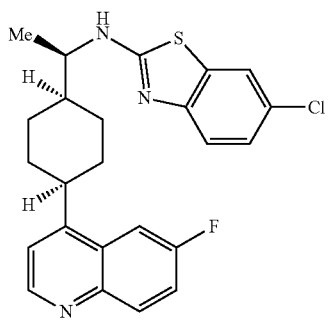 [SMILES: C[C@@H](Nc1nc2ccc(Cl)cc2s1)[C@H]1CC[C@@H](c2ccnc3ccc(F)cc32)CC1]

Preparation 8A:

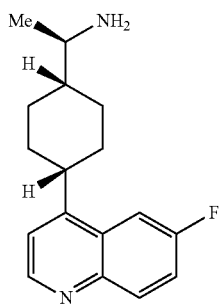 [SMILES: C[C@@H](N)[C@H]1CC[C@@H](c2ccnc3ccc(F)cc32)CC1]

Preparation 1K (2 g, 6.64 mmol) was taken up in toluene (22.12 ml) and diphenyl phosphorazidate (2.009 g, 7.30 mmol) and triethylamine (1.110 ml, 7.96 mmol) were added. Vial sealed and heated to 70° C. After 2 hours, the reaction was cooled to room temperature and concentrated under reduced pressure. Crude residue was taken up in 40 mL THF and 40 mL of water and lithium hydroxide (1.589 g, 66.4 mmol) was added. The reaction was stirred at room temperature for 1 hour. The reaction was acidified with 1N HCl (white precipitate forms) and extracted with EtOAc. The aqueous portion was then basified with 1N NaOH (precipitate forms) and extracted with EtOAc 5 times. Basic extracts were concentrated in vacuo to give 8A (1.68 g, 6.17 mmol, 93% yield). LC-MS Anal. Calc'd for $C_{17}H_{21}FN_2$ 272.17, found [M+H] 273.1 $T_r$=0.50 min (Method A). $^1$H NMR (400 Mhz, chloroform-d) δ: 8.80 (d, J=4.6 Hz, 1H), 8.11 (dd, J=9.3, 5.7 Hz, 1H), 7.67 (dd, J=10.6, 2.8 Hz, 1H), 7.46 (ddd, J=9.2, 8.0, 2.8 Hz, 1H), 7.32 (d, J=4.5 Hz, 1H), 3.27-3.37 (m, 1H), 3.13 (dq, J=9.3, 6.3 Hz, 1H), 2.01-2.10 (m, 1H), 1.67-1.92 (m, 6H), 1.37-1.55 (m, 4H), 1.15 (d, J=6.4 Hz, 3H).

Example 8: 6-chloro-N—((R)-1-((cis)-4-(6-fluoroquinolin-4-yl)cyclohexyl)ethyl)benzo[d]thiazol-2-amine Preparation 8A (34.8 mg, 0.077 mmol, 69.7% yield) was dissolved in NMP (110 μl) and DIPEA (57.7 μl), 0.330 mmol), 2,6-dichlorobenzo[d]thiazole (45.0 mg, 0.220 mmol) was added and the reaction was sealed and heated to 150° C. After 1 hour, the reaction was diluted with DMF, filtered and purified via preparative HPLC to give Example 8 (34.8 mg, 0.077 mmol, 70% yield). LC-MS Anal. Calc'd for $C_{24}H_{23}ClFN_3S$ 439.13, found [M+H] 440.1 $T_r$=2.420 min (Method B). $^1$H NMR (500 MHz, DMSO-$d_6$) δ: 8.83 (d, J=4.4 Hz, 1H), 8.04-8.11 (m, 2H), 7.95 (d, J=10.8 Hz, 1H), 7.74 (s, 1H), 7.65 (t, J=7.5 Hz, 1H), 7.50 (d, J=4.3 Hz, 1H), 7.33 (d, J=8.6 Hz, 1H), 7.20 (d, J=8.3 Hz, 1H), 4.27 (br. s., 1H), 3.45 (br. s., 1H), 1.59-1.94 (m, 9H), 1.24 (d, J=6.2 Hz, 3H)

Examples 9-12

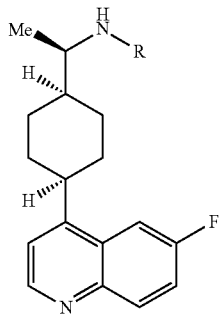

Examples 9-12 were prepared from Preparation 8A utilizing the procedure from Example 8 and the corresponding heteroaryl halides.

Example 13

4-(((trans)-4-(1-(6-chloro-H-benzo[d]imidazol-2-yl)propyl)cyclohexyl)oxy)quinoline

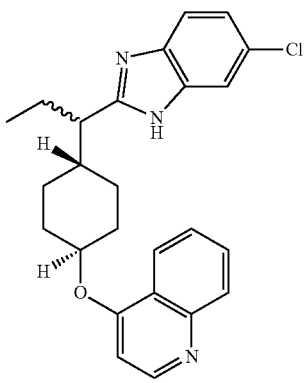 [SMILES: CCC(c1nc2ccc(Cl)cc2[nH]1)[C@H]1CC[C@H](Oc2ccnc3ccccc23)CC1]

| Ex. No. | Name | R | Tr (min) (Method B) | [M + H]+ |
|---|---|---|---|---|
| 9 | N-((R)-1-((cis)-4-(6-fluoroquinolin-4-yl)cyclohexyl)ethyl)-6-methoxy-1H-benzo[d]imidazol-2-amine | | 1.550 | 419.2 |
| 10 | N-((R)-1-((cis)-4-(6-fluoroquinolin-4-yl)eyclohexyl)ethyl)benzo[d]thiazol-2-amine | | 2.209 | 406.1 |
| 11 | 6-chloro-N-((R)-1-((cis)-4-(6-fluoroquinolin-4-yl)cyclohexyl)ethyl)benzo[d]oxazol-2-amine | | 2.277 | 424.2 |
| 12 | N-((R)-1-((cis)-4-(6-fluoroquinolin-4-yl)cyclohexyl)ethyl)-1H-benzo[d]imidazol-2-amine | | 1.602 | 389.3 |

Intermediate 13A: ethyl 2-(1,4-dioxaspiro[4.5]decan-8-ylidene)acetate

Triethyl phosphonoacetate (21.79 ml, 109 mmol) was added to a suspension of sodium hydride (3.84 g, 96 mmol) in THF (64.0 ml) and 0° C. Reaction was stirred at room temperature for 30 minutes. After 30 minutes, the reaction was recooled to 0° C. and a solution of 1,4-dioxaspiro[4.5]decan-8-one (10 g, 64.0 mmol) in 5 mL THF was added. The reaction was then stirred at room temperature for 30 minutes prior to quenching with water. The mixture was extracted with DCM three times. Combined organic extracts were dried with sodium sulfate, filtered, and concentrated in vacuo. Crude residue was purified via silica gel chromatography to give intermediate 13A (13.88 g, 61.3 mmol, 96% yield). TLC: product stains as purple spot in anisaldehyde (Rf=0.75 in 1:1 Hex/EtOAc). $^1$H NMR (400 MHz, CHLOROFORM-d) δ: 5.65 (s, 1H), 4.13 (q, J=7.2 Hz, 2H), 3.92-3.99 (m, 4H), 2.94-3.02 (m, 2H), 2.31-2.40 (m, 2H), 1.71-1.79 (m, 4H), 1.26 (t, J=7.2 Hz, 3H)

Intermediate 13B: ethyl 2-(1,4-dioxaspiro[4.5]decan-8-yl)acetate

Intermediate 13A (13.88 g, 61.3 mmol) was taken up in EtOAc (61.3 ml) and was added to a Parr hydrogenation bottle containing wet 10% palladium on carbon (1.306 g, 12.27 mmol)(54% w/w Water) under an atmosphere of nitrogen. The reaction bottle was purged and back-filled with nitrogen three times, and then with hydrogen. After filling the bottle with hydrogen to 50 psi, the bottle was placed in a Parr shaker and shaken. After 4 hours, the reaction was filtered over pressed celite and concentrated in vacuo to give Intermediate 13B (13.78 g, 60.4 mmol, 98% yield). LC-MS Anal. Calc'd for $C_{12}H_{20}O_4$ 228.14, found [M+H] 299.1 $T_r$=0.83 min (Method A). $^1$H NMR (400 MHz, CHLOROFORM-d) δ: 4.11 (q, J=7.2 Hz, 2H), 3.88-3.95 (m, 4H), 2.21 (d, J=7.0 Hz, 2H), 1.83 (dqd, J=11.0, 7.5, 3.5 Hz, 1H), 1.68-1.78 (m, 4H), 1.50-1.61 (m, 2H), 1.27-1.35 (m, 2H), 1.24 (t, J=7.2 Hz, 3H)

Intermediate 13C: ethyl 2-(1,4-dioxaspiro[4.5]decan-8-yl)butanoate

Diisopropylamine (2.347 ml, 16.63 mmol) taken up in dry THF (15.99 ml) (under N2 atmosphere) and cooled to −78° C. n-BuLi (6.14 ml, 15.35 mmol) (2.5 M in hexanes) was added over ~5 minutes at −78° C. After stirring for 45 minutes, reaction was warmed to room temperature for 10 minutes and returned to −78° C. Then, 1,3-dimethyltetrahydropyrimidin-2(1H)-one (1.541 ml, 12.79 mmol) was added followed by a solution of Intermediate 13B (2.92 g, 12.79 mmol) in THF (15.99 ml) (dropwise over ~5 minutes). After 1 hour, iodoethane (1.125 ml, 14.07 mmol) (neat) was added dropwise over ~5 minutes. Reaction stirred another 2 hours at −78° C. before slowly warming to room temperature. The reaction was then stirred over night at room temperature. The reaction was quenched by pouring into 1:1 water/brine and extracting with EtOAc. Combined organics washed with brine, dried with sodium sulfate, filtered and concentrated in vacuo. Crude residue was purified via silica gel column chromatography to give Intermediate 13C (2.27 g, 8.86 mmol, 69% yield). TLC: product stains as purple spot in anisaldehyde (Rf=0.80 in 1:1 Hex/EtOAc). $^1$H NMR (400 MHz, CHLOROFORM-d) δ: 4.14 (q, J=7.5 Hz, 2H), 3.88-3.95 (m, 4H), 2.09 (td, J=8.4, 5.6 Hz, 1H), 1.69-1.83 (m, 4H), 1.45-1.64 (m, 6H), 1.33-1.42 (m, 1H), 1.25 (t, J=7.1 Hz, 3H), 0.86 (t, J=7.5 Hz, 3H)

Intermediate 13D: ethyl 2-(4-oxocyclohexyl)butanoate

Intermediate 13C (2.00 g, 7.80 mmol) was taken up in THF (39.0 ml) and hydrochloric acid, 1M (39.0 ml) was added. Reaction stirred at room temperature for 2 hours. The reaction was concentrated in vacuo, diluted with water and extracted with EtOAc. The combined organic extracts were dried with sodium sulfate, filtered and concentrated in vacuo. The crude material was purified on silica gel column chromatography to give Intermediate 13D (1.47 g, 6.92 mmol, 89% yield). TLC: product stains faintly pink in anisaldehyde (Rf=0.65 in 1:1 Hex/EtOAc). $^1$H NMR (400 MHz, CHLOROFORM-d) δ: 4.15 (q, J=7.1 Hz, 2H), 2.25-2.42 (m, 4H), 2.18 (ddd, J=9.3, 7.8, 5.2 Hz, 1H), 2.10 (ddt, J=13.1, 6.2, 3.3 Hz, 1H), 1.90-2.03 (m, 2H), 1.56-1.70 (m, 2H), 1.38-1.56 (m, 2H), 1.25 (t, J=7.2 Hz, 3H), 0.89 (t, J=7.4 Hz, 3H)

Intermediate 13E: ethyl-2-((trans)-4-hydroxycyclohexyl)butanoate

Intermediate 13D (1.47 g, 6.92 mmol) was dissolved in EtOH (13.85 ml) and cooled to 0° C. NaBH$_4$ (0.314 g, 8.31 mmol) was added and the reaction was then allowed to stir at 0° C. for 1 hour. The reaction was quenched with saturated aqueous NH$_4$Cl and extracted with EtOAc. Combined organic extracts were dried with sodium sulfate, filtered, and concentrated in vacuo. The crude material was purified via silica gel column chromatography to give Intermediate 13E (1.22 g, 5.69 mmol, 82% yield) along with (138 mg, 0.644 mmol, 9.30% yield) of the cis-isomer. $^1$H NMR (400 MHz, CHLOROFORM-d) δ: 4.14 (q, J=7.1 Hz, 2H), 3.53 (t, J=10.5 Hz, 1H), 1.92-2.08 (m, 2H), 1.80-1.89 (m, 1H), 1.63-1.70 (m, 1H), 1.52-1.62 (m, 4H), 1.37-1.52 (m, 2H), 1.26 (t, J=7.2 Hz, 3H), 0.95-1.17 (m, 2H), 0.87 (t, J=7.4 Hz, 3H)

Intermediate 13F: ethyl 2-((trans)-4-(quinolin-4-yloxy)cyclohexyl)butanoate

Intermediate 13E (100 mg, 0.467 mmol) was taken up in DMSO (933 μl) and NaH (22.40 mg, 0.933 mmol) as added slowly, portionwise at room temperature over 1 minute. After 1 hour, 4-bromoquinoline (117 mg, 0.560 mmol) was added and the reaction was heated to 80° C. for 16 hours. The reaction was quenched with ammonium chloride and extracted with EtOAc. The combined organic extracts were dried with sodium sulfate, filtered, concentrated in vacuo. The crude residue was purified via silica gel column chromatography to give Intermediate 13F (89 mg, 0.261 mmol, 55.9% yield). LC-MS Anal. Calc'd for $C_{21}H_{27}NO_3$ 341.20, found [M+H] 342.3 $T_r$=0.84 min (Method A).

Intermediate 13G: 2-((trans)-4-(quinolin-4-yloxy)cyclohexyl)butanoic acid

Intermediate 13F (67 mg, 0.196 mmol) taken up in THF (157 μl), Water (157 μl), and MeOH (78 μl). Lithium hydroxide (47.0 mg, 1.962 mmol) added and reaction stirred at 60° C. overnight. The reaction was concentrated in vacuo, diluted with water and extracted with EtOAc. The aqueous was then treated with acetic acid and extracted with EtOAc followed by extraction with 7:3 chloroform:propanol. The combined organic extracts were dried with sodium sulfate, filtered, and concentrated in vacuo to give Intermediate 13G (58 mg, 0.185 mmol, 94% yield). Material used as is subsequently. LC-MS Anal. Calc'd for $C_{19}H_{23}NO_3$ 313.17, found [M+H] 314.3 $T_r$=0.69 min (Method A).

Example 13: 4-(((trans)-4-(1-(6-chloro-1H-benzo[d]imidazol-2-yl)propyl)cyclohexyl)oxy)quinoline Intermediate 13G (58 mg, 0.185 mmol) was dissolved in thionyl chloride (135 μl, 1.851 mmol) and DMF (7.17 μl, 0.093 mmol) was added. Reaction stirred at room temperature for 1 hour. Then, reaction concentrated in vacuo, taken up in toluene, concentrated again and placed on high vac. After 15 minutes, the crude acyl chloride was taken up in ACN (925 μl) and added to a solution of 4-chlorobenzene-1,2-diamine (52.8 mg, 0.370 mmol) in ACN (925 μl) and TEA (129 μl, 0.925 mmol) at ~45° C. The reaction was then allowed to warm to room temperature. After 15 the reaction was diluted with water and extracted with EtOAc. Crude residue was taken up in toluene (925 μl) and tosic acid (176 mg, 0.925 mmol) was added. Reaction refluxed for 16 hours. The reaction concentrated, taken up in 2 mL DMF, filtered and purified via preparative HPLC to give Example 13 (24.1 mg, 0.053 mmol, 29%). LC-MS Anal. Calc'd for $C_{25}H_{26}ClN_3O$ 419.18, found [M+H] 420.2 $T_r$=0.68 min (Method A). $^1$H NMR (500 MHz, DMSO-$d_6$) δ: 8.62 (d, J=5.1 Hz, 1H), 8.09 (d, J=8.3 Hz, 1H), 7.89 (d, J=8.4 Hz, 1H), 7.70 (t, J=7.5 Hz, 1H), 7.42-7.63 (m, 4H), 7.15 (d, J=7.9 Hz, 1H), 7.03 (d, J=5.2 Hz, 1H), 4.53 (br. s., 1H), 2.66 (br. s., 1H), 2.19 (br. s., 1H), 2.11 (d, J=10.1 Hz, 1H), 1.96-2.07 (m, 1H), 1.69-1.89 (m, 3H), 1.32-1.55 (m, 3H), 1.19 (d, J=11.4 Hz, 2H), 0.70 (t, J=7.2 Hz, 3H)

Example 13-1 (Enantiomer 1) and Example 13-2 (Enantiomer 2)

Enantiomer 1: Example 13-1, 4-(((trans)-4-(1-(6-chloro-1H-benzo[d]imidazol-2-yl)propyl)cyclohexyl)oxy)quinoline (Homochiral, Stereochemistry Undetermined)

Enantiomer 2: Example 13-2, 4-(((trans)-4-(1-(6-chloro-1H-benzo[d]imidazol-2-yl)propyl)cyclohexyl)oxy)quinoline (Homochiral, Stereochemistry undetermined)

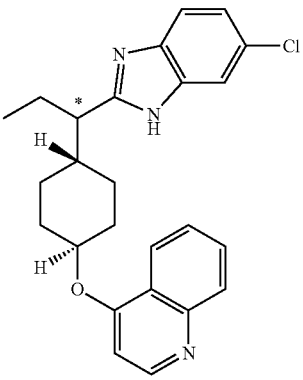 [SMILES: CCC(c1nc2ccc(Cl)cc2[nH]1)[C@H]1CC[C@H](Oc2ccnc3ccccc23)CC1]

Example 13-1 (Enantiomer 1) and Example 13-2 (Enantiomer 2): Chiral separation of the racemic sample (Method C) gave Enantiomer 1 $T_r$=12.052 min (Method D) and Enantiomer 2 $T_r$=14.206 min (Method D) Absolute stereochemistry was not determined.

Example 13-1, Enantiomer 1: MS (ES): m/z=420.3 [M+H]$^+$. $T_r$=1.995 min (Method B). $^1$H NMR (500 MHz, DMSO-$d_6$) δ: 8.63 (d, J=5.0 Hz, 1H), 8.09 (d, J=8.2 Hz, 1H), 7.90 (d, J=8.3 Hz, 1H), 7.70 (t, J=7.4 Hz, 1H), 7.42-7.62 (m, 3H), 7.15 (br. s., 1H), 7.04 (d, J=5.1 Hz, 1H), 4.54 (br. s., 1H), 2.67 (d, J=6.1 Hz, 1H), 2.21 (d, J=10.8 Hz, 1H), 2.13 (d, J=11.4 Hz, 1H), 2.01 (d, J=11.4 Hz, 1H), 1.70-1.88 (m, 3H), 1.37-1.58 (m, 3H), 1.11-1.28 (m, 3H), 0.72 (t, J=7.1 Hz, 3H)

Example 13-2, Enantiomer 2: MS (ES): m/z=420.2 [M+H]$^+$. $T_r$=1.963 min (Method B). $^1$H NMR (500 MHz, DMSO-$d_6$) δ: 8.63 (d, J=5.0 Hz, 1H), 8.09 (d, J=8.2 Hz, 1H), 7.90 (d, J=8.3 Hz, 1H), 7.70 (t, J=7.4 Hz, 1H), 7.40-7.62 (m, 3H), 7.15 (br. s., 1H), 7.04 (d, J=5.1 Hz, 1H), 4.54 (br. s., 1H), 2.67 (d, J=6.1 Hz, 1H), 2.21 (d, J=10.7 Hz, 1H), 2.12 (d, J=11.5 Hz, 1H), 2.01 (d, J=12.8 Hz, 1H), 1.69-1.88 (m, 3H), 1.34-1.57 (m, 3H), 1.11-1.28 (m, 3H), 0.72 (t, J=7.0 Hz, 3H)

Example 14: 4-(((cis)-4-(1-(6-chloro-1H-benzo[d]imidazol-2-yl)propyl)cyclohexyl) oxy)quinoline

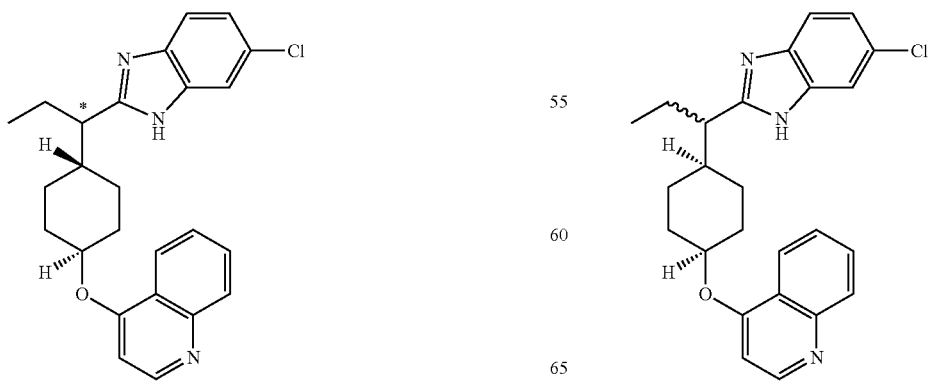

Intermediate 14A: ethyl 2-((cis)-4-(quinolin-4-yloxy)cyclohexyl)butanoate

Intermediate 13E (300 mg, 1.400 mmol) was dissolved in THF (5600 µl) and quinolin-4-ol (447 mg, 3.08 mmol) and triphenylphosphine (808 mg, 3.08 mmol) were added. Solution was cooled to 0° C. in an ice bath. Diisopropyl azodicarboxylate (599 µl, 3.08 mmol) was added and the reaction was allowed to stir at room temperature once the addition was complete. After 16 hours, the reaction was concentrated in vacuo and purified via silica gel column chromatography to give Intermediate 14A (411 mg, 0.782 mmol, 55.9% yield). LC-MS Anal. Calc'd for $C_{21}H_{27}NO_3$ 341.20, found [M+H] 342.3 $T_r$=0.81 min (Method A).

Intermediate 14B: 2-((cis)-4-(quinolin-4-yloxy)cyclohexyl)butanoic acid

Intermediate 14A (411 mg, 1.204 mmol) was taken up in THF (963 µl), water (963 µl), and MeOH (481 µl). Lithium hydroxide (288 mg, 12.04 mmol) added and reaction stirred at 60° C. overnight. After 16 hours, lithium hydroxide (288 mg, 12.04 mmol) was added and the reaction stirred another 24 hours at 60° C. The reaction was concentrated in vacuo, diluted with water and extracted with EtOAc. The aqueous was then treated with AcOH and extracted with EtOAc. It was also extracted again with 7:3 chloroform:propanol. The combined organic extracts were dried with sodium sulfate, filtered, and concentrated in vacuo to give Intermediate 25B (315 mg, 1.005 mmol, 84% yield). LC-MS Anal. Calc'd for $C_{19}H_{23}NO_3$ 313.17, found [M+H] 314.3 $T_r$=0.64 min (Method A).

Example 14: 4-(((cis)-4-(1-(6-chloro-1H-benzo[d]imidazol-2-yl)propyl)cyclohexyl) oxy)quinoline Intermediate 14B (75 mg, 0.239 mmol) was dissolved in thionyl chloride (175 µl, 2.393 mmol) and DMF (9.27 µl, 0.120 mmol) was added. Reaction stirred at room temperature. After 1 hour, the reaction was concentrated in vacuo, taken up in toluene, concentrated again and placed on high vac. After 15 minutes, the crude acyl chloride was taken up in ACN (1197 µl) and added to a solution of 4-chlorobenzene-1,2-diamine (68.2 mg, 0.479 mmol) in ACN (1197 µl) and TEA (167 µl, 1.197 mmol) at −45° C. The reaction was then allowed to warm to room temperature. After 15, the reaction was diluted with water and extracted with EtOAc. The crude residue was taken up in toluene (1197 µl) and tosic acid (228 mg, 1.197 mmol) was added. The reaction was reaction refluxed for 16 hours. It was then concentrated, taken up in 2 mL DMF, filtered and purified via preparative HPLC to give Example 14 (34.9 mg, 0.080 mmol, 33%). LC-MS Anal. Calc'd for $C_{25}H_{26}ClNO_3$ 419.18, found [M+H] 420.2 $T_r$=0.63 min (Method A). $^1$H NMR (500 MHz, DMSO-$d_6$) δ: 8.65 (d, J=5.1 Hz, 1H), 7.88 (d, J=8.4 Hz, 1H), 7.81 (d, J=8.2 Hz, 1H), 7.67 (t, J=7.6 Hz, 1H), 7.53 (br. s., 1H), 7.48 (d, J=7.9 Hz, 1H), 7.21 (t, J=7.5 Hz, 1H), 7.16 (d, J=8.5 Hz, 1H), 6.99 (d, J=5.2 Hz, 1H), 4.95 (br. s., 1H), 2.67-2.75 (m, 1H), 2.04 (d, J=14.6 Hz, 1H), 1.98 (d, J=13.6 Hz, 1H), 1.77-1.87 (m, 3H), 1.51-1.77 (m, 3H), 1.24-1.51 (m, 3H), 0.73 (t, J=7.2 Hz, 3H).

Example 15

Example 15, Enantiomers 1-4

4-(4-(1-(6-chloro-1H-benzo[d]imidazol-2-yl)propyl)cyclohexyl)-6-fluoroquinoline (All Four Isomers are Homochiral, Absolute Stereochemistry not Determined)

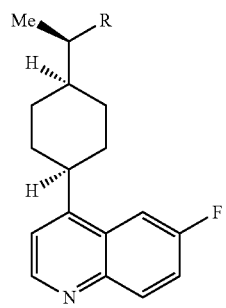

Intermediate 15A: ethyl 2-(1,4-dioxaspiro[4.5]decan-8-ylidene)acetate

In a 3 liter, 4 neck round bottom flask was taken sodium hydride (46.1 g, 1153 mmol) under nitrogen. To that THF (1200 mL) was added and cooled to 0° C. Triethyl phosphonoacetate (258 g, 1153 mmol) was added drop wise to it. The reaction was stirred at 0° C. for 30 minutes. Then 1,4-dioxaspiro[4.5]decan-8-one (150 g, 960 mmol) was added and the mixture was stirred at 0° C. for 2 hrs. Reaction mixture was warmed to room temperature and stirred for 16 hours. After 16 hours, the reaction mixture was quenched with water (500 ml) and the mixture was concentrated in vacuo. The residue was extracted with ethyl acetate (3×1000 ml). Combined organic layer was washed with water (500 ml) and brine (500 ml), dried over sodium sulphate, filtered, and concentrated. The crude material was purified through silica gel flash column chromatography (750 g column using 0 to 30% ethyl acetate in pet ether). The pure fractions were concentrated and dried over high vacuum pump to give Intermediate 1A (135 g, 597 mmol, 62%) H NMR (CHLOROFORM-d, 400 MHz) δ: 5.48 (br. s., 1H), 4.10-4.17 (m, 2H), 3.96-4.01 (m, 4H), 3.00 (s, 2H), 2.23-2.33 (m, 4H), 1.75-1.83 (m, 2H), 1.26 (t, J=7.1 Hz, 3H)

Intermediate 15B: ethyl 2-(1,4-dioxaspiro[4.5]decan-8-yl)acetate

To a 5 liter autoclave was taken Intermediate 1A (135 g, 597 mmol) and ethyl acetate (1500 mL). To that Pd/C (15.87 g, 149 mmol) was added and the reaction was flushed with nitrogen for 5 minutes. It was then stirred at room temperature under 3 kg/cm2 hydrogen gas pressure for 2 hours. After two hours, the reaction mixture was drained form autoclave and filtered through celite bed and celite bed was washed with ethyl acetate. The filtrate was concentrated to dryness to give Intermediate 1B (135 g, 591 mmol, 91%). $^1$H NMR (CHLOROFORM-d, 400 MHz) δ: 4.12 (q, J=7.4 Hz, 2H), 3.92-3.94 (m, 4H), 2.22 (d, J=7.0 Hz, 2H), 1.83 (td, J=7.2, 3.8 Hz, 1H), 1.69-1.78 (m, 4H), 1.51-1.60 (m, 2H), 1.28-1.36 (m, 2H), 1.23-1.27 (m, 3H)

Intermediate 15C: ethyl 2-(4-oxocyclohexyl)acetate

In a 10 liter reactor was taken Intermediate 1B (67.5 g, 296 mmol) in Acetone (5000 mL). To that HCl (1M) (1183 mL, 1183 mmol) was added and the reaction was heated to reflux for 2 hrs. After 2 hours, the reaction mixture was concentrated. The residue was then transferred to 10 liter separatory funnel and extracted with ethylacetate (3×1000 ml). The combined organic layers were washed with water (1000 ml) and brine (1000 ml), dried over sodium sulphate and concentrated in vacuo. The crude material was purified through silica gel flash column (750 g column using 0 to 20% ethyl acetate in petether) to give Intermediate 1C (40 g, 217 mmol, 73%). $^1$H NMR (CHLOROFORM-d, 400 MHz) d: 4.15 (q, J=7.0 Hz, 2H), 2.35-2.41 (m, 3H), 2.20-2.34 (m, 3H), 2.04-2.13 (m, 3H), 1.41-1.53 (m, 2H), 1.24-1.30 (t, 3H)

Intermediate 15D: ethyl 2-(4-(((trifluoromethyl) sulfonyl)oxy)cyclohex-3-en-1-yl)acetate In a 2 ltr 4 neck was taken 2,6-di-tert-butyl-4-methylpyridine (84 g, 407 mmol) in dichloromethane (500 mL) under nitrogen. To that triflic anhydride (55.0 mL, 326 mmol) was added drop wise. Then ethyl Intermediate 1C (50 g, 271 mmol) in dichloromethane (500 mL) was added slowly. After completion of addition, stirred at room temperature overnight. After stirring overnight, the reaction mixture was diluted with 1000 ml of dichloromethane and washed with water (500 ml) followed by sodium carbonate (500 ml) and then water once again (500 ml). The combined organic extracts were dried over sodium sulphate, filtered, and concentrated. The crude material was purified through flash silica gel column chromatography (750 g column using 0 to 10% ethyl acetate in pet ether) to give Intermediate 1D (65 g, 206 mmol, 76%). Pure fractions were concentrated. $^1$H NMR (CHLOROFORM-d, 400 MHz) δ: 5.73 (dt, J=4.9, 2.3 Hz, 1H), 4.15 (q, J=7.2 Hz, 2H), 2.28-2.52 (m, 5H), 2.07-2.21 (m, 1H), 1.89-2.00 (m, 2H), 1.54 (dt, J=6.0, 3.5 Hz, 1H), 1.25-1.30 (t, 3H)

Intermediate 15E: ethyl 2-(4-(4,4,5,5-tetramethyl-1, 3-dioxolan-2-yl)cyclohex-3-en-1-yl)acetate In 2 liter, 4 neck round bottom flask was taken Intermediate 1D (120 g, 379 mmol), bis(pinacolato)diboron (106 g, 417 mmol), and potassium acetate (112 g, 1138 mmol) in 1,4-Dioxane (1200 mL) under nitrogen. Nitrogen gas was then purged inside the reaction mixture for 10 minutes. Then 1,1'-bis(diphenylphosphino)ferrocene-palladium(II)dichloride dichloromethane complex (15.49 g, 18.97 mmol) was added and nitrogen gas was purged for 5 more minutes. The reaction was then heated to 80° C. for 16 hours under nitrogen atmosphere. The crude material was purified through flash column chromatography using 0 to 10% ethyl acetate in pet ether to give Intermediate 1E (56 g, 190 mmol, 50%). $^1$H NMR (CHLOROFORM-d, 400 MHz) δ: 6.46-6.55 (m, 1H), 4.12 (q, J=7.2 Hz, 2H), 1.99-2.35 (m, 6H), 1.68-1.87 (m, 2H), 1.17-1.34 (m, 16H).

Intermediate 15F: ethyl 2-(4-(6-fluoroquinolin-4-yl) cyclohex-3-en-1-yl)acetate Intermediate 15E (5 g, 17.00 mmol) was taken up in Dioxane (28.3 ml) and Water (7.08 ml), 4-chloro-6-fluoroquinoline (2.57 g, 14.15 mmol) was added followed by addition of potassium carbonate (5.87 g, 42.5 mmol). The mixture was bubbled with nitrogen gas for 5 minutes before addition of Pd(Ph$_3$P)$_4$ (0.327 g, 0.283 mmol). After addition, the reaction was bubbled with nitrogen gas for another five minutes and then sealed and heated to 100° C. for 16 hours. The reaction was then concentrated in vacuo and purified directly via column chromatography to give Intermediate 15F (4.22 g, 13.47 mmol, 95% yield). LC-MS Anal. Calc'd for C$_{19}$H$_{20}$FNO$_2$ 313.15, found [M+H] 314.1 T$_r$=0.75 min (Method A).

Intermediate 15G: ethyl 2-(4-(6-fluoroquinolin-4-yl) cyclohexyl)acetate (mixture of cis and trans diasteroemers)

Intermediate 15F (4.22 g, 13.47 mmol) was dissolved in methanol (67.3 ml) and ammonium formate (4.25 g, 67.3 mmol) was added. The vessel was equipped with a reflux condenser and vacated and flushed with nitrogen 3 times. Then, palladium on carbon (0.143 g, 1.347 mmol) (wet. Degussa type) was added and the reaction was heated to reflux for 1 hour. The reaction was cooled, concentrated in vacuo, and diluted with dichloromethane. The solids were filtered off and the filtrate was concentrated to give crude Intermediate 15G (4.20 g, 13.32 mmol, 99% yield) as a ~2:1 mixture of cis and trans diastereomers. LC-MS Anal. Calc'd for C$_{19}$H$_{22}$FNO$_2$ 315.16, found [M+H] 316.2 T$_r$=0.76 min (Method A).

Intermediate 15H: ethyl 2-(4-(6-fluoroquinolin-4-yl) cyclohexyl)butanoate (mixture of 4 diasteroemers)

To the flask containing THF (6 mL) was added lithium diisopropylamide (2.0 M solution in THF) (3.17 mL, 6.34 mmol) at −78° C., followed by addition of 1,3-dimethyltetrahydropyrimidin-2(1H)-one (0.573 mL, 4.76 mmol) and a solution of Intermediate 15G (1.0 g, 3.17 mmol) in THF (10 mL) dropwise at −78° C. The resulting mixture turned brown and was stirred at −78° C. for 1 h, then iodoethane (0.507 mL, 6.34 mmol) was added slowly (neat). The reaction mixture was then stirred at ice bath temperature for 1 hour followed by warming to room temperature over night. After 16 hours, the reaction was quenched by pouring into water and extracting with ethyl acetate. The combined organics were washed with brine, dried with sodium sulfate, filtered and concentrated in vacuo. The crude residue was purified by flash column chromatography to give Intermediate 15H (0.81 g, 2.36 mmol, 74% yield). LC-MS Anal. Calc'd for C$_{21}$H$_{26}$FNO$_2$ 343.20, found [M+H] 344.3 T$_r$=0.86 min (Method A).

Intermediate 15I: 2-(4-(6-fluoroquinolin-4-yl)cyclohexyl)butanoic acid (mixture of 4 diasteroemers)

To a solution of Intermediate 15H (0.81 g, 2.359 mmol) in tetrahydrofuran (4 mL) and methanol (7 mL) was added a solution of 2M lithium hydroxide (7.08 mL, 14.15 mmol) in water (4 mL) slowly. The reaction mixture was stirred at room temperature over night. To the reaction mixture was added more 2M lithium hydroxide (7.08 mL, 14.15 mmol) and the resulting reaction mixture was heated at 70° C. for 72 hours. The reaction mixture was cooled down and to the mixture was added ethyl acetate. The aqueous layer was separated and to the aqueous layer was added 1N HCl solution to adjust pH to 5-6. The resulting mixture was diluted with water and CHCl$_3$:2-propanol (2:1). The organic layer was separated and dried over MgSO$_4$. The filtrate was concentrated in vacuo to give Intermediate 15I (0.64 g, 2.029 mmol, 86% yield) as a white solid. LC-MS Anal. Calc'd for $C_{19}H_{22}FNO_2$ 315.16, found [M+H] 316.3 $T_r$=0.72 min (Method A).

Example 15: 4-(4-(1-(6-chloro-1H-benzo[d]imidazol-2-yl)propyl)cyclohexyl)-6-fluoroquinoline Intermediate 15I (76 mg, 0.241 mmol) was dissolved in thionyl chloride (176 μl, 2.410 mmol) and DMF (9.33 μl, 0.120 mmol) was added. Reaction stirred at room temperature. After 1 hour, the reaction was concentrated in vacuo, taken up in toluene, concentrated again and placed on high vac. After 15 minutes, the crude acyl chloride was taken up in acetonitrile (1205 μl) and added to a solution of 4-chlorobenzene-1,2-diamine (68.7 mg, 0.482 mmol) in acetonitrile (1205 μl) and triethylamine (168 μl, 1.205 mmol) at −45° C. Reaction was then allowed to warm to room temperature. After 30 min, the reaction was diluted with water and extracted with EtOAc. Organics were combined, dried with sodium sulfate, filtered and concentrated in vacuo.

The resulting crude residue was taken up in toluene (1205 μl) and tosic acid (229 mg, 1.205 mmol) was added. The reaction was heated to refluxed for 16 hours. The reaction was then concentrated, taken up in 2 mL DMF, filtered and purified via HPLC to give Example 15 as a mixture of four isomers (21 mg, 0.051 mmol, 21%). LC-MS Anal. Calc'd for $C_{25}H_{25}ClFN_3$ 421.17, found [M+H] 422.2 $T_r$=0.73 min (Method A).

Enantiomers 1-4

4-(4-(1-(6-chloro-1H-benzo[d]imidazol-2-yl)propyl)cyclohexyl)-6-fluoroquinoline (All Four Isomers are Homochiral, Absolute Stereochemistry not Determined)

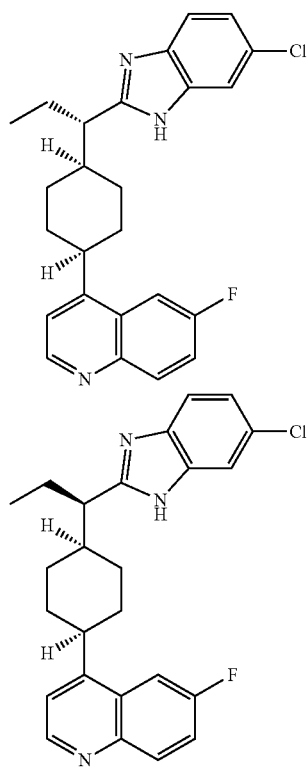

-continued

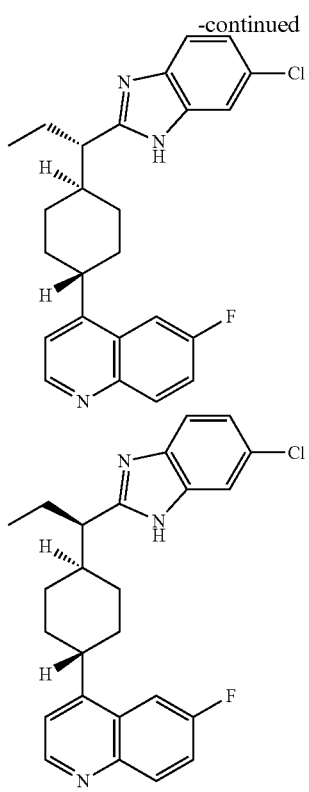

Example 15, Enantiomer 1, Enantiomer 2, Enantiomer 3, and Enantiomer 4: Chiral separation of the racemic sample (Method G) gave Example 15-1, Enantiomer 1 $T_r$=4.905 min (Method H) and Example 15-2, Enantiomer 2 $T_r$=7.483 min and Example 15-3, Enantiomer 3 $T_r$=9.256 min (Method H) and Example 15-4, Enantiomer 4 $T_r$=11.884 min (Method H) (Absolute stereochemistry was not determined).

Example 51-1, Enantiomer 1: MS (ES): m/z=422.1 [M+H]$^+$. $T_r$=2.044 min (Method B). $^1$H NMR (500 MHz, DMSO-$d_6$) δ: 8.85 (d, J=4.3 Hz, 1H), 8.09 (dd, J=9.1, 5.9 Hz, 1H), 7.96 (d, J=8.7 Hz, 1H), 7.62-7.69 (m, 1H), 7.56-7.62 (m, 2H), 7.53 (d, J=8.5 Hz, 1H), 7.19 (d, J=8.1 Hz, 1H), 3.32-3.45 (m, 1H), 3.24 (td, J=10.9, 3.2 Hz, 1H), 2.18 (d, J=9.2 Hz, 1H), 1.99-2.07 (m, 1H), 1.58-1.99 (m, 7H), 1.52 (d, J=11.3 Hz, 1H), 1.05 (d, J=12.1 Hz, 1H), 0.69 (t, J=7.2 Hz, 3H)

Example 15-2, Enantiomer 2: MS (ES): m/z=422.2 [M+H]$^+$. $T_r$=2.022 min (Method B). $^1$H NMR (500 MHz, DMSO-$d_6$) δ: 8.77 (d, J=4.4 Hz, 1H), 8.05 (dd, J=9.1, 5.8 Hz, 1H), 7.92 (dd, J=10.9, 2.1 Hz, 1H), 7.63 (td, J=8.6, 2.4 Hz, 1H), 7.55 (s, 1H), 7.50 (d, J=8.4 Hz, 1H), 7.41 (d, J=4.5 Hz, 1H), 7.15 (d, J=8.5 Hz, 1H), 3.22 (t, J=11.5 Hz, 1H), 2.64-2.71 (m, 1H), 2.05 (d, J=10.9 Hz, 1H), 1.74-1.96 (m, 5H), 1.40-1.60 (m, 3H), 1.27-1.38 (m, 2H), 0.73 (t, J=7.2 Hz, 3H)

Example 15-3, Enantiomer 3: MS (ES): m/z=422.3 [M+H]$^+$. $T_r$=2.075 min (Method B). $^1$H NMR (500 MHz, DMSO-$d_6$) δ: 8.83 (d, J=4.2 Hz, 1H), 8.08 (dd, J=8.9, 5.9 Hz, 1H), 7.94 (d, J=9.2 Hz, 1H), 7.64 (t, J=7.4 Hz, 1H), 7.40-7.59 (m, J=4.2 Hz, 3H), 7.14 (d, J=8.1 Hz, 1H), 3.37 (br. s., 1H), 3.14-3.24 (m, 1H), 2.17 (br. s., 1H), 2.02 (d, J=13.1 Hz, 1H), 1.55-1.97 (m, 7H), 1.51 (d, J=12.3 Hz, 1H), 1.06 (d, J=13.9 Hz, 1H), 0.68 (t, J=7.1 Hz, 3H)

Example 15-4, Enantiomer 4: MS (ES): m/z=422.1 [M+H]$^+$. $T_r$=2.022 min (Method B). $^1$H NMR (500 MHz, DMSO-d$_6$) δ: 8.77 (d, J=4.5 Hz, 1H), 8.05 (dd, J=9.0, 5.8 Hz, 1H), 7.91 (d, J=10.9 Hz, 1H), 7.37-7.67 (m, 4H), 7.09-7.20 (m, 1H), 3.17-3.25 (m, 1H), 2.68 (br. s., 1H), 1.99-2.10 (m, 1H), 1.72-1.97 (m, 5H), 1.40-1.61 (m, 3H), 1.24-1.40 (m, 2H), 0.73 (t, J=7.2 Hz, 3H)

Example 16

Diastereomers 1 and 2

(±)-4-(4-(1-(6-chloro-1H-benzo[d]imidazol-2-yl) ethyl)cyclohexyl)quinoline (each cis- or trans-diasteromer is racemic; cis- and trans- are arbitrarily assigned)

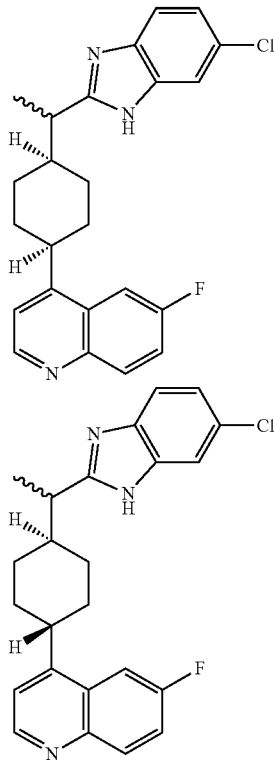

Intermediate 16A: ethyl 2-(4-(quinolin-4-yl)cyclohex-3-en-1-yl)acetate

Intermediate 15E (6.22 g, 21.15 mmol) was taken up in Dioxane (38.5 ml) and Water (9.61 ml), 4-bromoquinoline (4 g, 19.23 mmol) was added followed by potassium carbonate (7.97 g, 57.7 mmol). The mixture was bubbled with nitrogen gas for 5 minutes before addition of Pd(Ph$_3$P)$_4$ (0.444 g, 0.385 mmol). After addition, reaction was vacated and backfilled with nitrogen gas three times and then sealed and heated to 100° C. for 16 hours. The reaction concentrated in vacuo and purified directly via silica gel column chromatography to give Intermediate 16A (3.29 g, 11.14 mmol, 57.9% yield). LC-MS Anal. Calc'd for C$_{19}$H$_{21}$NO$_2$ 295.16, found [M+H] 296.2, T$_r$=0.71 min (Method A).

Intermediate 16B: ethyl 2-(4-(quinolin-4-yl)cyclohexyl)acetate

Intermediate 16A (3.29 g, 11.14 mmol) was dissolved in methanol (55.7 ml) and ammonium formate (3.51 g, 55.7 mmol) was added. The vessel was equipped with a reflux condenser and vacated and flushed with nitrogen gas three times. Then, palladium on carbon (0.119 g, 1.114 mmol) (wet 51% by weight, degussa type) was added and the reaction was heated to reflux for 1 hour. The reaction was cooled, concentrated in vacuo, and diluted with dichloromethane. Solids were filtered off and the filtrate was concentrated to give crude Intermediate 16B (2.99 g, 10.05 mmol, 90% yield). LC-MS Anal. Calc'd for C$_{19}$H$_{23}$NO$_2$ 297.17, found [M+H] 298.2. T$_r$=0.71 min (Method A).

Intermediate 16C: ethyl 2-(4-(quinolin-4-yl)cyclohexyl)propanoate

Diisopropylamine (3.12 ml, 22.12 mmol) was taken up in dry THF (12.57 ml) under a nitrogen atmosphere and cooled to −78° C. nBuLi (8.45 ml, 21.11 mmol) (2.5 M in hexanes) was added over ~5 minutes at −78° C. After stirring for 30 minutes, reaction was warmed to room temperature for 10 minutes and returned to −78° C. Then, 1,3-dimethyltetrahydropyrimidin-2(1H)-one (1.211 ml, 10.05 mmol) was added followed by a solution of Intermediate 16B (2.99 g, 10.05 mmol) in THF (12.57 ml) (dropwise over ~5 minutes at −78 C) (Reaction turns orange). After 10 minutes, iodomethane (1.565 ml, 25.1 mmol) (neat) was added, 1 hour after the addition was complete, the reaction was allowed to warm to room temperature and stirred overnight at room temperature. The reaction was quenched with ammonium chloride (saturated aqueous solution) and water. It was then extracted with Ethyl acetate. The combined organics were dried with sodium sulfate, filtered, and concentrated in vacuo. The crude residue was purified via silica gel column chromatography to give Intermediate 16C (2.42 g, 5.44 mmol, 54.1% yield) which was contaminated with a small amount of 16B. Carried forward without further purification. LC-MS Anal. Calc'd for C$_{20}$H$_{25}$NO$_2$ 311.19, found [M+H] 312.2, T$_r$=0.74 min (Method A).

Intermediate 16D: 2-(4-(quinolin-4-yl)cyclohexyl)propanoic acid

Intermediate 16C (2.42 g, 7.77 mmol) taken up in THF (6.22 ml), Water (6.22 ml), and MeOH (3.11 ml). Lithium hydroxide (1.861 g, 78 mmol) added and reaction stirred at room temperature for 2 hours. It was then stirred at 50° C. overnight. After 16 hours, the reaction was concentrated in vacuo, diluted with water, treated with AcOH and extracted with EtOAc. The aqueous layers was then extracted again with 7:3 chloroform:propanol. The combined organics were dried with sodium sulfate, filtered, concentrated in vacuo, and placed on a vacuum overnight (to remove remaining AcOH) to give Intermediate 16D (2.10 g, 7.41 mmol, 95% yield). LC-MS Anal. Calc'd for C$_{18}$H$_{21}$NO$_2$ 283.16, found [M+H] 284.2, T$_r$=0.60 min (Method A).

Example 16 Diastereomers 1 and 2

(±)-4-(4-(1-(6-chloro-1H-benzo[d]imidazol-2-yl) ethyl)cyclohexyl)quinoline (each cis- or Trans-Diasteromer is Racemic; Cis- and Trans- are Arbitrarily Assigned)

Intermediate 16D (100 mg, 0.353 mmol) was dissolved in thionyl chloride (258 μl, 3.53 mmol) and DMF (13.66 μl, 0.176 mmol) was added. Reaction stirred at room temperature. After 1 hour, the reaction was concentrated in vacuo, taken up in toluene, concentrated again and placed on a vacuum line to remove excess solvent and reagent. After 15 minutes, the crude acyl chloride was taken up in acetonitrile (1765 µl) and added to a solution of 4-chlorobenzene-1,2-diamine (101 mg, 0.706 mmol) in acetonitrile (1765 µl) and triethylamine (246 µl, 1.765 mmol) at 0° C. Reaction was then allowed to warm to room temperature and stirred at room temperature overnight. After 16 hours, the reaction was diluted with water and extracted with EtOAc. The organics extracts were combined, dried with sodium sulfate, filtered and concentrated in vacuo. The crude residue was taken up in toluene (1765 µl) and tosic acid (336 mg, 1.765 mmol) was added. The reaction was refluxed for 16 hours. After 16 hours, the reaction was concentrated, taken up in 2 mL DMF, filtered and a small portion of the material was purified via HPLC to give Example 16 diastereomers 1 and 2

Example 16-1, Diastereomer 1: LC-MS Anal. Calc'd for $C_{24}H_{24}ClN_3$ 389.17, found [M+H] 390.3, $T_r$=1.841 min (Method B). $^1$H NMR (500 MHz, DMSO-$d_6$) δ: 8.79 (d, J=4.5 Hz, 1H), 8.18 (d, J=8.5 Hz, 1H), 8.00 (d, J=8.3 Hz, 1H), 7.72 (t, J=7.6 Hz, 1H), 7.59 (t, J=7.5 Hz, 2H), 7.42-7.55 (m, 1H), 7.38 (d, J=4.5 Hz, 1H), 7.10-7.19 (m, 1H), 3.32 (br. s., 1H), 2.91 (t, J=7.0 Hz, 1H), 1.96 (t, J=12.0 Hz, 2H), 1.76-1.92 (m, 3H), 1.46-1.63 (m, 3H), 1.29-1.43 (m, 4H)

Example 16-2, Diastereomer 2: LC-MS Anal. Calc'd for $C_{24}H_{24}ClN_3$ 389.17. found [M+H] 390.2, $T_r$=1.872 min (Method B). $^1$H NMR (500 MHz, DMSO-$d_6$) δ: 8.86 (d, J=4.4 Hz, 1H), 8.21 (d, J=8.5 Hz, 1H), 8.02 (d, J=8.3 Hz, 1H), 7.74 (t, J=7.5 Hz, 1H), 7.61 (t. J=7.5 Hz, 1H), 7.53 (d, J=4.3 Hz, 2H), 7.49 (br. s., 1H), 7.14 (d, J=8.2 Hz, 1H), 3.32-3.52 (m, 1H), 2.12 (br. s., 1H), 2.04 (d, J=12.0 Hz, 1H), 1.65-1.98 (m, 5H), 1.50-1.65 (m, 2H), 1.33 (d, J=6.8 Hz, 3H), 1.15 (d, J=12.6 Hz, 1H)

Example 17

Diastereomers 1 and 2

(±)-4-(4-(1-(6-chloro-1H-benzo[d]imidazol-2-yl)-3-propyl)cyclohexyl)-6-(trifluoromethyl)quinoline (relative stereochemistry not determined)

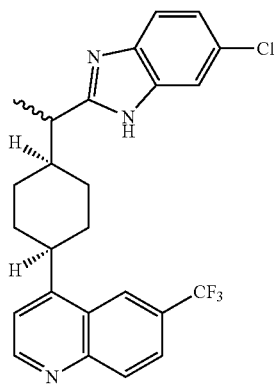

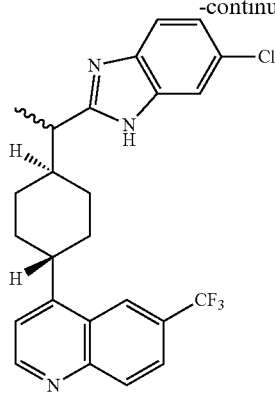

Intermediate 17A: ethyl 2-(4-(6-(trifluoromethyl)quinolin-4-yl)cyclohex-3-en-1-yl)acetate To a solution of 4-chloro-6-(trifluoromethyl)quinoline (2.05 g, 8.85 mmol) and Intermediate 15E (3.12 g, 10.62 mmol) in 1,4-Dioxane (35 mL) was added potassium carbonate (3.67 g, 26.6 mmol) and Water (7 mL). The reaction mixture was purged with a nitrogen stream for three minutes, followed by addition of Pd(Ph$_3$P)$_4$ (0.409 g, 0.354 mmol). The resulting mixture purged with nitrogen once again, sealed, and was heated at 100° C. under nitrogen stream for 16 hours. The reaction mixture was cooled down and diluted with ethyl acetate and saturated aqueous NaHCO$_3$ solution. The organic layer was separated and washed with saturated aqueous NaHCO$_3$ solution, dried over MgSO$_4$, filtered, and concentrated in vacuo. The resulting residue was purified via silica gel column chromatography to give Intermediate 17A (3.0 g, 8.26 mmol, 93%). LC-MS Anal. Calc'd for $C_{20}H_{20}F_3NO_2$ 363.15, found [M+H] 364.5, $T_r$=0.97 min (Method A).

Intermediate 17B: ethyl 2-(4-(6-(trifluoromethyl)quinolin-4-yl)cyclohexyl)acetate Intermediate 17A (3.0 g, 8.26 mmol) was added to a mixture of ammonium formate (2.082 g, 33.0 mmol) in MeOH (50 mL) and this mixture was purged with nitrogen stream for 3 min, followed by addition of 10% palladium on carbon (0.879 g, 0.413 mmol) (wet, Degussa type). The resulting mixture was refluxed at 85° C. for 2 h. The reaction mixture was then cooled and diluted with dichloromethane. The reaction mixture was filtered over celite and the filter cake was washed with dichloromethane. The filtrate was concentrated in vacuo. The residue was extracted with ethyl acetate and washed with saturated NaHCO$_3$ solution, brine successively. The organic layer was dried over MgSO$_4$ and the filtrate was concentrated in vacuo to give Intermediate 17B (2.6 grams, 7.12 mmol, 86%) as a mixture of cis- and trans-diastereomers. LC-MS Anal. Calc'd for $C_{20}H_{22}F_3NO_2$ 365.16, found [M+H] 366.2, $T_r$=0.94 min (Method A).

Intermediate 17C: ethyl 2-(4-(6-(trifluoromethyl)quinolin-4-yl)cyclohexyl)butanoate To the flask containing THF (15 mL) was added lithium diisopropylamide (2.0 M solution in THF) (7.65 mL, 15.30 mmol) at −78° C., followed by addition of 1,3-dimethyltetrahydropyrimidin-2(1H)-one (1.287 mL, 10.67 mmol) and a solution of ethyl 2-(4-(6-(trifluoromethyl)quinolin-4-yl)cyclohexyl)acetate (2.6 g, 7.12 mmol) in THF (10 mL) dropwise at −78° C. The resulting mixture turned into brown and stirred at −78° C. for 1 hour, then iodoethane (1.138 mL, 14.23 mmol) was added slowly. The reaction mixture was warmed to room temperature and stirred for 3 hours. The reaction was quenched by pouring into water and extracting with EtOAc. Combined organics was washed with brine, dried with MgSO$_4$, filtered and concentrated in vacuo. The resulting material was purified via silica gel column chromatography to give Intermediate 17C (1.1 g, 2.77 mmol, 39%). LC-MS Anal. Calc'd for $C_{22}H_{26}F_3NO_2$ 393.19, found [M+H] 394.3. $T_r$=0.97 min (Method A).

Intermediate 17D: 2-(4-(6-(trifluoromethyl)quinolin-4-yl)cyclohexyl)butanoic acid To a mixture of Intermediate 17C (1.1 g, 2.80 mmol) in THF (20 mL) and MeOH (8 mL) was added lithium hydroxide (2.0 M solution) (13.98 mL, 28.0 mmol). The resulting mixture was heated at 65° C. for 72 hours. The reaction mixture was cooled down and diluted with water. To the mixture was added 1 N HCl solution to adjust pH to about 5. White solid crashed out at pH 5-6. The resulting mixture was extracted with ethyl acetate twice. The organic layer was separated and washed with brine, dried over MgSO$_4$. The filtrate was concentrated in vacuo to give Intermediate 17D (0.93 grams, 2.55 mmol, 91%) as a pale yellow solid. LC-MS Anal. Calc'd for $C_{20}H_{22}F_3NO_2$ 365.16, found [M+H] 366.3, $T_r$=0.97 min (Method A).

Example 17: Enantiomers 1 and 2 4-(4-(1-(6-chloro-1H-benzo[d]imidazol-2-yl)-3-propyl)cyclohexyl)-6-(trifluoromethyl)quinoline (Both Isomers are Racemic with Cis- or Trans-Stereochemistry Across the Cyclohexyl Ring, Absolute Stereochemistry not Determined)

Intermediate 17D (40 mg, 0.109 mmol) was dissolved in thionyl chloride (80 µl, 1.095 mmol) and DMF (4.24 µl, 0.055 mmol) was added. Reaction stirred at room temperature. After 1 hour, reaction concentrated in vacuo, taken up in toluene, concentrated again and placed on high vacuum to remove excess thionyl chloride. After 15 minutes, the crude acyl chloride was taken up in ACN (547 µl) and added to a solution of 4-chlorobenzene-1,2-diamine (31.2 mg, 0.219 mmol) in ACN (547 µl) and TEA (76 µl, 0.547 mmol) at 0° C. Reaction was then allowed to warm to room temperature and stirred overnight. After 16 hours, the reaction was diluted with water and extracted with EtOAc. Organics were combined, dried with sodium sulfate, filtered and concentrated in vacuo. The crude residue was taken up in toluene (547 µl) and tosic acid (104 mg, 0.547 mmol) was added. The reaction was refluxed for 16 hours. The reaction was then concentrated, taken up in 2 mL DMF, filtered and purified via HPLC to give cis- and trans- Example 17.

Example 17-1, Diastereomer 1: (5.6 mg, 0.012 mmol, 11%) LC-MS Anal. Calc'd for $C_{26}H_{25}ClF_3N_3$ 471.17, found [M+H] 472.1, $T_r$=2.178 min (Method B). $^1$H NMR (500 MHz, DMSO-d$_6$) δ: 8.98 (d, J=4.6 Hz, 1H), 8.53 (s, 1H), 8.22 (d, J=8.8 Hz, 1H), 8.00 (d, J=8.7 Hz, 1H), 7.88 (s, 1H), 7.79 (d, J=8.8 Hz, 1H), 7.56 (d, J=4.6 Hz, 1H), 7.52 (d, J=8.6 Hz, 1H), 3.43-3.53 (m, 1H), 3.02 (br. s., 1H), 1.79-2.11 (m, 6H), 1.46-1.68 (m, 3H), 1.29-1.44 (m, 2H), 0.79 (t, J=7.2 Hz, 3H)

Example 17-2, Diastereomer 2: (16.6 mg, 0.035 mmol, 32%) LC-MS Anal. Calc'd for $C_{26}H_{25}ClF_3N_3$ 471.17, found [M+H] 472.4, $T_r$=2.206 min (Method B). $^1$H NMR (500 MHz, DMSO-d$_6$) δ: 9.04 (d, J=4.5 Hz, 1H), 8.59 (s, 1H), 8.25 (d, J=8.7 Hz, 1H), 8.02 (d, J=8.8 Hz, 1H), 7.89 (s, 1H), 7.80 (d, J=8.7 Hz, 1H), 7.75 (d, J=4.5 Hz, 1H), 7.46-7.56 (m, 1H), 3.45-3.73 (m, 2H), 2.28 (d, J=8.9 Hz, 1H), 2.07 (d, J=12.1 Hz, 2H), 1.67-2.00 (m, 6H), 1.56 (d, J=11.1 Hz, 1H), 1.03 (d, J=13.1 Hz, 1H), 0.75 (t, J=7.2 Hz, 3H)

Example 18

(±)-4-((cis)-4-(1-(6-chloro-1H-benzo[d]imidazol-2-yl)-2-methoxyethyl)cyclohexyl)-6-(trifluoromethyl)quinoline

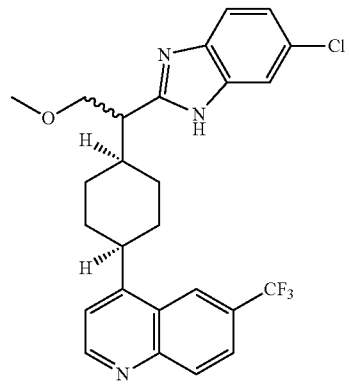 [SMILES: COCC(c1nc2ccc(Cl)cc2[nH]1)[C@H]1CC[C@@H](c2ccnc3ccc(C(F)(F)F)cc32)CC1]

Intermediate 18A: ethyl 3-methoxy-2-((cis)-4-(6-(trifluoromethyl)quinolin-4-yl)cyclohexyl)propanoate To the flask containing THF (10 mL) was added lithium diisopropylamide (1.5 M solution in hexane) (3.65 mL, 5.47 mmol) at −78° C., followed by addition of 1,3-dimethyltetrahydropyrimidin-2(1H)-one (0.3% mL, 3.28 mmol) and a solution of Intermediate 17B (0.8 g, 2.189 mmol) in THF (5 mL) dropwise at −78° C. The resulting mixture turned brown and stirred at −78° C. for 1 hour, then chloromethyl methylether (0.249 mL, 3.28 mmol) (neat) was added slowly. The reaction mixture was stirred at −78° C. for 2 hours, then the bath removed and stirred for 20 hours at room temperature. After 20 hours, the reaction mixture was quenched with water and the resulting mixture was extracted with ethyl acetate. The organic layer was separated and washed with brine, dried over MgSO$_4$ and filtered. The filtrate was concentrated in vacuo. The residue was dissolved in DCM, purified by silica gel column chromatography to give Intermediate 18A (0.39 g, 0.952 mmol, 44%). LC-MS Anal. Calc'd for $C_{22}H_{26}F_3NO_3$ 409.19, found [M+H] 410.2, $T_r$=0.91 min (Method A).

Intermediate 18B: 3-methoxy-2-((cis)-4-(6-(trifluoromethyl)quinolin-4-yl)cyclohexyl)propanoic acid To a solution of Intermediate 18A (0.49 g, 1.197 mmol) in THF (6 mL) and MeOH (6 mL) was added lithium hydroxide (2.0 M solution) (7.18 mL, 14.36 mmol). The reaction mixture was heated at 70° C. for 5 h. The reaction mixture was then cooled down and to the mixture was added water and 1 N HCl to adjust pH ~6 and 2 mL of acetic acid to pH~4. White solid precipitated out and the resulting suspension was extracted with ethyl acetate. The organic layer was separated, dried over MgSO$_4$, and filtered. The filtrate was concentrated in vacuo and the crude product was purified via HPLC to give Intermediate 18B (0.38 g, 0.996 mmol, 83%) as a yellow solid. LC-MS Anal. Calc'd for C$_{20}$H$_{22}$F$_3$NO$_3$ 381.13, found [M+H]382.2, T$_r$=0.74 min (Method A).

Example 18: (±)-4-((cis)-4-(1-(6-chloro-1H-benzo [d]imidazol-2-yl)-2-methoxyethyl)cyclohexyl)-6-(trifluoromethyl)quinoline Intermediate 18B (27 mg, 0.071 mmol) was dissolved in thionyl chloride (51.7 µl, 0.708 mmol) and DMF (2.74 µl, 0.035 mmol) was added. Reaction stirred at room temperature. After 1 hour, the reaction was concentrated in vacuo, taken up in toluene, concentrated again and placed on high vacuum to remove additional thionyl chloride. After 15 minutes, the crude acyl chloride was taken up in ACN (177 µl) and added to a solution of 4-chlorobenzene-1,2-diamine (20.19 mg, 0.142 mmol) in ACN (177 µl) and TEA (49.3 µl, 0.354 mmol) at 0° C. Reaction was then allowed to warm to room temperature. After 1 hour, LCMS shows conversion to peak with M+1 of desired intermediate. Reaction diluted with water and extracted with EtOAc. Organics were combined, dried with sodium sulfate, filtered and concentrated in vacuo. The crude intermediate was taken up in POCl$_3$ (330 µl, 3.54 mmol) and heated to 90° C. for 1 hour. Reaction quenched by adding slowly to 1N NaOH and basifying until pH~10. The resulting aqueous suspension was extracted with EtOAc. Organics dried with sodium sulfate, filtered, and concentrated in vacuo. The crude product was taken up in DMF, filtered, and purified via HPLC to give Example 18 (8.4 mg, 0.017 mmol, 24% yield). LC-MS Anal. Calc'd for C$_{26}$H$_{25}$ClF$_3$N$_3$O 487.16, found [M+H] 488.1, T$_r$=0.86 min (Method A). $^1$H NMR (500 MHz, DMSO-d$_6$) δ: 12.38-12.48 (m, 1H), 9.04 (d, J=4.5 Hz, 1H), 8.56 (s, 1H), 8.23 (d, J=8.8 Hz, 1H), 8.00 (d, J=8.8 Hz, 1H), 7.72 (d, J=4.5 Hz, 1H), 7.41-7.62 (m, 2H), 7.14 (ddd, J=10.8, 8.8, 1.7 Hz, 1H), 3.71-3.80 (m, 2H), 3.56-3.65 (m, 2H), 3.35 (br. s., 1H), 3.20 (s, 3H), 2.25 (d, J=10.8 Hz, 1H), 1.72-2.03 (m, 5H), 1.64 (t, J=13.1 Hz, 1H), 1.54 (d, J=12.4 Hz, 1H), 1.10 (d, J=13.1 Hz, 1H)

Example 19

(±)-4-((cis)-4-(1-(6-chloro-1H-benzo[d]imidazol-2-yl)-2-methoxyethyl)cyclohexyl)-6-fluoroquinoline

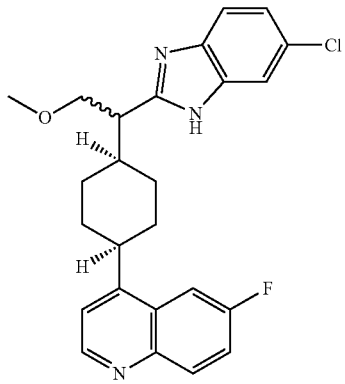 [SMILES: COCC(c1nc2ccc(Cl)cc2[nH]1)[C@H]1CC[C@@H](c2ccnc3ccc(F)cc32)CC1]

Intermediate 19A: ethyl 2-(4-(6-fluoroquinolin-4-yl) cyclohex-3-en-1-yl)-3-methoxypropanoate To the flask containing THF (8 mL) was added lithium diisopropylamide (1.5 M solution in hexane) (4.89 mL, 7.34 mmol) at −78° C. followed by addition of 1,3-dimethyltetrahydropyrimidin-2(1H)-one (0.539 mL, 4.47 mmol) and a solution of Intermediate 15G (1.0 g, 3.19 mmol) in THF (3 mL) dropwise at −78° C. The resulting mixture turned green and was stirred at −78° C. for 1 hour. Then chloromethyl methylether (0.388 mL, 5.11 mmol) (neat) was added slowly. The reaction mixture was stirred at −78° C. for 0.5 hours, then warmed up to about −20° C. for 4 h, then warmed to room temperature over night. The reaction mixture was quenched with water and the resulting mixture was extracted with ethyl acetate. The organic layer was separated and washed with brine, dried over MgSO$_4$, and filtered. The filtrate was concentrated in vacuo. The residue was dissolved in DCM, purified by silica gel column chromatography to give Intermediate 19A (0.80 g, 2.24 mmol, 70%). LC-MS Anal. Calc'd for C$_{21}$H$_{24}$FNO$_3$ 357.17, found [M+H] 358.2, T$_r$=0.78 min (Method A).

Intermediate 19B: ethyl 2-((cis)-4-(6-fluoroquinolin-4-yl)cyclohexyl)-3-methoxypropanoate To a solution of Intermediate 19A (1.08 g, 3.02 mmol) in methanol (20 mL) was added 10% palladium on carbon (0.643 g, 0.302 mmol). The reaction mixture was evacuated and then filled with hydrogen, evacuated again and back filled again with hydrogen. Reaction stirred under hydrogen using a hydrogen balloon at room temperature overnight. The reaction mixture was filtered through a celite pad and the pad was washed with ethyl acetate and MeOH. The filtrate was concentrated in vacuo. The residue was purified via supercritical fluid chromatography to separate cis- and trans-diastereomers to give Intermediate 19B (0.44 g, 1.224 mmol, 41% yield). LC-MS Anal. Calc'd for C$_{21}$H$_{26}$FNO$_3$ 359.19, found [M+H] 360.2, T$_r$=0.74 min (Method A).

Intermediate 19C: 2-((cis)-4-(6-fluoroquinolin-4-yl) cyclohexyl)-3-methoxypropanoic acid To a solution of Intermediate 19B (0.44 g, 1.224 mmol) in THF (5 mL) and MeOH (5 mL) was added lithium hydroxide (2.0 m solution) (3.67 mL, 7.34 mmol). The reaction mixture was stirred at room temperature over night. After ~16 hours, to the reaction mixture was added more MeOH (5 mL) (2 mL) and lithium hydroxide (2.0 m solution) (3.67 mL, 7.34 mmol) (4 mL) and the reaction mixture was heated at 65° C. for 6 hours, then stirred at 40° C. for 2 days. The reaction mixture was cooled down and diluted with water and 1 N HCl solution was added to adjust pH to 4-5. The resulting mixture was extracted with ethyl acetate twice. The organic layer was separated, dried over MgSO$_4$, and filtered. The filtrate was concentrated in vacuo to give brown oil. The crude residue was purified via HPLC to give Intermediate 19C (0.38, 1.15 mmol, 94% yield). LC-MS Anal. Calc'd for C$_{19}$H$_{22}$FNO$_3$ 331.16, found [M+H] 332.2, T$_r$=0.62 min (Method A).

Example 19: (±)-4-((cis)-4-(1-(6-chloro-1H-benzo [d]imidazol-2-yl)-2-methoxyethyl)cyclohexyl)-6-fluoroquinoline Intermediate 19C (35 mg, 0.106 mmol) was dissolved in thionyl chloride (77 µl, 1.056 mmol) and DMF (4.09 µl, 0.053 mmol) was added. Reaction stirred at room temperature. After 1 hour, the reaction was concentrated in vacuo, taken up in toluene, concentrated again and placed on high vacuum to remove more thionyl chloride. After 15 minutes, the crude acyl chloride was taken up in ACN (264 μl) and added to a solution of 4-chlorobenzene-1,2-diamine (30.1 mg, 0.211 mmol) in ACN (264 μl) and TEA (73.6 μl, 0.528 mmol) at 0° C. Reaction was then allowed to warm to room temperature. After 1 hour, the reaction was diluted with water and extracted with EtOAc. Organics were combined, dried with sodium sulfate, filtered and concentrated in vacuo. The crude intermediate was taken up in POCl$_3$ (492 μl, 5.28 mmol) and heated to 90° C. for 1 hour. The reaction was then quenched by adding slowly to 1N NaOH and basifying until pH~10. The resulting mixture was extracted with EtOAc. The combined organics were dried with sodium sulfate, filtered, and concentrated in vacuo. The crude residue was taken up in DMF, filtered, and purified via HPLC to give Example 19 (10.6 mg, 0.024 mmol, 22%). LC-MS Anal. Calc'd for $C_{25}H_{25}ClFN_3O$ 437.17, found [M+H] 438.1. $T_r$=0.75 min (Method A). $^1$H NMR (500 MHz, DMSO-d$_6$) δ: 8.86 (d, J=4.5 Hz, 1H), 8.09 (dd, J=9.2, 5.8 Hz, 1H), 7.97 (dd, J=10.9, 2.4 Hz, 1H), 7.66 (td, J=8.6, 2.7 Hz, 1H), 7.40-7.61 (m, 3H), 7.14 (d, J=8.6 Hz, 1H), 3.71-3.79 (m, 2H), 3.59 (br. s., 1H), 3.37 (br. s., 1H), 3.20 (s, 3H), 2.20-2.30 (m, 1H), 1.69-2.02 (m, 5H), 1.62 (t, J=13.2 Hz, 1H), 1.53 (d, J=13.5 Hz, 1H), 1.09 (d, J=13.3 Hz, 1H).

Example 20

(±)-4-(((trans)-4-(1-(6-chloro-1H-imidazo[4,5-b]pyridin-2-yl)-3-propyl)cyclohexyl) oxy)quinoline

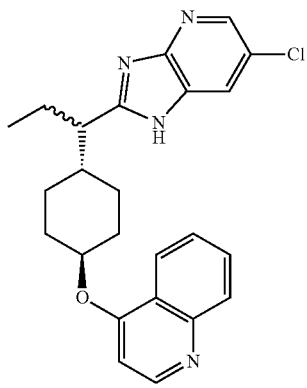 [SMILES: CCC(c1nc2ncc(Cl)cc2[nH]1)[C@H]1CC[C@H](Oc2ccnc3ccccc23)CC1]

Example 20: (±)-4-(((trans)-4-(1-(6-chloro-1H-imidazo[4,5-b]pyridin-2-yl)-3-propyl)cyclohexyl) oxy)quinoline Intermediate 13G (92 mg, 0.294 mmol) was dissolved in thionyl chloride (214 μl, 2.94 mmol) and DMF (11.37 μl, 0.147 mmol) was added. Reaction stirred at room temperature. After 1 hour, the reaction was concentrated in vacuo, taken up in toluene, concentrated again and placed on high vacuum to remove more thionyl chloride. After 15 minutes, the crude acyl chloride was taken up in ACN (734 μl) and added to a solution of 5-chloropyridine-2,3-diamine (84 mg, 0.587 mmol) in ACN (734 μl) and TEA (205 μl, 1.468 mmol) at 0° C. Reaction was then allowed to warm to room temperature. After 30 min, the reaction was diluted with water and extracted with EtOAc. The combined organics were dried with sodium sulfate, filtered and concentrated in vacuo. The crude intermediate was taken up in phosphoryl trichloride (450 mg, 2.94 mmol) and heated to 90° C. After 2 hours, the reaction was quenched by adding slowly to 1N NaOH and basifying until pH~10. The resulting mixture was extracted with EtOAc. The combined organics were dried with sodium sulfate, filtered, and concentrated in vacuo. The crude material was taken up in 2 mL DMF, filtered, and purified via HPLC to give racemic Example 20 (18.9 mg, 0.044 mmol, 15% yield). LC-MS Anal. Calc'd for $C_{24}H_{25}ClN_4O$ 420.17, found [M+H] 421.1, $T_r$=0.69 min (Method A). $^1$H NMR (500 MHz, DMSO-d$_6$) δ: 8.62 (d, J=5.2 Hz, 1H), 8.27 (br. s., 1H), 8.09 (d, J=8.2 Hz, 1H), 8.04 (br. s., 1H), 7.89 (d, J=8.4 Hz, 1H), 7.70 (t, J=7.5 Hz, 1H), 7.52 (t, J=7.6 Hz, 1H), 7.03 (d, J=5.3 Hz, 1H), 4.54 (t, J=10.4 Hz, 1H), 3.58 (br. s., 1H), 2.65-2.71 (m, 1H), 2.21 (d, J=11.8 Hz, 1H), 2.11 (d, J=12.1 Hz, 1H), 1.97-2.06 (m, 1H), 1.72-1.90 (m, 3H), 1.35-1.57 (m, 3H), 1.13-1.28 (m, 2H), 0.71 (t, J=7.2 Hz, 3H)

Enantiomer 1 and Enantiomer 2

Enantiomer 1: Example 20-1, 4-(((trans)-4-(1-(6-chloro-1H-imidazo[4,5-b]pyridin-2-yl)-3-propyl)cyclohexyl) oxy)quinoline (Homochiral, Absolute Stereochemistry not Determined)

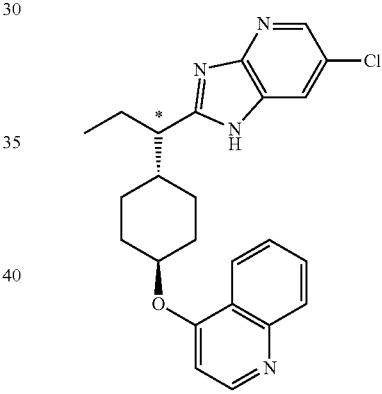

Enantiomer 2: Example 20-2, 4-(((trans)-4-(1-(6-chloro-1H-imidazo[4,5-b]pyridin-2-yl)-3-propyl)cyclohexyl) oxy)quinoline (Homochiral, Absolute Stereochemistry not Determined)

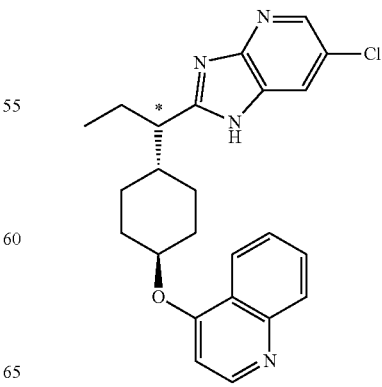

Example 20-1, Enantiomer 1 and Example 20-2, Enantiomer 2: Chiral separation of the racemic sample (Method 1) gave Example 20-1, Enantiomer 1 T$_r$=5.974 min (Method J) and Example 20-2, Enantiomer 2 T$_r$=9.600 min (Method J) Absolute stereochemistry was not determined.

Example 20-1, Enantiomer 1: MS (ES): m/z=421.0 [M+H]$^+$. T$_r$=1.797 min (Method B). $^1$H NMR (500 MHz, DMSO-d$_6$) δ: 8.62 (d, J=5.0 Hz, 1H), 8.20-8.35 (m, 1H), 7.95-8.13 (m, 2H), 7.89 (d, J=8.4 Hz, 1H), 7.70 (t, J=7.4 Hz, 1H), 7.51 (t, J=7.6 Hz, 1H), 7.03 (d, J=5.3 Hz, 1H), 4.54 (br. s., 1H), 3.65 (br. s., 1H), 2.68 (br. s., 1H), 2.21 (d, J=11.7 Hz, 1H), 2.11 (d, J=11.3 Hz, 1H), 2.02 (d, J=13.0 Hz, 1H), 1.72-1.92 (m, 3H), 1.35-1.55 (m, 3H), 1.09-1.27 (m, 2H), 0.70 (t, J=7.1 Hz, 3H)

Example 20-2, Enantiomer 2: MS (ES): m/z=421.3 [M+H]$^+$. T$_r$=1.814 min (Method B). $^1$H NMR (500 MHz, DMSO-d$_6$) δ: 8.62 (d, J=4.9 Hz, 1H), 8.21-8.33 (m, 1H), 7.95-8.12 (m, 2H), 7.89 (d, J=8.2 Hz, 1H), 7.70 (t, J=7.6 Hz, 1H), 7.52 (t, J=7.5 Hz, 1H), 7.03 (d, J=5.3 Hz, 1H), 4.54 (br. s., 1H), 3.65 (br. s., 1H), 2.68 (br. s., 1H), 2.20 (d, J=11.8 Hz, 1H), 2.11 (d, J=11.0 Hz, 1H), 2.02 (d, J=14.3 Hz, 1H), 1.74-1.94 (m, 3H), 1.33-1.56 (m, 3H), 1.11-1.28 (m, 2H), 0.70 (t, J=7.0 Hz, 3H)

Example 21

Isomers 1-4

4-(4-(1-(6-chloro-1H-imidazo[4,5-b]pyridin-2-yl)propyl)cyclohexyl)-6-fluoroquinoline (All Four Isomers are Homochiral, Absolute Stereochemistry not Determined)

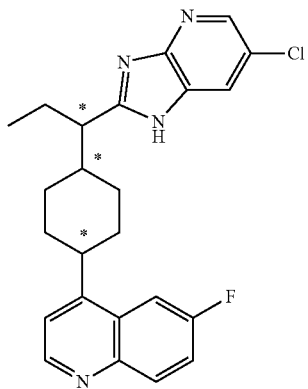 [SMILES: CCC(c1nc2ncc(Cl)cc2[nH]1)C1CCC(c2ccnc3ccc(F)cc23)CC1]

Example 21: Isomers 1-4

4-(4-(1-(6-chloro-1H-imidazo[4,5-b]pyridin-2-yl)propyl)cyclohexyl)-6-fluoroquinoline (All Four Isomers are Homochiral, Absolute Stereochemistry not Determined)

Intermediate 15I (81 mg, 0.257 mmol) was dissolved in thionyl chloride (187 μl, 2.57 mmol) and DMF (9.94 μl, 0.128 mmol) was added. The reaction was stirred at room temperature. After 1 hour, The reaction was concentrated in vacuo, taken up in toluene, concentrated again and placed on high vacuum to remove more thionyl chloride. After 15 minutes, the crude acyl chloride was taken up in ACN (642 μl) and added to a solution of 5-chloropyridine-2,3-diamine (73.7 mg, 0.514 mmol) in ACN (642 μl) and TEA (179 μl, 1.284 mmol) at 0° C. Reaction was then allowed to warm to room temperature. After 30 min, the reaction was diluted with water and extracted with EtOAc. Organics were combined, dried with sodium sulfate, filtered and concentrated in vacuo. The resulting crude intermediate taken up in phosphoryl trichloride (394 mg, 2.57 mmol) and heated to 90° C. After 1 hour, the reaction was quenched by adding slowly to 1N NaOH and basifying until pH~10. The resulting mixture was extracted with EtOAc. Organics dried with sodium sulfate, filtered, and concentrated in vacuo. Crude material taken up in 2 mL DMF, filtered, and purified via HPLC to separate cis and trans diastereomers and chiral SFC separated each into a pair of enantiomers to give 4 homochiral products (relative and absolute stereochemistry not determined).

Isomers 1-4

4-(4-(1-(6-chloro-1H-imidazo[4,5-b]pyridin-2-yl)propyl)cyclohexyl)-6-fluoroquinoline (All Four Isomers are Homochiral, Absolute Stereochemistry not Determined)

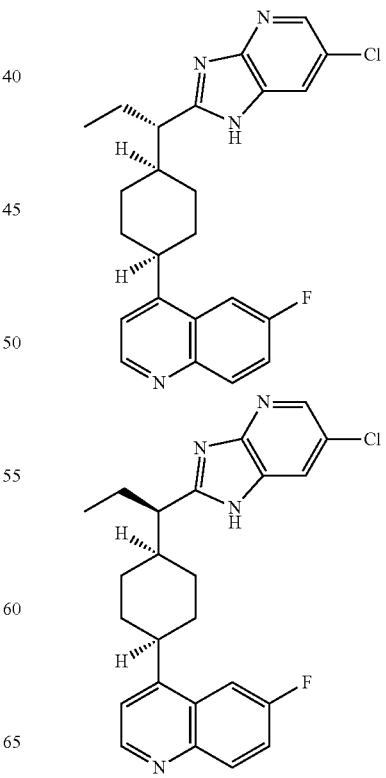

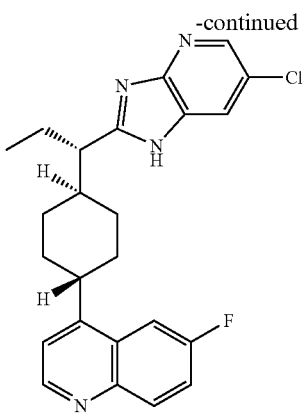

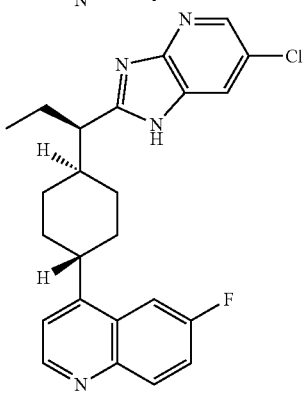

Example 21-1, Enantiomer 1 and Example 21-2, Enantiomer 2: Chiral separation of the racemic sample (Method K) gave Example 21-1, Enantiomer 1 T$_r$=13.038 min (Method L) and Example 21-2, Enantiomer 2 T$_r$=19.022 min (Method L) (Relative and absolute stereochemistry was not determined).

Example 21-3, Enantiomer 3 and Example 21-4, Enantiomer: Chiral separation of the racemic sample (Method M) gave Example 21-3, Enantiomer 3 T$_r$=3.177 min (Method N) and Example 21-4. Enantiomer 4 T$_r$=8.289 min (Method N) (Relative and absolute stereochemistry was not determined).

Example 21-1, Enantiomer 1: MS (ES): m/z=423.0 [M+H]$^+$. T$_r$=1.862 min (Method B). $^1$H NMR (500 MHz, DMSO-d$_6$) δ: 8.84 (d, J=4.3 Hz, 1H), 8.26 (br. s., 1H), 8.08 (dd, J=9.0, 6.0 Hz, 1H), 8.04 (br. s., 1H), 7.94 (d, J=8.9 Hz, 1H), 7.60-7.68 (m, 1H), 7.56 (d, J=4.3 Hz, 1H), 3.60 (br. s., 1H), 3.38 (br. s., 1H), 3.23 (t, J=9.6 Hz, 1H), 2.20 (d, J=9.5 Hz, 1H), 2.03 (d, J=13.4 Hz, 1H), 1.57-1.98 (m, 7H), 1.52 (d, J=10.4 Hz, 1H), 1.07 (d, J=13.1 Hz, 1H), 0.69 (t, J=7.2 Hz, 3H)

Example 21-2, Enantiomer 2: MS (ES): m/z=423.2 [M+H]$^+$. T$_r$=1.824 min (Method B). $^1$H NMR (500 MHz, DMSO-d$_6$) δ: 8.83 (d, J=4.3 Hz, 1H), 8.25 (br. s., 1H), 8.07 (dd, J=9.2, 5.8 Hz, 1H), 8.02 (br. s., 1H), 7.89-7.97 (m, 1H), 7.60-7.67 (m, 1H), 7.56 (d, J=4.6 Hz, 1H), 3.60 (br. s., 1H), 3.37 (br. s., 1H), 3.17-3.27 (m, 1H), 2.19 (d, J=10.1 Hz, 1H), 2.02 (d, J=12.5 Hz, 1H), 1.56-1.96 (m, 7H), 1.51 (d, J=10.4 Hz, 1H), 1.06 (d, J=13.4 Hz, 1H), 0.69 (t, J=7.2 Hz, 3H)

Example 21-3, Enantiomer 3: MS (ES): m/z=423.2 [M+H]$^+$. T$_r$=1.804 min (Method B). $^1$H NMR (500 MHz, DMSO-d$_6$) δ: 8.78 (d, J=4.0 Hz, 1H), 8.26 (br. s., 1H), 8.06 (dd, J=9.0, 6.0 Hz, 2H), 7.88-7.96 (m, 1H), 7.58-7.67 (m, 1H), 7.41 (d, J=4.3 Hz, 1H), 3.40 (br. s., 1H), 3.23 (br. s., 1H), 2.71 (br. s., 1H), 2.06 (d, J=11.3 Hz, 1H), 1.77-1.97 (m, 5H), 1.42-1.61 (m, 3H), 1.28-1.42 (m, 2H), 0.75 (t, J=7.2 Hz, 3H)

Example 21-4, Enantiomer 4: MS (ES): m/z=423.0 [M+H]$^+$. T$_r$=1.825 min (Method B). $^1$H NMR (500 MHz, DMSO-d$_6$) δ: 8.26-8.40 (m, 1H), 7.87-8.22 (m, 4H), 7.70 (br. s., 1H), 7.54 (br. s., 1H), 3.26 (br. s., 1H), 2.72 (s, 1H), 2.04 (br. s., 1H), 1.74-1.96 (m, 5H), 1.43-1.64 (m, 3H), 1.35 (br. s., 2H), 0.74 (br. s., 3H)

Example 22 (±)-4-((cis)-4-(1-(6-chloro-1H-imidazo[4,5-b]pyridin-2-yl)propyl)cyclohexyl)-6-(trifluoromethyl)quinoline Example 22: (±)-4-((cis)-4-(1-(6-chloro-1H-imidazo[4,5-b]pyridin-2-yl)propyl)cyclohexyl)-6-(trifluoromethyl)quinoline Intermediate 17 (40 mg, 0.109 mmol) was dissolved in thionyl chloride (80 μl, 1.095 mmol) and DMF (4.24 μl, 0.055 mmol) was added. Reaction stirred at room temperature. After 1 hour, the reaction was concentrated in vacuo, taken up in toluene, concentrated again and placed on high vacuum to remove more thionyl chloride. After 15 minutes, the crude acyl chloride was taken up in ACN (547 μl) and added to a solution of 5-chloropyridine-2,3-diamine (31.4 mg, 0.219 mmol) in ACN (547 μl) and TEA (76 μl, 0.547 mmol) at 0° C. The reaction was then allowed to warm to room temperature. After 1 h, the reaction was diluted with water and extracted with EtOAc. Organics were combined, dried with sodium sulfate, filtered and concentrated in vacuo. The crude residue was taken up in POCl$_3$ (102 μl, 1.095 mmol) and heated to 90° C. for 1 hour. Reaction was quenched into cold (over ice) 1N NaOH and extracted with EtOAc. Organics dried with sodium sulfate, filtered and concentrated. Crude residue taken up in DMF, filtered, and purified via HPLC to give Example 22. LC-MS Anal. Calc'd for C$_{25}$H$_{24}$ClF$_3$N$_4$ 472.16, found [M+H] 473.1, T$_r$=0.85 min (Method A). $^1$H NMR (500 MHz, DMSO-d$_6$) δ: 9.04 (d, J=4.4 Hz, 1H), 8.56 (br. s., 1H), 8.16-8.35 (m, 2H), 7.93-8.14 (m, 2H), 7.71 (d, J=4.1 Hz, 1H), 3.60 (br. s., 1H), 3.36 (br. s., 1H), 3.17-3.28 (m, 1H), 2.20 (br. s., 1H), 2.04 (d, J=14.1 Hz, 1H), 1.20-1.98 (m, 8H), 1.08 (d, J=12.5 Hz, 1H), 0.71 (t, J=7.2 Hz, 3H)

Example 22, Enantiomers 1 and 2

4-((cis)-4-(1-(6-chloro-1H-imidazo[4,5-b]pyridin-2-yl)propyl)cyclohexyl)-6-(trifluoromethyl)quinoline (Homochiral, Absolute Stereochemistry not Determined)

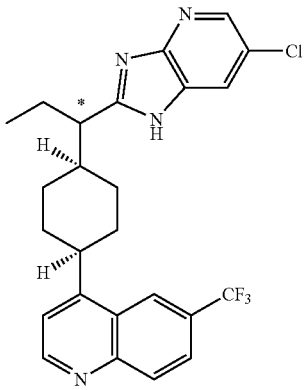 [SMILES: CCC(c1nc2ncc(Cl)cc2[nH]1)[C@H]1CC[C@@H](c2ccnc3ccc(C(F)(F)F)cc32)CC1]

Example 22-1, Enantiomer 1 and Example 22-2, Enantiomer 2: Chiral separation of the racemic sample (Method O) gave Example 21-1, Enantiomer 1 $T_r$=5.905 min (Method P) and Example 22-2, Enantiomer 2 $T_r$=6.896 min (Method P) (absolute stereochemistry was not determined).

Example 22-1, Enantiomer 1: MS (ES): m/z=472.9 [M+H]$^+$. $T_r$=2.079 min (Method B). $^1$H NMR (500 MHz, DMSO-d$_6$) δ: 9.03 (d, J=4.3 Hz, 1H), 8.55 (s, 1H), 8.20-8.30 (m, 2H), 8.04 (br. s., 1H), 7.99 (d, J=8.8 Hz, 1H), 7.70 (d, J=4.3 Hz, 1H), 3.60 (br. s., 1H), 3.44 (br. s., 1H), 3.24 (br. s., 1H), 2.20 (br. s., 1H), 2.04 (d, J=15.6 Hz, 1H), 1.60-1.98 (m, 7H), 1.54 (d, J=11.9 Hz, 1H), 1.09 (d, J=12.8 Hz, 1H), 0.71 (t, J=7.2 Hz, 3H)

Example 22-2, Enantiomer 2: MS (ES): m/z=473.3 [M+H]$^+$. $T_r$=2.079 min (Method B). $^1$H NMR (500 MHz, DMSO-d$_6$) δ: 9.03 (d, J=4.3 Hz, 1H), 8.55 (s, 1H), 8.20-8.29 (m, 2H), 8.04 (br. s., 1H), 7.99 (d, J=8.2 Hz, 1H), 7.70 (d, J=4.6 Hz, 1H), 3.59 (br. s., 1H), 3.24 (br. s., 1H), 2.21 (d, J=7.3 Hz, 1H), 2.04 (d, J=16.2 Hz, 1H), 1.61-1.99 (m, 8H), 1.54 (d, J=10.4 Hz, 1H), 1.08 (d, J=12.2 Hz, 1H), 0.71 (t, J=7.2 Hz, 3H)

Example 23 Enantiomers 1 and 2

6-chloro-2-(1-((cis)-4-(2-fluoro-3-methylpyridin-4-yl)cyclohexyl)-3-propyl)-1H-benzo[d]imidazole (Homochiral, Absolute Stereochemistry not Determined)

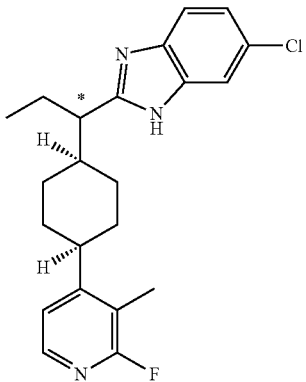

Intermediate 23A: ethyl 2-(4-(2-fluoro-3-methylpyridin-4-yl)cyclohex-3-en-1-yl)acetate To a sealable reaction flask containing a solution of Intermediate 15E (9.90 g, 33.7 mmol) in Dioxane (195 mL) was added 4-bromo-2-fluoro-3-methylpyridine (6.21 g, 32.7 mmol), Water (65.0 mL) and Na$_2$CO$_3$ (13.86 g, 131 mmol). After the mixture was degassed with Argon for 10-15 min, Pd(Ph$_3$P)$_4$ (1.888 g, 1.634 mmol) was added, the flask was sealed and the mixture was heated to 100° C. for 24 hours, then allowed to slowly cool to rt. Reaction was diluted with EtOAc and water, plus sonication to break up solids, then transferred to a sep funnel. The layers were separated and the aqueous layer was extracted once more with EtOAc. The organic layers were combined, washed with brine, dried over anhyd Na$_2$SO$_4$, filtered and concentrated in vacuo to afford a dark brown residue. Purified on silica gel column chromatography to give Intermediate 23A (7.23 g, 26.1 mmol, 80% yield). LC-MS Anal. Calc'd for C$_{16}$H$_{20}$FNO$_2$ 277.15, found [M+H] 278.2, $T_r$=1.04 min (Method A).

Intermediate 23B: ethyl 2-((cis)-4-(2-fluoro-3-methylpyridin-4-yl)cyclohexyl)acetate To a round bottom flask equipped with a reflux condenser, containing a homogeneous mixture of Intermediate 23A (7.2285 g, 26.1 mmol) in methanol (100 mL) was added ammonium formate (8.22 g, 130 mmol). The resulting mixture was sparged with Argon for 5-10 min, before being evacuated then purged with nitrogen (×3). To this mixture was then added palladium on carbon (10% Pd/C, wet Degussa type) (2.77 g, 2.61 mmol) and the reaction was heated to reflux (bath temp ca. 70° C.). Refluxed for 3 hours then allowed to cool slowly to room temperature. Stir bar removed before reaction concentrated to remove volatiles, then treated with DCM and filtered through a pad of celite which was thoroughly rinsed with DCM. The combined filtrates were concentrated in vacuo to afford an opaque residue. The residue was resubjected to the original conditions of the reaction [methanol (100 mL), ammonium formate (8.22 g, 130 mmol); evacuate then purge with nitrogen ×3; palladium on carbon (10% Pd/C, wet Degussa type) (2.77 g, 2.61 mmol); heat to reflux]. After 4 hours, reaction cooled to rt. Stir bar removed before reaction concentrated to remove volatiles, then treated with DCM and filtered through a pad of celite which was thoroughly rinsed with DCM. The combined filtrates were concentrated in vacuo to afford a clear oil. This residue was purified via supercritical fluid chromatography to separate cis and trans diastereomers to give Intermediate 23B (2.18 g, 7.80 mmol, 30%). LC-MS Anal. Calc'd for C$_{16}$H$_{22}$FNO$_2$ 279.35, found [M+H] 280.2. $T_r$=1.02 min (Method A).

Intermediate 23C: ethyl 2-((cis)-4-(2-fluoro-3-methylpyridin-4-yl)cyclohexyl)butanoate To a flask containing THF (15 mL) was added lithium diisopropylamide (1.5 M solution in cyclohexane) (11.03 mL, 16.54 mmol) and DMPU (1.360 mL, 11.28 mmol) at −78° C., followed by addition of a solution of Intermediate 23B (2.1 g, 7.52 mmol) in THF (8 mL) dropwise at −78° C. The resulting orange solution mixture was stirred at −78° C. for 1 hour, then iodoethane (0.969 mL, 12.03 mmol) was added. The reaction mixture was stirred at −78° C., then gradually warmed up to room temperature and stirred for 4 hours. The reaction mixture turned a cloudy yellow. The reaction mixture was quenched with $NH_4Cl$ aqueous solution. The resulting mixture was extracted with ethyl acetate. The organic layers were combined, washed with brine, dried over $MgSO_4$. The filtrate was concentrated in vacuo. The residue was dissolved in DCM, purified by silica gel column chromatography to give Intermediate 23C (1.31 g, 4.26 mmol, 57%). LC-MS Anal. Calc'd for $C_{18}H_{26}FNO_2$ 307.20, found [M+H] 308.2. $T_r$=1.08 min (Method A).

Intermediate 23D: 2-((cis)-4-(2-fluoro-3-methylpyridin-4-yl)cyclohexyl)butanoic acid To the reaction mixture of Intermediate 23C (0.9 g, 2.93 mmol) in THF (10 mL) and MeOH (6 mL) was added lithium hydroxide (2M aqueous solution) (14.64 mL, 29.3 mmol). The reaction mixture was heated at 70° C. over night. After over night, to the reaction mixture was added more 2M lithium hydroxide solution (14.64 mL, 29.3 mmol) (4 mL) and MeOH (6 mL) (4 mL). The reaction mixture was heated at 70° C. for another 20 h. The reaction mixture was cooled down and to the reaction mixture was added 2 mL of acetic acid to pH=5. The resulting mixture was extracted with ethyl acetate twice and the organic layers were washed with brine, dried over $MgSO_4$, and filtered. The filtrate was concentrated in vacuo. The residue was purified by HPLC to give Intermediate 23D (425 mg, 1.51 mmol, 51% yield). LC-MS Anal. Calc'd for $C_{16}H_{22}FNO_2$ 279.16, found [M+H] 280.1, $T_r$=0.89 min (Method A).

Example 23 Enantiomers 1 and 2: 6-chloro-2-(1-((cis)-4-(2-fluoro-3-methylpyridin-4-yl)cyclohexyl)-3-propyl)-1H-benzo[d]imidazole (Homochiral, Absolute Stereochemistry not Determined)

Intermediate 23D (34 mg, 0.122 mmol) was dissolved in thionyl chloride (89 μl, 1.217 mmol) and DMF (4.71 μl, 0.061 mmol) was added. Reaction stirred at room temperature. After 1 hour, the reaction was concentrated in vacuo, taken up in toluene, concentrated again and placed on high vacuum to remove residual thionyl chloride. After 15 minutes, the crude acyl chloride was taken up in ACN (609 μl) and added to a solution of 4-chlorobenzene-1,2-diamine (34.7 mg, 0.243 mmol) in ACN (609 μl) and TEA (85 μl, 0.609 mmol) at 0° C. Reaction was then allowed to warm to room temperature. After overnight, the reaction was diluted with water and extracted with EtOAc. Organics were combined, dried with sodium sulfate, filtered and concentrated in vacuo. The crude residue was taken up in $POCl_3$ (113 μl, 1.217 mmol). Reaction heated to 90° C. After 1 hour, the reaction was quenched into 1N NaOH and extracted with EtOAc. Organics dried with sodium sulfate, filtered and concentrated. Crude residue taken up in DMF, filtered, and purified by HPLC to give racemic Example 23. This material was further purified via chiral SFC to give Enantiomers 1 and 2 below Example 23, Enantiomers 1 and 2

6-chloro-2-(1-((cis)-4-(2-fluoro-3-methylpyridin-4-yl)cyclohexyl)-3-propyl)-1H-benzo[d]imidazole (Homochiral, Absolute Stereochemistry not Determined)

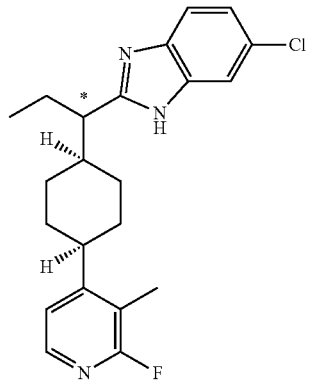 [SMILES: CCC(c1nc2ccc(Cl)cc2[nH]1)[C@H]1CC[C@@H](c2ccnc(F)c2C)CC1]

Example 23-1, Enantiomer 1 and Example 23-2, Enantiomer 2: Chiral separation of the racemic sample (Method Q) gave Example 23-1, Enantiomer 1 $T_r$=3.944 min (Method R) and Example 23-3, Enantiomer 2 $T_r$=4.681 min (Method R) (absolute stereochemistry was not determined).

Example 23-1, Enantiomer 1: MS (ES): m/z=386.0 [M+H]⁺. $T_r$=2.051 min (Method B). ¹H NMR (500 MHz, DMSO-$d_6$) δ: 8.02 (d, J=5.0 Hz, 1H), 7.41-7.60 (m, 2H), 7.33 (d, J=4.9 Hz, 1H), 7.09-7.17 (m, 1H), 3.37 (br. s., 1H), 3.17 (d, J=10.8 Hz, 1H), 2.84 (br. s., 1H), 2.17 (s, 3H), 2.12 (d, J=10.4 Hz, 1H), 2.02 (d, J=12.5 Hz, 1H), 1.89 (d, J=11.8 Hz, 1H), 1.52-1.78 (m, 5H), 1.45 (br. s., 1H), 1.35 (d, J=10.7 Hz, 1H), 1.02 (d, J=12.2 Hz, 1H), 0.68 (t, J=7.2 Hz, 3H)

Example 23-2, Enantiomer 2: MS (ES): m/z=386.2[M+H]1. $T_r$=2.055 min (Method B). ¹H NMR (500 MHz, DMSO-$d_6$) δ: 8.02 (d, J=4.9 Hz, 1H), 7.41-7.61 (m, 2H), 7.33 (d, J=4.8 Hz, 1H), 7.13 (t, J=9.3 Hz, 1H), 3.37 (br. s., 1H), 3.17 (d, J=11.8 Hz, 1H), 2.84 (br. s., 1H), 2.17 (s, 3H), 2.13 (br. s., 1H), 2.02 (d, J=12.5 Hz, 1H), 1.90 (br. s., 1H), 1.52-1.75 (m, 5H), 1.45 (br. s., 1H), 1.35 (d, J=11.4 Hz, 1H), 1.02 (d, J=12.9 Hz, 1H), 0.68 (t, J=7.1 Hz, 3H)

Example 24

(±)-6-chloro-2-(1-((cis)-4-(2-fluoro-3-methylpyridin-4-yl)cyclohexyl)-3-propyl)-1H-imidazo[4,5-b]pyridine

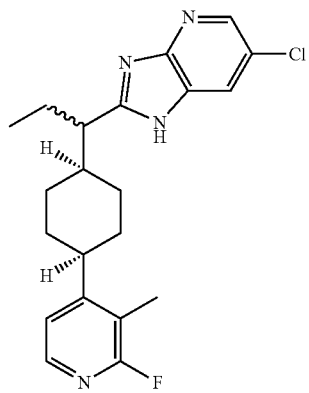 [SMILES: CCC(c1nc2ncc(Cl)cc2[nH]1)[C@H]1CC[C@@H](c2ccnc(F)c2C)CC1]

Example 24: (±)-6-chloro-2-(1-((cis)-4-(2-fluoro-3-methylpyridin-4-yl)cyclohexyl)-3-propyl)-1H-imidazo[4,5-b]pyridine Example 24 was synthesized following the procedures used to make Example 23 from Intermediate 23D, except 5-chloropyridine-2,3-diamine was utilized. LC-MS Anal. Calc'd for $C_{21}H_{24}ClF$ 386.17, found [M+H] 387.1, $T_r$=0.85 min (Method A). $^1$H NMR (500 MHz, DMSO-$d_6$) δ: 8.26 (br. s., 1H), 7.97-8.11 (m, J=5.2 Hz, 2H), 7.33 (d, J=4.9 Hz, 1H), 3.15-3.29 (m, 1H), 2.80-2.90 (m, 1H), 2.10-2.21 (m, 4H), 2.02 (d, J=13.1 Hz, 1H), 1.92 (br. s., 1H), 1.54-1.80 (m, 5H), 1.48 (t, J=13.3 Hz, 1H), 1.37 (d, J=11.0 Hz, 1H), 1.04 (d, J=13.1 Hz, 1H), 0.71 (t, J=7.2 Hz, 3H)

Example 24, Enantiomers 1 and 2

6-chloro-2-(1-((cis)-4-(2-fluoro-3-methylpyridin-4-yl)cyclohexyl)-3-propyl)-1H-imidazo[4,5-b]pyridine (Homochiral, Absolute Stereochemistry not Determined)

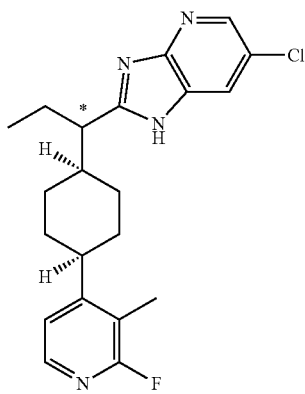 [SMILES: CCC(c1nc2ncc(Cl)cc2[nH]1)[C@H]1CC[C@@H](c2ccnc(F)c2C)CC1]

Example 24-1, Enantiomer 1 and Example 24-2, Enantiomer 2: Chiral separation of the racemic sample (Method S) gave Example 24-1, Enantiomer 1 $T_r$=2.375 min (Method T) and Example 24-2, Enantiomer 2 $T_r$=3.701 min (Method T) (absolute stereochemistry was not determined).

Example 24-1, Enantiomer 1: MS (ES): m/z=387.0 [M+H]$^+$. $T_r$=1.847 min (Method B). $^1$H NMR (500 MHz, DMSO-$d_6$) δ: 8.20-8.33 (m, 1H), 7.95-8.08 (m, 2H), 7.32 (br. s., 1H), 3.21 (d, J=9.8 Hz, 1H), 2.80-2.88 (m, 1H), 2.16 (s, 4H), 1.97-2.07 (m, 1H), 1.90 (s, 1H), 1.52-1.77 (m, 5H), 1.47 (t, J=13.4 Hz, 1H), 1.35 (d, J=12.5 Hz, 1H), 1.01 (d, J=14.3 Hz, 1H), 0.68 (t, J=7.2 Hz, 3H)

Example 24-2, Enantiomer 2: MS (ES): m/z=387.0 [M+H]$^+$. $T_r$=1.862 min (Method B). $^1$H NMR (500 MHz, DMSO-$d_6$) δ: 8.20-8.32 (m, 1H), 7.96-8.08 (m, 2H), 7.32 (br. s., 1H), 3.17-3.27 (m, J=12.8 Hz, 1H), 2.79-2.89 (m, 1H), 2.16 (s, 4H), 1.95-2.08 (m, 1H), 1.90 (br. s., 1H), 1.52-1.77 (m, 5H), 1.42-1.52 (m, 1H), 1.35 (d, J=10.7 Hz, 1H), 1.01 (d, J=13.7 Hz, 1H), 0.68 (t, J=7.0 Hz, 3H)

Example 25

(±)-6-chloro-2-(2-ethoxy-1-((cis)-4-(2-fluoro-3-methylpyridin-4-yl)cyclohexyl)ethyl)-1H-benzo[d]imidazole

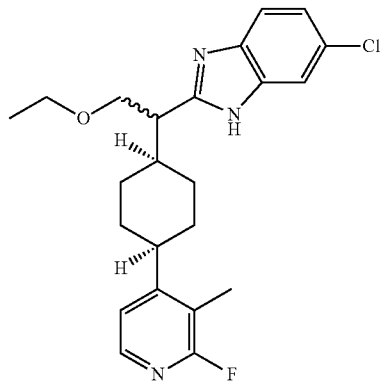 [SMILES: CCOCC(c1nc2ccc(Cl)cc2[nH]1)[C@H]1CC[C@@H](c2ccnc(F)c2C)CC1]

Intermediate 25A: ethyl 3-ethoxy-2-(4-(2-fluoro-3-methylpyridin-4-yl)cyclohex-3-en-1-yl)propanoate To a flask containing THF (15 mL) was added lithium diisopropylamine (1.5 M solution in cyclohexane) (16.66 mL, 24.99 mmol) at −78° C. Once the addition was complete, DMPU (2.152 mL, 17.85 mmol) was added followed by a solution of Intermediate 23A (3.3 g, 11.90 mmol) in THF (8 mL) dropwise −78° C. The resulting mixture was stirred at −78° C. for 1.5 hours, then chloromethyl ethyl ether (2.228 mL, 23.80 mmol) was added. The reaction mixture was stirred at −78° C., then gradually warmed up to room temperature and stirred for 3 h. During this time, a brown sticky solid forms. After 3 h, the reaction mixture turned into clear orange solution. The reaction mixture was quenched with NH$_4$Cl aqueous solution and the resulting mixture was extracted with ethyl acetate. The organic layers were combined, washed with brine, dried over MgSO$_4$, and filtered. The filtrate was concentrated in vacuo. The residue was dissolved in DCM, purified by silica gel column chromatography to give Intermediate 25A (1.8 g, 5.37 mmol, 45% yield). LC-MS Anal. Calc'd for $C_{19}H_{26}FNO_3$ 335.19, found [M+H]336.3, $T_r$=1.06 min (Method A).

Intermediate 25B: ethyl 3-ethoxy-2-((cis)-4-(2-fluoro-3-methylpyridin-4-yl)cyclohexyl)propanoate The round bottom flask containing a solution of Intermediate 25A (1.8 g, 5.37 mmol) in MeOH (40 mL) was evacuated and then under nitrogen stream were added ammonium formate (1.692 g, 26.8 mmol) and palladium on carbon (10 wt %, wet Degussa type) (0.571 g, 0.537 mmol) (wet) at room temperature. The resulting mixture was heated at 80° C. for 5 hours. The reaction mixture was cooled down, concentrated in vacuo, and taken up in DCM. The reaction mixture was filtered through a celite pad and rinsed with DCM. The filtrate was concentrated in vacuo and the cis and trans diastereomers were purified via SFC to give the cis Intermediate 25B (confirmed by NMR) (0.76 g, 2.25 mmol, 42% yield). LC-MS Anal. Calc'd for $C_{19}H_{28}FNO_3$ 337.21, found [M+H] 338.2, $T_r$=1.04 min (Method A).

Intermediate 25C: 3-ethoxy-2-((cis)-4-(2-fluoro-3-methylpyridin-4-yl)cyclohexyl)propanoic acid To a solution of Intermediate 25B (0.72 g, 2.134 mmol) in THF (10 mL) and MeOH (4 mL) was added LiOH (2 M solution) (10.67 mL, 21.34 mmol). The resulting mixture was heated at 45° C. for 5.5 h. The reaction mixture was cooled down and to the reaction mixture was added 1 N HCl solution to reach a pH of ~5. White solid precipitated out. The resulting mixture was extracted with ethyl acetate. The organic layer was dried over $MgSO_4$ and filtered. The filtrate was concentrated in vacuo. The crude product was purified via HPLC to give Intermediate 25C (0.60 g, 1.94 mmol, 91% yield). LC-MS Anal. Calc'd for $C_{17}H_{24}FNO_3$ 309.17, found [M+H] 310.2, $T_r$=0.86 min (Method A).

Example 25: (±)-6-chloro-2-(2-ethoxy-1-((cis)-4-(2-fluoro-3-methylpyridin-4-yl)cyclohexyl)ethyl)-1H-benzo[d]imidazole Intermediate 25C (62 mg, 0.200 mmol) was dissolved in thionyl chloride (146 μl, 2.004 mmol) and DMF (7.76 μl, 0.100 mmol) was added. Reaction stirred at room temperature. After 1 hour, the reaction was concentrated in vacuo, taken up in toluene, concentrated again and placed on high vacuum to remove residual thionyl chloride. After 15 minutes, the crude acyl chloride was taken up in ACN (501 μl) and added to a solution of 4-chlorobenzene-1,2-diamine (57.1 mg, 0.401 mmol) in ACN (501 μl) and TEA (140 μl, 1.002 mmol) at 0° C. Reaction was then allowed to warm to room temperature. After 15 minutes, the reaction was diluted with water and extracted with EtOAc. The organics were combined, dried with sodium sulfate, filtered and concentrated in vacuo. The crude intermediate was taken up in phosphoryl trichloride (307 mg, 2.004 mmol) and heated to 90° C. After 2 hours, the reaction was quenched by adding slowly to 1N NaOH and basifying until pH~10. The resulting mixture was extracted with EtOAc. The combined organics were dried with sodium sulfate, filtered, and concentrated in vacuo. The crude material taken up in 2 mL DMF, filtered, and purified via HPLC to give racemic Example 25 (20.5 mg, 0.048 mmol, 24% yield). LC-MS Anal. Calc'd for $C_{23}H_{27}ClFN_3O$ 415.18, found [M+H] 416.2. $T_r$=0.81 min (Method A). $^1$H NMR (500 MHz, DMSO-$d_6$) δ: 8.02 (d, J=4.9 Hz, 1H), 7.62 (s, 1H), 7.56 (d, J=8.5 Hz, 1H), 7.34 (d, J=5.2 Hz, 1H), 7.23 (d, J=8.9 Hz, 1H), 3.79 (d, J=6.4 Hz, 2H), 3.58-3.67 (m, 1H), 3.34 (dd, J=9.5, 7.0 Hz, 1H), 2.85 (br. s., 1H), 2.13-2.26 (m, 4H), 1.97 (d, J=12.5 Hz, 1H), 1.55-1.80 (m, 4H), 1.48 (t, J=13.4 Hz, 1H), 1.37 (d, J=12.2 Hz, 1H), 0.94-1.07 (m, 4H)

Example 25, Enantiomers 1 and 2

6-chloro-2-(2-ethoxy-1-((cis)-4-(2-fluoro-3-methylpyridin-4-yl)cyclohexyl)ethyl)-1H-benzo[d]imidazole (Homochiral, Absolute Stereochemistry not Determined)

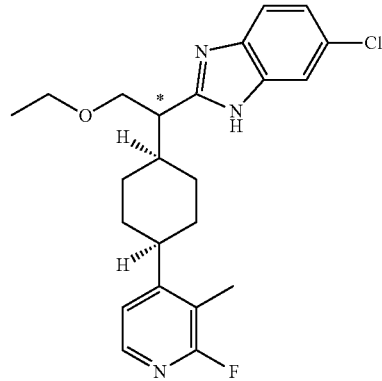 [SMILES: CCOCC(c1nc2ccc(Cl)cc2[nH]1)[C@H]1CC[C@@H](c2ccnc(F)c2C)CC1]

Example 25-1, Enantiomer 1 and Example 25-2, Enantiomer 2: Chiral separation of the racemic sample (Method U) gave Example 25-1, Enantiomer 1 $T_r$=3.783 min (Method V) and Example 25-2, Enantiomer 2 $T_r$=6.989 min (Method V) (absolute stereochemistry was not determined).

Example 25-1, Enantiomer 1: MS (ES): m/z=416.0 [M+H]$^+$. $T_r$=2.066 min (Method B) $^1$H NMR (500 MHz, DMSO-$d_6$) δ: 8.01 (d, J=4.9 Hz, 1H), 7.40-7.62 (m, 2H), 7.32 (d, J=5.2 Hz, 1H), 7.14 (d, J=7.3 Hz, 1H), 3.76 (d, J=6.4 Hz, 2H), 3.38-3.46 (m, 1H), 3.27-3.38 (m, 1H), 2.83 (br. s., 1H), 2.16 (s, 4H), 1.91-2.03 (m, 1H), 1.52-1.78 (m, 4H), 1.45 (t, J=13.1 Hz, 1H), 1.35 (d, J=11.6 Hz, 1H), 0.92-1.05 (m, 4H)

Example 25-2, Enantiomer 2: MS (ES): m/z=416.0 [M+H]$^+$. $T_r$=2.066 min (Method B). $^1$H NMR (500 MHz, DMSO-$d_6$) δ: 8.01 (d, J=4.9 Hz, 1H), 7.38-7.60 (m, 2H), 7.32 (d, J=4.9 Hz, 1H), 7.14 (d, J=7.3 Hz, 1H), 3.76 (d, J=6.1 Hz, 2H), 3.39-3.48 (m, 1H), 3.28-3.38 (m, 1H), 2.83 (br. s., 1H), 2.16 (s, 4H), 1.96 (d, J=12.2 Hz, 1H), 1.52-1.74 (m, 4H), 1.45 (t, J=13.3 Hz, 1H), 1.35 (d, J=10.4 Hz, 1H), 0.89-1.09 (m, 4H)

Example 26

4-((cis)-4-((R)-1-([1,2,4]triazolo[4,3-a]pyridin-3-yl)ethyl)cyclohexyl)-6-fluoroquinoline

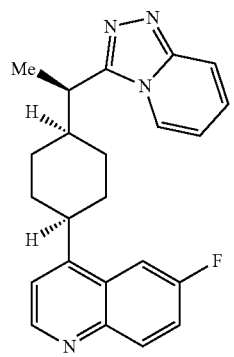 [SMILES: C[C@@H](c1nnc2ccccn12)[C@H]1CC[C@@H](c2ccnc3ccc(F)cc32)CC1]

Intermediate 26A: (R)-2-((cis)-4-(6-fluoroquinolin-4-yl)cyclohexyl)-N'-(pyridin-2-yl)propanehydrazide Preparation 1K (50 mg, 0.166 mmol) was dissolved in thionyl chloride (60.5 µl, 0.830 mmol) and DMF (6.42 µl, 0.083 mmol) was added. Reaction stirred at room temperature. After 1 hour, the reaction was concentrated in vacuo, taken up in toluene, concentrated again and placed on high vacuum to remove excess thionyl chloride. After 15 minutes, the crude acyl chloride was taken up in ACN (1659 µl) and added to a solution of 2-hydrazinylpyridine (36.2 mg, 0.332 mmol) in ACN (1659 µl) and TEA (116 µl, 0.830 mmol) at 0° C. It was then stirred at room temperature for 16 hours. After 16 hours, the reaction was concentrated in vacuo. The crude residue was purified via silica gel column chromatography to give Intermediate 26A (54 mg, 0.138 mmol, 83% yield). LC-MS Anal. Calc'd for $C_{23}H_{25}FN_4O$ 392.20, found [M+H] 393.2, $T_r$=0.61 min (Method A).

Example 26: 4-((cis)-4-((R)-1-([1,2,4]triazolo[4,3-a]pyridin-3-yl)ethyl)cyclohexyl)-6-fluoroquinoline Intermediate 26A (54 mg, 0.138 mmol) was dissolved in $POCl_3$ (275 µl) in a sealed vial and heated to 100° C. After 90 minutes, the reaction was cooled and carefully quenched over ice. The resulting mixture was taken to pH ~10 with 1N NaOH and extracted with iPrOH/CHCl3 (3/7 ratio). Combined organics were dried over sodium sulfate, filtered, and concentrated in vacuo. The resulting residue was then taken up in DMF, filtered, and purified via HPLC to give Example 26 (6.9 mg, 0.018 mmol, 13% yield). LC-MS Anal. Calc'd for $C_{23}H_{23}FN_4$ 374.19, found [M+H] 375.2. $T_r$=0.60 min (Method A). $^1$H NMR (500 MHz, DMSO-$d_6$) δ: 8.82 (d, J=4.5 Hz, 1H), 8.67 (d, J=6.9 Hz, 1H), 8.07 (dd, J=9.0, 5.8 Hz, 1H), 7.94 (dd, J=10.9, 2.2 Hz, 1H), 7.70 (d, J=9.3 Hz, 1H), 7.59-7.67 (m, 2H), 7.29-7.37 (m, 1H), 6.98 (t, J=6.7 Hz, 1H), 3.87 (dd, J=10.6, 7.0 Hz, 1H), 3.39 (br. s., 1H), 2.41 (d, J=10.2 Hz, 1H), 2.05 (d, J=8.4 Hz, 1H), 1.82-1.97 (m, 2H), 1.59-1.82 (m, 3H), 1.53 (d, J=11.6 Hz, 1H), 1.34 (d, J=6.8 Hz, 3H), 1.10 (d, J=11.3 Hz, 1H)

Example 27

6-fluoro-4-((cis)-4-((R)-1-(imidazo[1,5-a]pyridin-3-yl)ethyl)cyclohexyl)quinoline

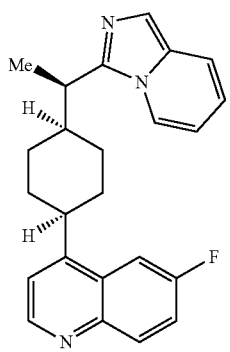 [SMILES: C[C@@H](c1ncc2ccccn12)[C@H]1CC[C@@H](c2ccnc3ccc(F)cc32)CC1]

Intermediate 27A: (R)-2-((cis)-4-(6-fluoroquinolin-4-yl)cyclohexyl)-N-(pyridin-2-ylmethyl)propanamide Preparation 1K (50 mg, 0.166 mmol) was dissolved in thionyl chloride (60.5 µl, 0.830 mmol) and DMF (6.42 µl, 0.083 mmol) was added. Reaction stirred at room temperature. After 1 hour, the reaction was concentrated in vacuo, taken up in toluene, concentrated again and placed on high vacuum to remove excess thionyl chloride. After 15 minutes, the crude acyl chloride was taken up in ACN (1659 µl) and added to a solution of pyridin-2-ylmethanamine (35.9 mg, 0.332 mmol) in ACN (1659 µl) and TEA (116 µl, 0.830 mmol) at 0° C. After 30 minutes shows the reaction was concentrated in vacuo. The resulting crude residue was purified via silica gel column chromatography to give Intermediate 27A (64 mg, 0.163 mmol, 99% yield). LC-MS Anal. Calc'd for $C_4H_{26}FN_3O$ 391.21, found [M+H]392.2, $T_r$=0.61 min (Method A).

Example 27: 6-fluoro-4-((cis)-4-((R)-1-(imidazo[1,5-a]pyridin-3-yl)ethyl)cyclohexyl)quinoline Intermediate 27A (54 mg, 0.138 mmol) was taken up in polyphosphoric acid (276 µl) and heated to 120° C. Heated for 16 hours. Reaction was then cooled and carefully diluted with water. It was then basified with 1N NaOH and the resulting mixture was extracted with EtOAc. The organic extracts were combined, dried with sodium sulfate, filtered, and concentrated in vacuo. Crude residue taken up in DMF, filtered, and purified via HPLC to give Example 27 (21.4 mg, 0.057 mmol, 42% yield). LC-MS Anal. Calc'd for $C_{24}H_{24}FN_3$ 373.20, found [M+H] 374.2, $T_r$=0.60 min (Method A). $^1$H NMR (500 MHz, DMSO-$d_6$) δ: 8.84 (d, J=4.3 Hz, 1H), 8.43 (d, J=7.0 Hz, 1H), 8.07 (dd, J=9.0, 6.0 Hz, 1H), 7.90-7.97 (m, 1H), 7.60-7.69 (m, 2H), 7.47 (d, J=9.2 Hz, 1H), 7.31 (s, 1H), 6.64-6.70 (m, 1H), 6.57-6.64 (m, 1H), 3.77 (dd, J=10.5, 6.9 Hz, 1H), 3.37 (br. s., 1H), 2.35 (d, J=9.8 Hz, 1H), 2.03 (d, J=12.2 Hz, 1H), 1.81-1.99 (m, 2H), 1.55-1.76 (m, 3H), 1.52 (d, J=12.2 Hz, 1H), 1.27 (d, J=6.7 Hz, 3H), 1.07 (d, J=12.5 Hz, 1H)

Example 28

3-((R)-1-((cis)-4-(6-fluoroquinolin-4-yl)cyclohexyl)ethyl)quinazolin-4(3H)-one

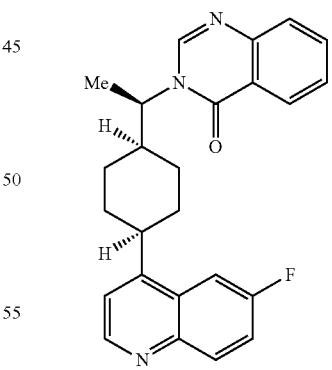

Intermediate 28A: (R)-1-((cis)-4-(6-fluoroquinolin-4-yl)cyclohexyl)ethan-1-amine Preparation 1K (2 g, 6.64 mmol) was taken up in Toluene (22.12 ml) and diphenyl phosphorazidate (2.009 g, 7.30 mmol) and triethylamine (1.110 ml, 7.% mmol) were added. Vial sealed and heated to 70° C. After 2 hours, the reaction was cooled to room temperature and concentrated under reduced pressure. Crude residue was taken up in 40 mL THF and 40 mL of water and lithium hydroxide (1.589 g, 66.4 mmol) was added. The reaction was stirred at room temperature for 1 hour. The reaction was acidified with 1N HCl (white precipitate forms) and extracted with EtOAc. The aqueous portion was then basified with 1N NaOH (precipitate forms) and extracted with EtOAc 5 times. Basic extracts were concentrated in vacuo to give Intermediate 28A (1.68 g, 6.17 mmol, 93% yield). LC-MS Anal. Calc'd for $C_{17}H_{21}FN_2$ 272.17, found [M+H] 273.1 $T_r$=0.50 min (Method A). $^1$H NMR (400 Mhz, CHLOROFORM-d) δ: 8.80 (d, J=4.6 Hz, 1H), 8.11 (dd, J=9.3, 5.7 Hz, 1H), 7.67 (dd, J=10.6, 2.8 Hz, 1H), 7.46 (ddd, J=9.2, 8.0, 2.8 Hz, 1H), 7.32 (d, J=4.5 Hz, 1H), 3.27-3.37 (m, 1H), 3.13 (dq, J=9.3, 6.3 Hz, 1H), 2.01-2.10 (m, 1H), 1.67-1.92 (m, 6H), 1.37-1.55 (m, 4H), 1.15 (d, J=6.4 Hz, 3H)

Intermediate 28B: 2-amino-N—((R)-1-((cis)-4-(6-fluoroquinolin-4-yl)cyclohexyl)ethyl) benzamide Intermediate 28A (50 mg, 0.184 mmol) was taken up in DMF (1836 μl) and HOBT (36.5 mg, 0.239 mmol), EDC (45.8 mg, 0.239 mmol), 2-aminobenzoic acid (50.4 mg, 0.367 mmol) and TEA (128 μl, 0.918 mmol) were added. The reaction was stirred at room temperature. After 3 days the reaction was diluted with EtOAc and extracted with 5:1 water:saturated aqueous sodium bicarbonate solution. The organic extracts were combined, dried with sodium sulfate, filtered, and concentrated in vacuo. The crude residue was purified on silica gel column chromatography to give Intermediate 28B (57 mg, 0.146 mmol, 79% yield). LC-MS Anal. Calc'd for $C_{24}H_{26}FN_3O$ 391.21, found [M+H] 392.2 $T_r$=0.72 min (Method A).

Example 28: 3-((R)-1-((cis)-4-(6-fluoroquinolin-4-yl)cyclohexyl)ethyl) quinazolin-4(3H)-one Intermediate 28B (57 mg, 0.146 mmol) taken up in DMSO (728 μl) in pressure vial. Tosic acid (41.5 mg, 0.218 mmol) and triethyl orthoformate (36.4 μl, 0.218 mmol) were added and the reaction was heated to 50° C. for one hour. The reaction as then heated to 70° C. for another 2 hours. Reaction was cooled and triethyl orthoformate (36.4 μl, 0.218 mmol) was added and reaction stirred another hour at 70° C. The reaction was then diluted further with 1 mL of DMSO, filtered, and purified via HPLC to give Example 28 (30 mg, 0.073 mmol, 50% yield). LC-MS Anal. Calc'd for $C_{25}H_{24}FN_3O$ 401.19, found [M+H] 402.2 $T_r$=0.74 min (Method A). $^1$H NMR (500 MHz, DMSO-$d_6$) δ: 8.86 (d, J=4.3 Hz, 1H), 8.51 (s, 1H), 8.17 (d, J=7.9 Hz, 1H), 8.09 (dd, J=9.3, 6.0 Hz, 1H), 7.97 (dd, J=10.8, 2.6 Hz, 1H), 7.78-7.86 (m, 1H), 7.61-7.72 (m, 2H), 7.47-7.59 (m, 2H), 3.32-3.46 (m, 1H), 1.90-2.04 (m, 3H), 1.72-1.90 (m, 4H), 1.66 (t, J=13.1 Hz, 1H), 1.56 (d, J=10.7 Hz, 1H), 1.50 (d, J=6.1 Hz, 3H), 1.25 (d, J=13.4 Hz, 1H)

Example 29

6-chloro-2-((R)-1-((cis)-4-(6-fluoroquinolin-4-yl)cyclohexyl)ethyl)quinazolin-4(3H)-one

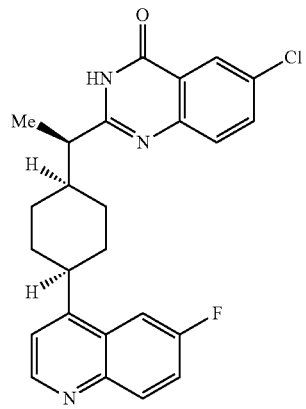 [SMILES: C[C@@H](c1nc2ccc(Cl)cc2c(=O)[nH]1)[C@H]1CC[C@@H](c2ccnc3ccc(F)cc32)CC1]

Intermediate 29A: 5-chloro-2-((R)-2-((cis)-4-(6-fluoroquinolin-4-yl)cyclohexyl) propan-amido)benzamide Preparation 1K (50 mg, 0.166 mmol) was dissolved in thionyl chloride (60.5 μl, 0.830 mmol) and DMF (6.42 μl, 0.083 mmol) was added. Reaction stirred at room temperature. After 1 hour, the reaction was concentrated in vacuo, taken up in toluene, concentrated again and placed on high vacuum to remove excess thionyl chloride. After 15 minutes, the crude acyl chloride was taken up in ACN (1659 μl) and added to a solution of 2-amino-5-chlorobenzamide (28.3 mg, 0.166 mmol) in ACN (1659 μl) and TEA (116 μl, 0.830 mmol) at 0° C. After 1 hour, the reaction was concentrated in vacuo. The crude residue was diluted with water and extracted with EtOAc. The combined organic extracts were dried with sodium sulfate, filtered, and concentrated in vacuo to give crude Intermediate 29A (75 mg, 0.166 mmol, 100% yield). Used as is without further purification in subsequent step. LC-MS Anal. Calc'd for $C_{25}H_{25}ClFN_3O_2$ 453.16, found [M+H] 454.1 $T_r$=0.80 min (Method A).

Example 29: 6-chloro-2-((R)-1-((cis)-4-(6-fluoroquinolin-4-yl)cyclohexyl)ethyl)quinazolin-4(3H)-one Crude Intermediate 29A (69 mg, 0.152 mmol) was taken up in EtOH (760 μl) in a vial. NaOH (122 mg, 3.04 mmol) was taken up in Water (760 μl) and the resulting solution was added to the ethanol solution. The vial was sealed and heated to 100° C. for 1 hour. The reaction was then diluted with water and extracted with EtOAc. The combined organic extracts were dried with sodium sulfate, filtered and concentrated in vacuo. The crude residue taken up in DMF, filtered, and purified via HPLC to give Example 29 (3.4 mg, 0.008 mmol, 5% yield). LC-MS Anal. Calc'd for $C_{25}H_{23}ClFN_3O$ 435.15, found [M+H] 436.1 $T_r$=0.82 min (Method A). $^1$H NMR (500 MHz, DMSO-$d_6$) δ: 8.85 (d, J=4.6 Hz, 1H), 8.08 (dd, J=9.2, 5.8 Hz, 1H), 8.02 (d, J=2.1 Hz, 1H), 7.95 (d, J=8.9 Hz, 1H), 7.79 (dd, J=8.7, 2.3 Hz, 1H), 7.60-7.69 (m, 2H), 7.58 (d, J=4.3 Hz, 1H), 3.39 (br. s., 1H), 3.16 (dd, J=10.7, 6.7 Hz, 1H), 2.20 (br. s., 1H), 1.77-2.04 (m, 4H), 1.70 (br. s., 3H), 1.57 (d, J=10.7 Hz, 1H), 1.35 (d, J=14.3 Hz, 1H), 1.27 (d, J=6.7 Hz, 3H)

Example 30

6-fluoro-4-((cis)-4-((R)-1-(6-methylimidazo[1,2-b]pyridazin-2-yl)ethyl)cyclohexyl)quinoline

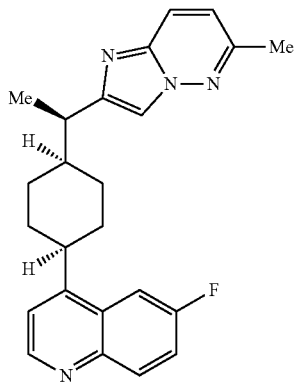 [SMILES: Cc1ccc2nc([C@H](C)[C@H]3CC[C@@H](c4ccnc5ccc(F)cc54)CC3)cn2n1]

Intermediate 30A: (R)-2-((cis)-4-(6-fluoroquinolin-4-yl)cyclohexyl)-N-methoxy-N-methylpropanamide Preparation 1K (500 mg, 1.659 mmol) was dissolved in thionyl chloride (0.605 ml, 8.30 mmol) and DMF (0.064 ml, 0.830 mmol) was added. Reaction stirred at rt. After 1 hour, reaction concentrated in vacuo, taken up in toluene, concentrated again and placed on high vacuum to remove excess thionyl chloride. After 15 minutes, the crude acyl chloride was taken up in ACN (16.600 ml) and added to a solution of N,O-dimethylhydroxylamine hydrochloride (324 mg, 3.32 mmol) in ACN (16.600 ml) and TEA (1.156 ml, 8.30 mmol) at 0° C. After 30 minutes, the reaction was concentrated in vacuo. The resulting crude residue was purified via silica gel column chromatography give Intermediate 30A (487 mg, 1.414 mmol, 85% yield). LC-MS Anal. Calc'd for $C_{20}H_{25}FN_2O_2$ 344.19, found [M+H] 345.3 $T_r$=0.68 min (Method A).

Intermediate 30B: (R)-3-((cis)-4-(6-fluoroquinolin-4-yl)cyclohexyl)butan-2-one

Intermediate 30A (478 mg, 1.388 mmol) was taken up in dry THF (2776 µl) under an atmosphere of nitrogen and cooled to 0° C. over an ice bath. Methylmagnesium bromide (3M solution in ether) (1.0 mL, 3.00 mmol) was added dropwise and reaction was stirred at 0° C. After 1 hour, another 0.5 eq of MeMgBr added. After another hours, the reaction was quenched by the addition of 1 M HCl, basified with 1N NaOH and extracted with EtOAc. The organic extracts were dried over $Na_2SO_4$, filtered, and concentrated in vacuo. The crude residue was purified via silica gel column chromatography to give Intermediate 30B (356 mg, 1.189 mmol, 86% yield). LC-MS Anal. Calc'd for $C_{19}H_{22}FNO$ 299.17, found [M+H] 300.2 $T_r$=0.71 min (Method A).

Intermediate 30C: (R)-1-bromo-3-((cis)-4-(6-fluoroquinolin-4-yl)cyclohexyl)butan-2-one Diisopropylamine (203 µl, 1.427 mmol) in dry THF (1189 µl) was cooled to −78° C. n-BuLi (571 µl, 1.427 mmol) (2.5 M in hexanes) was added dropwise. After 15 minutes, Intermediate 30B (356 mg, 1.189 mmol) was added and the reaction stirred at −78° C. for 40 minutes. TMS-Cl (274 µl, 2.140 mmol) was added dropwise over 5 minutes and the reaction was stirred for another hour at −78° C. The reaction mixture was then poured into sat $NaHCO_3$ (50 mL) and extracted with EtOAc (100 mL). The extract was dried ($Na_2SO_4$) and concentrated in vacuo. The resultant residue was dissolved in anhydrous THF (12 mL) under a nitrogen atmosphere and cooled to 0° C. Sodium bicarbonate (125 mg, 1.486 mmol) was added followed by NBS (212 mg, 1.189 mmol) and reaction stirred at 0° C. for 90 minutes. Reaction quenched with $NaHCO_3$ and extracted with EtOAc. Organics dried with sodium sulfate, filtered, and concentrated in vacuo to give a brown oil that was ~20% Intermediate 30C (by LCMS) but mostly starting material. Yield of this crude mixture was (363 mg, 0.96 mmol, 81%) Crude was used directly subsequently. LC-MS Anal. Calc'd for $C_{19}H_{21}BrFNO$ 377.08, found [M+H] 378.0 $T_r$=0.78 min (Method A).

Example 30: 6-fluoro-4-((cis)-4-((R)-1-(6-methylimidazo[1,2-b]pyridazin-2-yl)ethyl)cyclohexyl)quinoline Crude Intermediate 30C (60 mg, 0.159 mmol) was taken up in EtOH in a pressure release vial and 6-methylpyridazin-3-amine (22.50 mg, 0.206 mmol) was added. The reaction was sealed and stirred at 80° C. for 1 hour. After 1 hour, the reaction was concentrated in vacuo, taken up in DMF, filtered, and purified via HPLC to give Example 30 (4.0 mg, 7% yield). LC-MS Anal. Calc'd for $C_{24}H_{25}FN_4$ 388.21, found [M+H] 389.1 $T_r$=0.64 min (Method A). $^1$H NMR (500 MHz, DMSO-$d_6$) δ: 8.92 (br. s., 1H), 8.43 (s, 1H), 8.22 (d, J=9.3 Hz, 1H), 8.09-8.17 (m, 1H), 8.05 (d, J=8.8 Hz, 1H), 7.68-7.77 (m, 2H), 7.55 (d, J=9.3 Hz, 1H), 3.45 (m., 1H), 2.60 (s, 3H), 2.05 (br. s., 2H), 1.69-1.94 (m, 5H), 1.64 (t, J=13.1 Hz, 1H), 1.56 (d, J=12.3 Hz, 1H), 1.27-1.37 (m, 4H).

Example 31

6-fluoro-4-((cis)-4-((R)-1-(imidazo[1,2-b]pyridazin-2-yl)ethyl)cyclohexyl)quinoline

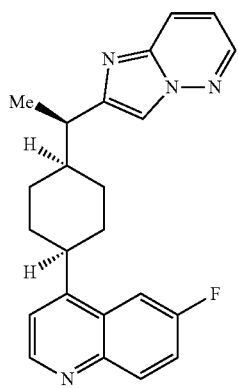 [SMILES: C[C@@H](c1cn2ncccc2n1)[C@H]1CC[C@@H](c2ccnc3ccc(F)cc32)CC1]

Example 31: 6-fluoro-4-((cis)-4-((R)-1-(imidazo[1,2-b]pyridazin-2-yl)ethyl)cyclohexyl)quinoline Example 31 was made using the analogous procedure to make Example 30 from Intermediate 30C and pyridazin-3- amine. LC-MS Anal. Calc'd for $C_{23}H_{23}FN_4$ 374.19, found [M+H] 375.1 $T_r$=0.63 min (Method A). $^1$H NMR (500 MHz, DMSO-$d_6$) δ: 8.83 (d, J=4.3 Hz, 1H), 8.41 (d, J=3.4 Hz, 1H), 8.16 (s, 1H), 8.08 (dd, J=9.2, 5.8 Hz, 1H), 8.00 (d, J=8.8 Hz, 1H), 7.95 (dd, J=11.0, 2.4 Hz, 1H), 7.65 (td, J=8.6, 2.6 Hz, 1H), 7.59 (d, J=4.6 Hz, 1H), 7.14 (dd, J=9.2, 4.6 Hz, 1H), 3.46 (m., 1H), 1.99-2.10 (m, 2H), 1.68-1.95 (m, 5H), 1.50-1.62 (m, 2H), 1.26-1.36 (m, 4H)

Example 32

4-((1S,4s)-4-((R)-1-(6-chloro-1H-benzo[d]imidazol-2-yl)but-3-en-1-yl)cyclohexyl)-6-fluoroquinoline

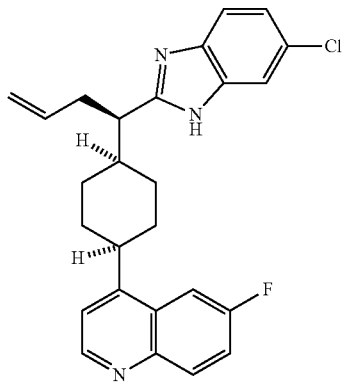 [SMILES: C=CC[C@@H](c1nc2ccc(Cl)cc2[nH]1)[C@H]1CC[C@@H](c2ccnc3ccc(F)cc32)CC1]

Intermediate 32A. (R)-3-((R)-2-((cis)-4-(6-fluoro-quinolin-4-yl)cyclohexyl)pent-4-enoyl)-4-phenyloxazolidin-2-one

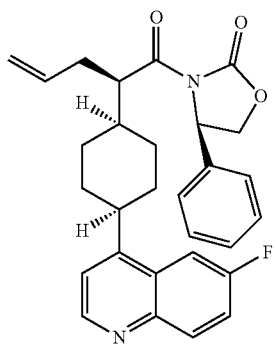 [SMILES: C=CC[C@@H](C(=O)N1C(=O)OC[C@H]1c1ccccc1)[C@H]1CC[C@@H](c2ccnc3ccc(F)cc32)CC1]

To a solution of Preparation 1J (50 mg, 0.116 mmol, reference example 40 in docket 12547) in THF (2 mL) at −40° C. was added NaHMDS (1M in THF) (0.139 mL, 0.139 mmol) drop wise. The mixture was stirred at −40° C. to −30° C. for 15 min. Then 3-bromoprop-1-ene (28.0 mg, 0.231 mmol) in THF (0.5 mL) was added drop wise. The reaction was stirred at −20° C. for 16 h. The reaction was quenched at −20° C. by pouring it into saturated NH$_4$Cl solution. The aqueous was extracted with EtOAc. The organic was washed with brine, dried over MgSO$_4$, filtered and concentrated to give a crude material. This crude material was added MeOH and filtered to remove the solid. The filtrate was purified with prep HPLC (Phen Luna 5u 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm. Combined fractions (tr=9.428 min) containing the product. After concentration Intermediate 32A (25 mg, 0.052 mmol, 44.8% yield) was obtained as white solid. $^1$H NMR (400 MHz, CHLOROFORM-d) δ 9.12 (d, J=5.5 Hz, 1H), 8.64 (dd, J=9.3, 5.0 Hz, 1H), 8.01-7.89 (m, 2H), 7.89-7.75 (m, 1H), 7.47-7.31 (m, 5H), 5.62-5.45 (m, 2H), 4.84-4.76 (m, 1H), 4.76-4.68 (m, 1H), 4.68-4.52 (m, 1H), 4.36 (dd, J=9.0, 3.9 Hz, 1H), 3.55-3.33 (m, 1H), 2.49-2.35 (m, 1H), 2.33-2.21 (m, 2H), 2.12-1.97 (m, 2H), 1.93-1.65 (m, 6H) LC-MS: M+H=473.3 (tr=0.90 min) (Method A)

Intermediate 32B: (R)-2-((cis)-4-(6-fluoroquinolin-4-yl)cyclohexyl)pent-4-enoic acid

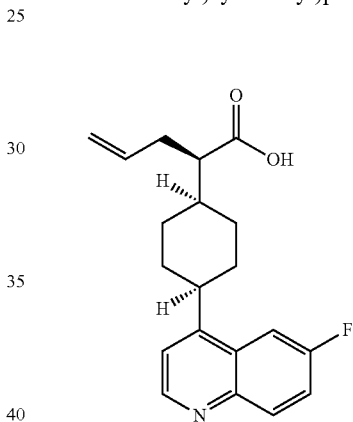

To a solution of Intermediate 32A (250 mg, 0.529 mmol) in THF (2 mL) at 0° C. was added 2.0 M LiOH in H$_2$O (0.476 mL, 0.952 mmol), followed by 30% H$_2$O$_2$ (0.360 mL, 3.17 mmol). The reaction was stirred at 0° C. for 10 min. Then it was warmed up to RT and stirred at RT for 16 h. The reaction was carefully quenched at 0° C. by addition of saturated Na$_2$SO$_3$. The pH was adjusted to 5~6 with 1N HCl and the mixture was extracted with EtOAc. The combined organics were dried over MgSO$_4$, filtered and concentrated. The crude material was purified with prep HPLC (Phen Luna 5u 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm, 32B (78 mg, 0.236 mmol, 44.6% yield) was obtained as white solid. $^1$H NMR (400 MHz, CHLOROFORM-d) δ 9.22 (br. s., 1H), 8.63 (dd, J=9.0, 5.0 Hz, 1H), 7.98-7.75 (m, 4H), 5.85 (dd, J=16.9, 9.7 Hz, 1H), 5.25-5.03 (m, 2H), 3.50 (br. s., 1H), 2.89-2.75 (m, 1H), 2.54-2.32 (m, 2H), 2.16 (d, J=10.1 Hz, 1H), 2.06 (d, J=13.2 Hz, 1H), 2.01-1.71 (m, 6H) LC-MS: M+H=328 (tr=0.69 min) (Method A)

Intermediate 32C: (R)—N-(2-amino-4-chlorophenyl)-2-((cis)-4-(6-fluoroquinolin-4-yl)cyclohexyl)pent-4-enamide

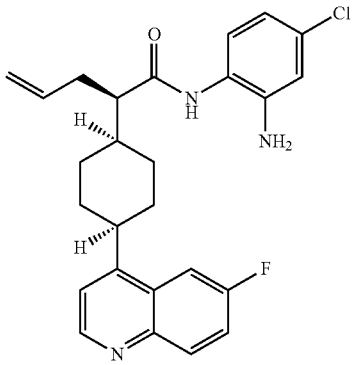 [SMILES: C=CC[C@@H](C(=O)Nc1ccc(Cl)cc1N)[C@H]1CC[C@@H](c2ccnc3ccc(F)cc32)CC1]

To a solution of Intermediate 32B (10 mg, 0.031 mmol) in CH$_2$Cl$_2$ (0.5 mL) at RT was added oxalyl chloride (15.51 mg, 0.122 mmol) dropwise followed by 1 drop of DMF. The reaction was stirred at RT for 2h. The solvent was removed and the residue was dried under vacuum pump for 2h. To this (R)-2-((1s,4S)-4-(6-fluoroquinolin-4-yl)cyclohexyl)pent-4-enoyl chloride (11 mg, 0.032 mmol) in THF (0.5 mL) at RT was added 4-chlorobenzene-1,2-diamine (9.07 mg, 0.064 mmol), followed by Hunig's Base (0.017 mL, 0.095 mmol). The reaction was stirred at RT for 3h. LCMS shows SM consumed and new peak at rt=0.76 min with M+1 of desired. The reaction was diluted with MeOH and purified with prep HPLC (Phen Luna 5u 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm. Intermediate 32C (11 mg, 0.015 mmol, 48.4% yield) was obtained as light brown solid. LC-MS: M+H=452.3 (tr=0.80 min) (Method A)

Example 32: 4-((1S,4s)-4-((R)-1-(6-chloro-1H-benzo[d]imidazol-2-yl)but-3-en-1-yl)cyclohexyl)-6-fluoroquinoline To a solution of 32C (10 mg, 0.022 mmol) in toluene (0.5 mL) at RT was added p-toluenesulfonic acid (19.05 mg, 0.111 mmol). The reaction was stirred at 115° C. for 16h. LCMS after 16h shows starting material consumed and new peak with M+1 of desired. Reaction concentrated, taken up in 2 mL MeOH, filtered and was submitted for Single Compound Purification. The crude material was purified via preparative LC/MS with the following conditions: Column: XBridge C18, 19×200 mm, 5-µm particles: Mobile Phase A: 5:95 acetonitrile:water with 10-mM ammonium acetate; Mobile Phase B: 95:5 acetonitrile:water with 10-mM ammonium acetate: Gradient: 40-80% B over 20 minutes, then a 5-minute hold at 100% B: Flow: 20 mL/min. Fractions containing the desired product were combined and dried via centrifugal evaporation to afford Example 32 (3.2 mg, 0.0073 mmol, 33%). $^1$H NMR (500 MHz, DMSO-d$_6$) δ 8.87 (d, J=4.4 Hz, 1H), 8.09 (dd, J=9.0, 5.9 Hz, 1H), 7.97 (d, J=10.8 Hz, 1H), 7.72-7.64 (m, 1H), 7.63-7.52 (m, 2H), 7.49 (br. s., 1H), 7.15 (d, J=7.8 Hz, 1H), 5.75-5.55 (m, 2H), 3.96 (t, J=10.1 Hz, 1H), 2.30 (br. s., 1H), 2.01-1.90 (m, 1H), 1.86 (br. s., 1H), 1.84-1.72 (m, 3H), 1.72-1.59 (m, 4H), 1.54 (d, J=12.0 Hz, 1H), 1.15 (d, J=11.5 Hz, 1H): LC-MS: M+H=434.3 (tr=1.34 min) (Method B)

Example 33

(±)-Cis and trans-4-(4-(1-(6-chloro-1H-benzo[d]imidazol-2-yl)-3,3,3-trifluoropropyl)cyclohexyl)-6-fluoroquinoline

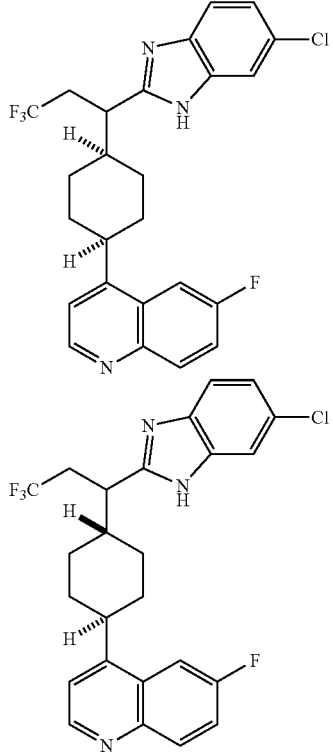

Preparation 33A. E)-ethyl 4,4,4-trifluoro-2-(4-(6-fluoroquinolin-4-yl)cyclohex-3-en-1-yl)but-2-enoate A solution of Intermediate 15F (0.500 g, 1.596 mmol) and DMPU (0.192 ml, 1.596 mmol) in THF (10.64 ml) was cooled to −78° C. To this solution was added KHMDS (1M solution in THF) (3.35 ml, 3.35 mmol). After 1.75 h, 2,2,2-trifluoroethyl trifluoromethanesulfonate (0.463 ml, 3.35 mmol) was added dropwise. The reaction was covered with Al foil and stirred at −78° C. for 3.5 h, then allowed to warm to rt overnight. The reaction was quenched with a sat. aq. soln. of NH$_4$Cl and diluted with EtOAc. Layers were separated. The aqueous phase was extracted with EtOAc (2×). The organic phases were combined, dried over Na$_2$SO$_4$, filtered, and concentrated to afford an orange residue. Purification of the crude material by silica gel chromatography using an ISCO machine (40 g column, 40 mL/min, 0-50% EtOAc in hexanes over 21 min, t$_r$=14 min) gave (E)-ethyl 4,4,4-trifluoro-2-(4-(6-fluoroquinolin-4-yl)cyclohex-3-en-1-yl)but-2-enoate (0.109 g, 0.263 mmol, 16.50% yield) as a colorless residue.

ESI MS (M+H)+=394.1. HPLC Peak t$_r$=0.93 minutes. HPLC conditions: A.

Preparation 33B. ethyl 4,4,4-trifluoro-2-(4-(6-fluoroquinolin-4-yl)cyclohexyl)butanoate To a solution of Intermediate 33A (0.109 g, 0.277 mmol) in MeOH (1.385 ml) was added ammonium formate (0.087 g, 1.385 mmol) followed by Pd/C (7.96 mg, 0.075 mmol). The reaction was heated at 70° C. for 1 h. The reaction was filtered through Celite, the filter cake washed with MeOH, and the filtrate was concentrated. The crude material was re-dissolved in MeOH and ammonium formate (0.087 g, 1.385 mmol) and Pd/C (7.96 mg, 0.075 mmol) were added. The reaction was heated at 70° C. for 2.5 h. The reaction was filtered through Celite and the filter cake washed with $CH_2Cl_2$. The filtrate was concentrated. The crude material was taken up in $CH_2Cl_2$ and washed with a sat. aq. solution of $NaHCO_3$ (1×). The organic phase was dried over $Na_2SO_4$, filtered, and concentrated to afford the title compound as a colorless residue. ESI MS (M+H)+=398.3. HPLC Peak $t_r$=0.85 minutes. HPLC conditions: Method A.

Preparation 33C. 4,4,4-trifluoro-2-(4-(6-fluoroquinolin-4-yl)cyclohexyl)butanoic acid To a solution Intermediate 33B (0.0336 g, 0.085 mmol) in THF (0.068 ml), MeOH (0.034 ml), and water (0.068 ml) was added lithium hydroxide (0.020 g, 0.845 mmol). The reaction was heated at 80° C. for 1 h, then allowed to cool to rt. The reaction was adjusted to pH 7 with 1N HCl, then diluted with EtOAc. Layers were separated. The aqueous phase was extracted with EtOAc (5×). The organic phases were combined, dried over $Na_2SO_4$, filtered, and concentrated to afford the title compound as a colorless residue. ESI MS (M+H)+=370.2. HPLC Peak $t_r$=0.71 minutes. HPLC conditions: Method A.

Example 33. (±)-Cis and trans-4-(4-(1-(6-chloro-1H-benzo[d]imidazol-2-yl)-3,3,3-trifluoropropyl)cyclohexyl)-6-fluoroquinoline Intermediate 33C (0.0216 g, 0.058 mmol) was dissolved in thionyl chloride (0.043 ml, 0.585 mmol) and DMF (2.264 µl, 0.029 mmol) was added. The reaction was stirred at rt. After 1 h, the reaction was concentrated, taken up in toluene, concentrated again, and placed under high vacuum. The crude acyl chloride taken up in Acetonitrile (0.292 ml) and the solution was cooled to 0° C., then 4-chlorobenzene-1,2-diamine (0.017 g, 0.117 mmol) and triethylamine (0.041 ml, 0.292 mmol) were added. The reaction was allowed to warm to rt. The reaction was diluted with water and extracted with EtOAc (3×). The organics were combined, dried over $Na_2SO_4$, filtered, and concentrated to afford a brown residue. The crude material was taken up in toluene (0.292 ml) and p-toluenesulfonic acid monohydrate (0.056 g, 0.292 mmol) was added. The reaction was heated at 110° C. overnight, then allowed to cool to it. The solvent was evaporated and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-43% B over 25 minutes, then a 2-minute hold at 43% B; Flow: 20 mL/min. Fractions containing the desired product were combined and dried via centrifugal evaporation to afford the title compound as a mixture of 4 isomers (8.5 mg, 29%). ESI MS (M+H)+=476.2. HPLC Peak $t_r$=2.062 minutes. Purity=96%. HPLC conditions: Method B.

Example 34

(±)-Cis and trans-(4-(1-(6-chloro-1H-benzo[d]imidazol-2-yl)ethyl)cyclohexyl)-1,8-naphthyridine

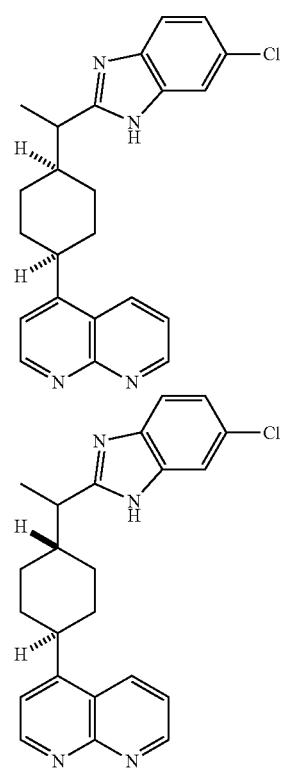

Preparation 34A. 2-(4-(1,8-naphthyridin-4-yl)cyclohexyl)propanoic acid

To a solution of ethyl 2-(4-(1,8-naphthyridin-4-yl)cyclohexyl)propanoate (0.202 g, 0.647 mmol) in THF (0.517 ml), MeOH (0.259 ml), and water (0.517 ml) was added lithium hydroxide (0.155 g, 6.47 mmol). The reaction was heated at 80° C. for 1 h, then allowed to cool to rt. The reaction was adjusted to pH 7 with 1N HCl, then diluted with EtOAc. Layers were separated. The aqueous phase was extracted with EtOAc (5×). The organic phases were combined, dried over $Na_2SO_4$, filtered, and concentrated to afford the title compound as a yellow foam. ESI MS (M+H)+=285.1. HPLC Peak $t_r$=0.56 minutes. HPLC conditions: A. Example 34. (+/−)-Cis and trans-(4-(1-(6-chloro-1H-benzo[d]imidazol-2-yl)ethyl)cyclohexyl)-1,8-naphthyridine 2-(4-(1,8-naphthyridin-4-yl)cyclohexyl)propanoic acid (0.1356 g, 0.477 mmol) was dissolved in thionyl chloride (0.348 ml, 4.77 mmol) and DMF (0.018 ml, 0.238 mmol) was added. The reaction was stirred at rt. After 1 h, the reaction was concentrated, taken up in toluene, concentrated again, and placed under high vacuum. The crude acyl chloride taken up in acetonitrile (2.384 ml) and the solution was cooled to 0° C., then 4-chlorobenzene-1,2-diamine (0.136 g, 0.954 mmol) and triethylamine (0.332 ml, 2.384 mmol) were added. The reaction was allowed to warm to rt. The reaction was diluted with water and extracted with EtOAc (3×). The organics were combined, dried over $Na_2SO_4$, filtered, and concentrated to afford a brown residue. The crude material was taken up in toluene (2.384 ml) and p-toluenesulfonic acid monohydrate (0.454 g, 2.384 mmol) was added. The reaction was heated at 110° C. for 3 h, then allowed to cool to rt. The crude material was purified via preparative LC/MS with the following conditions: Column: XBridge C18, 19×200 mm, 5-μm particles: Mobile Phase A: 5:95 acetonitrile:water with 10-mM ammonium acetate; Mobile Phase B: 95:5 acetonitrile:water with 10-mM ammonium acetate: Gradient: 20-70% B over 25 minutes, then a 5-minute hold at 100% B: Flow: 20 mL/min. Fractions containing the desired product were combined and dried via centrifugal evaporation. The material was further purified via preparative LC/MS with the following conditions: Column: XBridge C18, 19×200 mm, 5-μm particles: Mobile Phase A: 5:95 acetonitrile:water with 0.1% trifluoroacetic acid; Mobile Phase B: 95:5 acetonitrile:water with 0.1% trifluoroacetic acid; Gradient: 0-25% B over 19 minutes, then a 4-minute hold at 100% B; Flow: 20 mL/min. Fractions containing the desired product were combined and dried via centrifugal evaporation to afford the title compound (22.5 mg, 12%). ESI MS (M+H)+=391.2. HPLC Peak $t_r$=1.679 minutes. Purity=100%. HPLC conditions: Method B.

Example 35

(4-(4-(1-(6-chloro-1H-benzo[d]imidazol-2-yl)ethyl)cyclohexyl)-1,8-naphthyridine, Homochiral, Absolute and Relative Stereochemistry not Determined

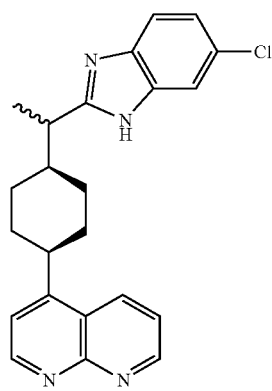

-continued

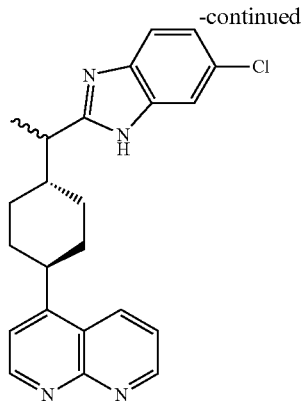

Approximately 21.2 mg of diastereomeric and racemic mixture was resolved. The isomeric mixture was purified via preparative SFC with the following conditions: Column: WhelkO1-Kromasil, 25×3 cm ID, 5-μm particles; Mobile Phase A: 80/20 $CO_2$/MeOH with 0.1% DEA; Detector Wavelength: 220 nm; Flow: 85 mL/min. The fractions ("Peak-1" tr=28.078 min, "Peak-2" $t_r$=29.448 min; analytical conditions: Column: WhelkO1-Kromasil, 250×4.6 mm ID, 5-μm particles; Mobile Phase A: 80/20 $CO_2$/MeOH with 0.1% DEA; Flow: 2.0 mL/min) were collected in MeOH. The stereoisomeric purity of peak 1 and peak 2 was estimated to be greater than 98% based on the prep-SFC chromatograms. Each enantiomer was further purified via preparative LC/MS:

Example 35-1, First eluting isomer: The crude material was purified via preparative LC/MS with the following conditions: Column: XBridge C18, 19×200 mm, 5-μm particles: Mobile Phase A: 5:95 acetonitrile:water with 10-mM ammonium acetate; Mobile Phase B: 95:5 acetonitrile:water with 10-mM ammonium acetate; Gradient: 20-70% B over 25 minutes, then a 5-minute hold at 100% B; Flow: 20 mL/min. Fractions containing the desired product were combined and dried via centrifugal evaporation to afford Isomer 1 (1.7 mg, 1%). ESI MS (M+H)+=391.1. HPLC Peak $t_r$=1.595 minutes. Purity=95%. HPLC conditions: B. Absolute stereochemistry not determined.

Example 35-2, Second eluting isomer: The crude material was purified via preparative LC/MS with the following conditions: Column: XBridge C18, 19×200 mm, 5-μm particles: Mobile Phase A: 5:95 acetonitrile:water with 10-mM ammonium acetate; Mobile Phase B: 95:5 acetonitrile:water with 10-mM ammonium acetate; Gradient: 20-70% B over 25 minutes, then a 5-minute hold at 100% B; Flow: 20 mL/min. Fractions containing the desired product were combined and dried via centrifugal evaporation to afford Isomer 2 (1.8 mg, 1%). ESI MS (M+H)+=391.2. HPLC Peak $t_r$=1.696 minutes. Purity=99%. HPLC conditions: B. Absolute stereochemistry not determined.

Example 36

(+/−)-Cis and trans-6-chloro-2-(1-(4-(2-(trifluoromethyl)pyridin-4-yl)cyclohexyl)propyl)-1H-benzo[d]imidazole

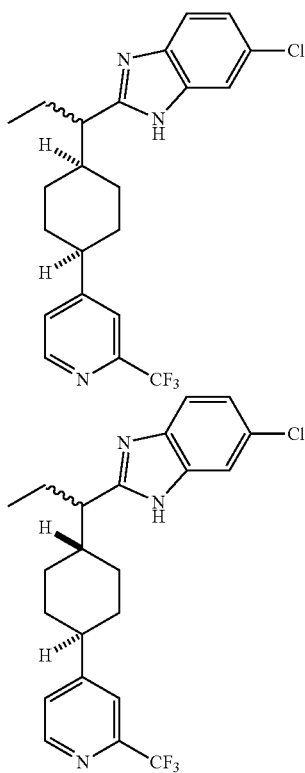

Preparation 36A. ethyl 2-(4-(2-(trifluoromethyl)pyridin-4-yl)cyclohex-3-en-1-yl)acetate A mixture of 4-bromo-2-(trifluoromethyl)pyridine (1.170 ml, 8.85 mmol), Intermediate 15E (2.68 g, 9.12 mmol), Na$_2$CO$_3$ (3.75 g, 35.4 mmol), and Pd(Ph$_3$P)$_4$ (0.511 g, 0.442 mmol) in dioxane (82 ml) and water (27.3 ml) was heated at 100° C. overnight. The reaction was quenched with water and diluted with EtOAc. Layers were separated. The aqueous phase was extracted with EtOAc (3×). The organics were combined, dried over Na$_2$SO$_4$, filtered, and concentrated to afford a yellow residue. Purification of the crude material by silica gel chromatography using an ISCO machine (80 g column, 60 mL/min, 0-20% EtOAc in hexanes over 16.5 min, t$_r$=11 min) gave ethyl 2-(4-(2-(trifluoromethyl)pyridin-4-yl)cyclohex-3-en-1-yl)acetate (2.336 g, 7.46 mmol, 84% yield) as a colorless residue. ESI MS (M+H)+=314.1. HPLC Peak t$_r$=1.05 minutes. HPLC conditions: Method A.

Preparation 36B. ethyl 2-(4-(2-(trifluoromethyl)pyridin-4-yl)cyclohex-3-en-1-yl)butanoate (A solution of ethyl 2-(4-(2-(trifluoromethyl)pyridin-4-yl)cyclohex-3-en-1-yl)acetate (2.191 g, 6.99 mmol) and DMPU (0.843 ml, 6.99 mmol) in THF (46.6 ml) was cooled to −78° C. To this solution was added KHMDS (1M solution in THF) (14.69 ml, 14.69 mmol). After 1 h, ethyl iodide (1.187 ml, 14.69 mmol) was added dropwise. The reaction was covered with Al foil and stirred at −78° C. for 3.5 h, then allowed to warm to rt overnight. The reaction was quenched with a sat. aq. soln. of NH$_4$Cl and diluted with EtOAc. Layers were separated. The aqueous phase was extracted with EtOAc (2×). The organic phases were combined, dried over Na$_2$SO$_4$, filtered, and concentrated to afford an orange residue. Purification of the crude material by silica gel chromatography using an ISCO machine (80 g column, 60 mL/min, 0-18% EtOAc in hexanes over 19 min, t$_r$=14 min) gave ethyl 2-(4-(2-(trifluoromethyl)pyridin-4-yl)cyclohex-3-en-1-yl)butanoate (0.836 g, 2.448 mmol, 35% yield) as a colorless residue. ESI MS (M+H)+=342.2. HPLC Peak t$_r$=1.14 minutes. HPLC conditions: A.

Preparation 36C. ethyl 2-(4-(2-(trifluoromethyl)pyridin-4-yl)cyclohexyl)butanoate To a solution of ethyl 2-(4-(2-(trifluoromethyl)pyridin-4-yl)cyclohex-3-en-1-yl)butanoate (0.884 g, 2.59 mmol) in MeOH (12.95 ml) was added ammonium formate (0.816 g, 12.95 mmol) followed by Pd/C (0.074 g, 0.699 mmol). The reaction was heated at 70° C. for 1 h. The reaction was filtered through Celite and the filter cake washed with CH$_2$Cl$_2$. The filtrate was concentrated. The crude material was taken up in CH$_2$Cl$_2$ and washed with a sat. aq. solution of NaHCO$_3$ (1×). The organic phase was dried over Na$_2$SO$_4$, filtered, and concentrated to afford the title compound as a colorless residue. ESI MS (M+H)+=344.3. HPLC Peak t$_r$=1.12 minutes. HPLC conditions: A.

Preparation 36D. 2-(4-(2-(trifluoromethyl)pyridin-4-yl)cyclohexyl)butanoic acid To a solution of ethyl 2-(4-(2-(trifluoromethyl)pyridin-4-yl)cyclohexyl)butanoate (0.729 g, 2.123 mmol) in THF (4.25 ml). MeOH (2.123 ml), and water (4.25 ml) was added lithium hydroxide (0.763 g, 31.8 mmol). The reaction was heated at 80° C. overnight, then allowed to cool to rt. Additional LiOH was added (0.381 mg, 15.9 mmol) and the reaction was heated overnight again. The reaction was adjusted to pH 7 with 1N HCl, then diluted with EtOAc. Layers were separated. The aqueous phase was extracted with EtOAc (5×). The organic phases were combined, dried over Na$_2$SO$_4$, filtered, and concentrated to afford the title compound as a yellow residue. ESI MS (M+H)+=316.4. HPLC Peak t$_r$=0.95 minutes. HPLC conditions: A.

Example 36. (+/−)-Cis and trans-6-chloro-2-(1-(4-(2-(trifluoromethyl)pyridin-4-yl)cyclohexyl)propyl)-1H-benzo[d]imidazole 2-(4-(2-(trifluoromethyl)pyridin-4-yl)cyclohexyl)butanoic acid (0.1086 g, 0.344 mmol) was dissolved in thionyl chloride (0.251 ml, 3.44 mmol) and DMF (0.013 ml, 0.172 mmol) was added. The reaction was stirred at it. After 1 h, the reaction was concentrated, taken up in toluene, concentrated again, and placed under high vacuum. The crude acyl chloride taken up in acetonitrile (1.722 ml) and the solution was cooled to 0° C., then 4-chlorobenzene-1,2-diamine (0.098 g, 0.689 mmol) and triethylamine (0.240 ml, 1.722 mmol) were added. The reaction was allowed to warm to rt. The reaction was diluted with water and extracted with EtOAc (3×). The organics were combined, dried over Na$_2$SO$_4$, filtered, and concentrated to afford a brown residue. The crude material was taken up in toluene (1.722 ml) and p-toluenesulfonic acid monohydrate (0.328 g, 1.722 mmol) was added. The reaction was heated at 110° C. for 8 h, then allowed to cool to rt. The solvent was evaporated and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford the title compound (66.5 mg, 99%). ESI MS (M+H)+= 422.2. HPLC Peak $t_r$=2.077 minutes. Purity=99%. HPLC conditions: Method B.

Example 37

4-(4-(1-(6-chloro-1H-benzo[d]imidazol-2-yl)ethyl)cyclohexyl)-1,8-naphthyridine, Homochirl, Absolute and Relative Stereochemsitry Undetermined

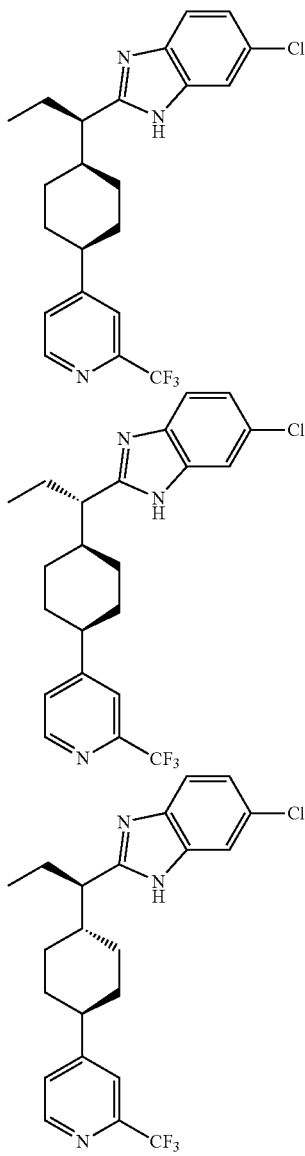

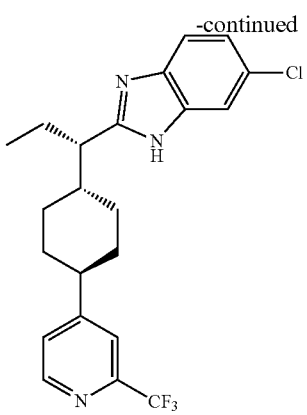

Approximately 68.4 mg of diastereomeric and racemic mixture was resolved. The isomeric mixture was purified via preparative SFC with the following conditions: Column: Chiral AD, 25×3 cm ID, 5-μm particles; Mobile Phase A: 88/12 CO$_2$/MeOH: Detector Wavelength: 220 nm: Flow: 85 mL/min. The fractions ("Peak-1" $t_r$=4.205 min, "Peak-2" tr=4.677 min, "Peak-3" $t_r$=5.792 min, "Peak-4" $t_r$=6.848 min; analytical conditions: Column: Chiral AD, 250×4.6 mm ID, 5-μm particles; Mobile Phase A: 85/15 CO$_2$/MeOH; Flow: 2.0 mL/min) were collected in MeOH. The stereoisomeric purity of each peak was estimated to be greater than 96% based on the prep-SFC chromatograms. Each enantiomer was further purified via preparative LC/MS:

Example 37-1, First eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford Isomer 1 (4.1 mg, 3%). ESI MS (M+H)+=422.2. HPLC Peak $t_r$=2.162 minutes. Purity=98%. HPLC conditions: B. Absolute stereochemistry not determined.

Example 37-2, Second eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate: Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford Isomer 2 (3.5 mg, 3%). ESI MS (M+H)+=422.2. HPLC Peak $t_r$=2.164 minutes. Purity=99%. HPLC conditions: B. Absolute stereochemistry not determined.

Example 37-3, Third eluting isomer: The crude material was purified via preparative LC/MS with the following conditions: Column: XBridge C18, 19×200 mm, 5-μm particles: Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford Isomer 3 (24.1 mg, 16%). ESI MS (M+H)+=422.2. HPLC Peak $t_r$=2.160 minutes. Purity=97%. HPLC conditions: B. Absolute stereochemistry not determined.

Example 37-4, Fourth eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford Isomer 4 (25.8 mg, 17%). ESI MS (M+H)+=422.2. HPLC Peak $t_r$=2.161 minutes. Purity=94%. HPLC conditions: B. Absolute stereochemistry not determined.

Example 38

(±)-Cis and trans-6-chloro-2-(1-(4-(2-(trifluoromethyl)pyridin-4-yl)cyclohexyl)ethyl)-1H-benzo[d]imidazole

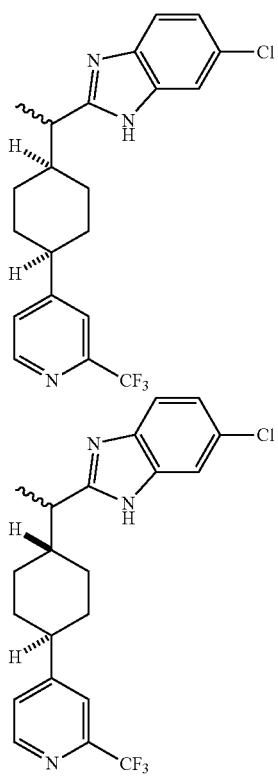

Preparation 38A. ethyl 2-(4-(2-(trifluoromethyl)pyridin-4-yl)cyclohex-3-en-1-yl)acetate A mixture of 4-bromo-2-(trifluoromethyl)pyridine (1.5 mL, 11.35 mmol), ethyl 2-(4-(4,4,5,5-tetramethyl-1,3,2-dioxaborolan-2-yl)cyclohex-3-en-1-yl)acetate (3.44 g, 11.69 mmol), $Na_2CO_3$ (4.81 g, 45.4 mmol), and $Pd(Ph_3P)_4$ (0.656 g, 0.567 mmol) in dioxane (105 mL) and water (35.0 mL) was heated at 100° C. overnight. The reaction was quenched with water and diluted with EtOAc. Layers were separated. The aqueous phase was extracted with EtOAc (3×). The organics were combined, dried over $Na_2SO_4$, filtered, and concentrated to afford a yellow residue. Purification of the crude material by silica gel chromatography using an ISCO machine (80 g column, 60 mL/min, 045% EtOAc in hexanes over 27 min, $t_r$=15, 23 min) gave ethyl 2-(4-(2-(trifluoromethyl)pyridin-4-yl)cyclohex-3-en-1-yl)acetate (2.7477 g, 8.33 mmol, 73.4% yield) as a colorless residue. ESI MS (M+H)+=314.1. HPLC Peak $t_r$=1.03 minutes. HPLC conditions: A.

Preparation 38B. ethyl 2-(4-(2-(trifluoromethyl)pyridin-4-yl)cyclohex-3-en-1-yl)propanoate A solution of ethyl 2-(4-(2-(trifluoromethyl)pyridin-4-yl)cyclohex-3-en-1-yl)acetate (2.7477 g, 8.77 mmol) and DMPU (1.057 ml, 8.77 mmol) in THF (58.5 ml) was cooled to −78° C. To this solution was added KHMDS (1M solution in THF) (18.42 ml, 18.42 mmol). After 45 min, methyl iodide (1.152 ml, 18.42 mmol) was added dropwise. The reaction was covered with Al foil and stirred at −78° C. for 3.5 h, then allowed to warm to rt. The reaction was quenched with a sat. aq. soln. of $NH_4Cl$ and diluted with EtOAc. Layers were separated. The aqueous phase was extracted with EtOAc (2×). The organic phases were combined, dried over $Na_2SO_4$, filtered, and concentrated to afford an orange residue. Purification of the crude material by silica gel chromatography using an ISCO machine (80 g column, 60 mL/min, 0-25% EtOAc in hexanes over 19 min, $t_r$=10 min) gave ethyl 2-(4-(2-(trifluoromethyl)pyridin-4-yl)cyclohex-3-en-1-yl)propanoate (2.116 g, 5.82 mmol, 66.3% yield) as a colorless residue. ESI MS (M+H)+=329.2. HPLC Peak $t_r$=1.10 minutes. HPLC conditions: Method A.

Preparation 38C. ethyl 2-(4-(2-(trifluoromethyl)pyridin-4-yl)cyclohexyl)propanoate To a solution of ethyl 2-(4-(2-(trifluoromethyl)pyridin-4-yl)cyclohex-3-en-1-yl)propanoate (2.116 g, 6.46 mmol) in MeOH (32.3 ml) was added ammonium formate (2.038 g, 32.3 mmol) followed by Pd/C (0.186 g, 1.745 mmol). The reaction was heated at 70° C. for 1 h. The reaction was filtered through Celite and the filter cake washed with $CH_2Cl_2$. The filtrate was concentrated. The crude material was taken up in $CH_2C_2$ and washed with a sat. aq. solution of $NaHCO_3$ (1×). The organic phase was dried over $Na_2SO_4$, filtered, and concentrated to afford the title compound as a colorless residue. ESI MS (M+H)+=330.2. HPLC Peak $t_r$=1.08 minutes. HPLC conditions: Method A.

Preparation 38D. 2-(4-(2-(trifluoromethyl)pyridin-4-yl)cyclohexyl)propanoic acid To a solution of ethyl 2-(4-(2-(trifluoromethyl)pyridin-4-yl)cyclohexyl)propanoate (2.0177 g, 6.13 mmol) in THF (4.90 ml), MeOH (2.450 ml), and water (4.90 ml) was added lithium hydroxide (1.467 g, 61.3 mmol). The reaction was heated at 80° C. for 1 h, then allowed to cool to rt. The reaction was adjusted to pH 7 with 1N HCl, then diluted with EtOAc. Layers were separated. The aqueous phase was extracted with EtOAc (5×). The organic phases were combined, dried over $Na_2SO_4$, filtered, and concentrated to afford the title compound as a white foam. ESI MS (M+H)+=302.1. HPLC Peak $t_r$=0.90 minutes. HPLC conditions: Method A.

Example 38. (+/−)-Cis and trans-6-chloro-2-(1-(4-(2-(trifluoromethyl)pyridin-4-yl)cyclohexyl)ethyl)-1H-benzo[d]imidazole 2-(4-(2-(trifluoromethyl)pyridin-4-yl)cyclohexyl)propanoic acid (0.100 g, 0.332 mmol) was dissolved in thionyl chloride (0.242 mL, 3.32 mmol) and DMF (0.013 ml, 0.166 mmol) was added. The reaction was stirred at rt. After 1 h, the reaction was concentrated, taken up in toluene, concentrated again, and placed under high vacuum. The crude acyl chloride taken up in acetonitrile (1.659 mL) and the solution was cooled to 0° C., then 4-chlorobenzene-1,2-diamine (0.095 g, 0.664 mmol) and triethylamine (0.231 mL, 1.659 mmol) were added. The reaction was allowed to warm to rt. The reaction was diluted with water and extracted with EtOAc (3×). The organics were combined, dried over $Na_2SO_4$, filtered, and concentrated to afford a brown residue. The crude material was taken up in toluene (1.659 ml) and p-toluenesulfonic acid monohydrate (0.316 g, 1.659 mmol) was added. The reaction was heated at 110° C. for 8 h, then allowed to cool to rt. The solvent was evaporated and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate: Gradient: 40-80% B over 25 minutes, then a 5-minute hold at 100% B; Flow: 20 mL/min. Fractions containing the desired product were combined and dried via centrifugal evaporation to afford the title compound (39.6 mg, 28%). ESI MS (M+H)+ =408.1. HPLC Peak $t_r$=1.984 minutes. Purity=97%. HPLC conditions: B.

Example 39

6-chloro-2-(1-(4-(2-(trifluoromethyl)pyridin-4-yl) cyclohexyl)ethyl)-1H-benzo[d]imidazole (Homochiral, Absolute and Relative Stereochemistry Undetermined)

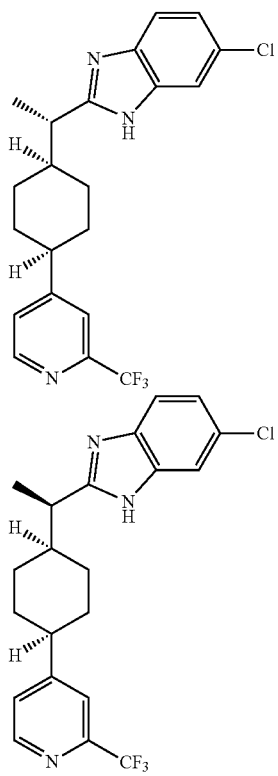

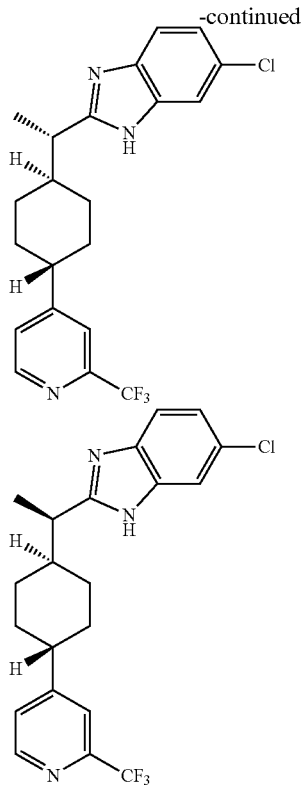

Approximately 41 mg of diastereomeric and racemic mixture was resolved. The isomeric mixture was purified via preparative SFC with the following conditions: Column: Whelk-O R,R Kromasil, 25×3 cm ID, 5-µm particles; Mobile Phase A: 85/15 $CO_2$/MeOH with 0.1% DEA; Detector Wavelength: 220 nm; Flow: 85 mL/min. The fractions ("Peak-1" $t_r$=9.88 min, "Peak-2" $t_r$=11.55 min, "Peak-3" $t_r$=12.99 min;) were collected in MeOH. Each enantiomer was further purified via preparative LC/MS:

Example 39-1, First eluting isomer: The crude material was purified via preparative LC/MS with the following conditions: Column: XBridge C18, 19×200 mm, 5-µm particles: Mobile Phase A: 5:95 acetonitrile:water with 10-mM ammonium acetate: Mobile Phase B: 95:5 acetonitrile:water with 10-mM ammonium acetate; Gradient: 40-80% B over 25 minutes, then a 5-minute hold at 100% B; Flow: 20 mL/min. Fractions containing the desired product were combined and dried via centrifugal evaporation to afford Isomer 1 (1.3 mg, 1%). ESI MS (M+H)+=408.2. HPLC Peak $t_r$=1.977 minutes. Purity=100%. HPLC conditions: B. Absolute stereochemistry not determined.

Example 39-2, Second eluting isomer: The crude material was purified via preparative LC/MS with the following conditions: Column: XBridge C18, 19×200 mm, 5-µm particles: Mobile Phase A: 5:95 acetonitrile:water with 10-mM ammonium acetate: Mobile Phase B: 95:5 acetonitrile:water with 10-mM ammonium acetate; Gradient: 40-80% B over 25 minutes, then a 5-minute hold at 100% B; Flow: 20 mL/min. Fractions containing the desired product were combined and dried via centrifugal evaporation to afford Isomer 2 (13.9 mg, 10%). ESI MS (M+H)+=408.2. HPLC Peak $t_r$=2.119 minutes. Purity=100%. HPLC conditions: B. Absolute stereochemistry not determined.

Example 39-3, Third eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 25 minutes, then a 5-minute hold at 100% B; Flow: 20 mL/min. Fractions containing the desired product were combined and dried via centrifugal evaporation to afford Isomer 3 (11.3 mg, 8%). ESI MS (M+H)+=407.9. HPLC Peak $t_r$=2.119 minutes. Purity=99%. HPLC conditions: B. Absolute stereochemistry not determined.

Examples 40-52

Using the methods described herein, additional compounds such as the following can be prepared.

| Ex. | Compound | Name |
|---|---|---|
| 40 | | 4-((1S,4s)-4-((R)-1-(5,6-difluoro-1H-benzo[d]imidazol-2-yl)ethyl)cyclohexyl)-6-fluoroquinoline |
| 41 | | 4-((1S,4s)-4-((R)-1-(4,5-difluoro-1H-benzo[d]imidazol-2-yl)ethyl)cyclohexyl)-6-fluoroquinoline |
| 42 | | 4-((1S,4s)-4-((R)-1-(6-chloro-5-fluoro-1H-benzo[d]imidazol-2-yl)ethyl)cyclohexyl)-6-fluoroquinoline |
| 43 | | 6-fluoro-4-((1S,4s)-4-((R)-1-(4,5,6,7-tetrafluoro-1H-benzo[d]imidazol-2-yl)ethyl)cyclohexyl)quinoline |
| 44 | | 4-((1S,4s)-4-((R)-1-(5,6-dichloro-1H-benzo[d]imidazol-2-yl)ethyl)cyclohexyl)-6-fluoroquinoline |

-continued

| Ex. | Compound | Name |
|---|---|---|
| 45 | | 6-fluoro-4-((1S,4s)-4-((R)-1-(5-(trifluoromethyl)-1H-benzo[d]imidazol-2-yl)ethyl)cyclohexyl)quinoline |
| 46 | | 4-((1S,4s)-4-((R)-1-(7-chloro-5-(trifluoromethyl)-1H-benzo[d]imidazol-2-yl)ethyl)cyclohexyl)-6-fluoroquinoline |
| 47 | | 4-((1S,4s)-4-((R)-1-(5,7-bis(trifluoromethyl)-1H-benzo[d]imidazol-2-yl)ethyl)cyclohexyl)-6-fluoroquinolme |

-continued

| Ex. | Compound | Name |
|---|---|---|
| 48 | | 6-fluoro-4-((1S,4s)-4-((R)-1-(5-(trifluoromethoxy)-1H-benzo[d]imidazol-2-yl)ethyl)cyclohexyl)quinoline |
| 49 | | 2-((R)-1-((1s,4S)-4-(6-fluoroquinolin-4-yl)cyclohexyl)ethyl)-1H-benzo[d]imidazole-5-carbonitrile |
| 50 | | methyl 2-((R)-1-((1s,4S)-4-(6-fluoroquinolin-4-yl)cyclohexyl)ethyl)-1H-benzo[d]imidazole-5-carboxylate |

| Ex. | Compound | Name |
|---|---|---|
| 51 | | 4-(((1s,4s)-4-(1-(6-chloro-1H-benzo[d]imidazol-2-yl)propyl)cyclohexyl)oxy)quinoline |
| 52 | | 4-(((1s,4s)-4-(1-(6-chloro-1H-benzo[d]imidazol-2-yl)propyl)cyclohexyl)oxy)quinoline |

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys. Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2: Calbiochem, EMD Biosciences, San Diego, Calif.). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses. Groups of 1,000-1,200 islets incubated for 24 h in Miami medium in the presence of cytokines can be harvested and sonicated in PBS as above, and 50 µg protein samples can be electrophoresed on 10% SDS-PAGE gels. COS7 cells (0.6×10$^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-STAT$_{1α}$ p91, and STAT$_{1α}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO. Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20: Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258

(Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

Evaluation of Biological Activity

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 µL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Assessment of inhibitor activity in HeLa cell-based indoleamine 2,3-dioxygenase (IDO) assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 µg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 µL of culture medium. After a further 48 hour incubation, 170 µL of supernatant was transferred from each well to a fresh 96-well plate. 12.1 µL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 µL of the supernatant was transferred from each well to afresh 96-well plate. 100 µl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided in FIG. 1, wherein potency levels are provided as follows: (Potency: IDO $IC_{50}$: A<0.1 µM; B<1 µM; C<10 µM).

Activity for compounds described herein is provided below, wherein potency levels are provided as follows: (Potency: IDO $IC_{50}$: A<0.05 µM; B<0.25 µM; C<2 µM)

Results of the IDO assays are shown in the table below.

| HEK Human IDO-1 | | |
| --- | --- | --- |
| Example No. | IDO1 HEK Human IC50 (uM) | IDO Hela IC50 (uM) |
| 1 | 0.0052 | 0.0047 |
| 2 | 0.0018 | 0.0011 |
| 3 | 0.0027 | 0.0015 |
| 4 | 0.0015 | |
| 5 | 0.1052 | |
| 6 | 0.0070 | 0.0045 |
| 7 | 0.0232 | 0.0301 |
| 8 | 0.7303 | |
| 9 | 0.2633 | |
| 10 | 0.1939 | |
| 11 | 0.0409 | 0.0409 |
| 12 | 0.1395 | |
| 13 | 0.0034 | |
| 13-1 | 0.0041 | 0.0057 |
| 13-2 | 0.0034 | 0.0089 |
| 14 | 0.3221 | |
| 15-1 | 0.0406 | |
| 15-2 | 0.1097 | |
| 15-3 | 0.0007 | 0.0035 |
| 15-4 | 0.0066 | 0.0095 |
| 16-1 | 0.0541 | |
| 16-2 | 0.0045 | 0.0057 |
| 17-1 | 0.0173 | 0.0169 |
| 17-2 | | |
| 18 | | 0.0121 |
| 19 | | 0.0038 |
| 20 | | 0.0058 |
| 20-1 | | 0.0060 |
| 20-2 | | 0.0045 |
| 21-1 | | 0.0020 |
| 21-2 | | 1.0000 |
| 21-3 | | 0.0051 |
| 21-4 | | 0.0897 |
| 22 | | 0.0037 |
| 22-1 | | 0.0024 |
| 22-2 | | 0.0991 |
| 23-1 | | 0.9982 |
| 23-2 | | 0.0032 |
| 24 | | 0.0075 |
| 24-1 | | 0.3751 |
| 24-2 | | 0.0027 |
| 25 | | 0.0449 |
| 25-1 | | 0.0102 |
| 25-2 | | 0.0229 |
| 26 | | 0.4587 |
| 27 | | 0.8356 |
| 28 | | 0.8336 |
| 29 | | 0.1426 |
| 30 | | 0.0966 |
| 31 | | 0.6066 |
| 32 | 0.0020 | 0.0028 |
| 33 | | 0.0075 |
| 34 | | 0.0681 |
| 35-1 | | 1.0000 |
| 35-2 | | 0.0143 |
| 36 | 0.0261 | |
| 37-1 | | 0.5843 |
| 37-2 | | 0.0174 |
| 37-3 | | 0.0858 |
| 38 | 0.0621 | |
| 39-1 | | 0.1702 |
| 39-2 | | 0.0754 |
| 39-3 | | 0.1174 |
| 40 | | 0.0027 |
| 41 | | 0.0034 |
| 42 | | 0.0037 |
| 43 | | 0.0035 |
| 44 | | 0.0055 |
| 45 | | 0.0031 |
| 46 | | 0.0122 |
| 47 | | 0.0456 |
| 48 | | 0.0107 |
| 49 | | 0.0134 |
| 50 | | 0.0021 |
| 51 | 1.0575 | |
| 52 | 0.6970 | |

What is claimed:
1. A compound that is
4-((1S,4s)-4-((R)-1-(1H-benzo[d]imidazol-2-yl)ethyl)cyclohexyl)-6-fluoroquinoline;
4-((1S,4s)-4-((R)-1-(6-chloro-1H-benzo[d]imidazol-2-yl)ethyl)cyclohexyl)-6-fluoroquinoline;
6-fluoro-4-((1S,4s)-4-((R)-1-(6-fluoro-1H-benzo[d]imidazol-2-yl)ethyl)cyclohexyl) quinolone;
6-((R)-1-((1s,4S)-4-(6-fluoroquinolin-4-yl)cyclohexyl)ethyl)-5H-[1,3]dioxolo[4',5':4,59 benzo[1,2-d]imidazole;
4-((1S,4s)-4-((R)-1-(1H-imidazo[4,5-c]pyridin-2-yl)ethyl)cyclohexyl)-6-fluoroquinoline;
4-((1S,4s)-4-((R)-1-(6-chloro-1H-imidazo[4,5-b]pyridin-2-yl)ethyl)cyclohexyl)-6-fluoroquinoline;
4-((1S,4s)-4-((R)-1-(1H-imidazo[4,5-b]pyridin-2-yl)ethyl)cyclohexyl)-6-fluoroquinoline;
6-chloro-N-((R)-1-((1s,4S)-4-(6-fluoroquinolin-4-yl)cyclohexyl)ethyl)benzo[d]thiazol-2-amine;
N-((R)-1-((1s,4S)-4-(6-fluoroquinolin-4-yl)cyclohexyl)ethyl)-6-methoxy-1H-benzo [d]imidazol-2-amine;
N-((R)-1-((1s,4S)-4-(6-fluoroquinolin-4-yl)cyclohexyl)ethyl)benzo[d]thiazol-2-amine;
6-chloro-N-((R)-1-((1s,4S)-4-(6-fluoroquinolin-4-yl)cyclohexyl)ethyl)benzo[d] oxazol-2-amine;
N-((R)-1-((1s,4S)-4-(6-fluoroquinolin-4-yl)cyclohexyl)ethyl)-1H-benzo[d]imidazol-2-amine;
4-(((1r,4r)-4-(1-(6-chloro-1H-benzo[d]imidazol-2-yl)propyl)cyclohexyl)oxy)quinolone;
4-(((1s,4s)-4-(1-(6-chloro-1H-benzo[d]imidazol-2-yl)propyl)cyclohexyl)oxy)quinolone;
4-(4-(1-(6-chloro-1H-benzo[d]imidazol-2-yl)propyl)cyclohexyl)-6-fluoroquinoline;
4-(4-(1-(6-chloro-1H-benzo[d]imidazol-2-yl)ethyl)cyclohexyl)quinolone;
4-(4-(1-(6-chloro-1H-benzo[d]imidazol-2-yl)-3-propyl)cyclohexyl)-6-(trifluoromethyl)quinolone;

(±)-4-((cis)-4-(1-(6-chloro-1H-benzo[d]imidazol-2-yl)-2-methoxyethyl)cyclohexyl)-6-(trifluoromethyl)quinolone;
(±)-4-((cis)-4-(1-(6-chloro-1H-benzo[d]imidazol-2-yl)-2-methoxyethyl)cyclohexyl)-6-fluoroquinoline;
(±)-4-(((trans)-4-(1-(6-chloro-1H-imidazo[4,5-b]pyridin-2-yl)-3-propyl)cyclohexyl) oxy)quinolone;
4-(4-(1-(6-chloro-1H-imidazo[4,5-b]pyridin-2-yl)propyl)cyclohexyl)-6-fluoroquinoline;
(±)-4-((cis)-4-(1-(6-chloro-1H-imidazo[4,5-b]pyridin-2-yl)propyl)cyclohexyl)-6-(trifluoromethyl)quinolone;
6-chloro-2-(1-((cis)-4-(2-fluoro-3-methylpyridin-4-yl)cyclohexyl)-3-propyl)-1H-benzo[d]imidazole;
(±)-6-chloro-2-(1-((cis)-4-(2-fluoro-3-methylpyridin-4-yl)cyclohexyl)-3-propyl)-1H-imidazo[4,5-b]pyridine;
(±)-6-chloro-2-(2-ethoxy-1-((cis)-4-(2-fluoro-3-methylpyridin-4-yl)cyclohexyl)ethyl) -1H-benzo[d]imidazole;
4-((cis)-4-((R)-1-([1,2,4]triazolo[4,3-a]pyridin-3-yl)ethyl)cyclohexyl)-6-fluoroquinoline;
6-fluoro-4-((cis)-4-((R)-1-(imidazo[1,5-a]pyridin-3-yl)ethyl)cyclohexyl)quinolone;
3-((R)-1-((cis)-4-(6-fluoroquinolin-4-yl)cyclohexyl)ethyl)quinazolin-4(3H)-one;
6-chloro-2-((R)-1-((cis)-4-(6-fluoroquinolin-4-yl)cyclohexyl)ethyl)quinazolin-4(3H)-one;
6-fluoro-4-((cis)-4-((R)-1-(6-methylimidazo[1,2-b]pyridazin-2-yl)ethyl)cyclohexyl) quinolone;
6-fluoro-4-((cis)-4-((R)-1-(imidazo[1,2-b]pyridazin-2-yl)ethyl)cyclohexyl)quinolone;
4-((1S,4s)-4-((R)-1-(6-chloro-1H-benzo[d]imidazol-2-yl)but-3-en-1-yl)cyclohexyl)-6-fluoroquinoline;
(+/−)-Cis and trans-4-(4-(1-(6-chloro-1H-benzo[d]imidazol-2-yl)-3,3,3-trifluoropropyl) cyclohexyl)-6-fluoroquinoline;
(+/−)-Cis and trans-(4-(1-(6-chloro-1H-benzo[d]imidazol-2-yl)ethyl)cyclohexyl)-1,8-naphthyridine;
(4-(4-(1-(6-chloro-1H-benzo[d]imidazol-2-yl)ethyl)cyclohexyl)-1,8-naphthyridine;
(+/−)-Cis and trans-6-chloro-2-(1-(4-(2-(trifluoromethyl) pyridin-4-yl)cyclohexyl)propyl) -1H-benzo[d]imidazole;
4-(4-(1-(6-chloro-1H-benzo[d]imidazol-2-yl)ethyl)cyclohexyl)-1,8-naphthyridine
(+/−)-Cis and trans-6-chloro-2-(1-(4-(2-(trifluoromethyl) pyridin-4-yl)cyclohexyl)ethyl) -1H-benzo[d]imidazole;
6-chloro-2-(1-(4-(2-(trifluoromethyl)pyridin-4-yl)cyclohexyl)ethyl)-1H-benzo [d]imidazole;
4-((1S,4s)-4-((R)-1-(5,6-difluoro-1H-benzo[d]imidazol-2-yl)ethyl)cyclohexyl)-6-fluoroquinoline;
4-((1S,4s)-4-((R)-1-(4,5-difluoro-1H-benzo[d]imidazol-2-yl)ethyl)cyclohexyl)-6-fluoroquinoline;
4-((1S,4s)-4-((R)-1-(6-chloro-5-fluoro-1H-benzo[d]imidazol-2-yl)ethyl)cyclohexyl)-6-fluoroquinoline;
6-fluoro-4-((1S,4s)-4-((R)-1-(4,5,6,7-tetrafluoro-1H-benzo[d]imidazol-2-yl)ethyl) cyclohexyl)quinolone;
4-((1S,4s)-4-((R)-1-(5,6-dichloro-1H-benzo[d]imidazol-2-yl)ethyl)cyclohexyl)-6-fluoroquinoline;
6-fluoro-4-((1S,4s)-4-((R)-1-(5-(trifluoromethyl)-1H-benzo[d]imidazol-2-yl)ethyl) cyclohexyl)quinolone;
4-((1S,4s)-4-((R)-1-(7-chloro-5-(trifluoromethyl)-1H-benzo[d]imidazol-2-yl)ethyl) cyclohexyl)-6-fluoroquinoline;
4-((1S,4s)-4-((R)-1-(5,7-bis(trifluoromethyl)-1H-benzo [d]imidazol-2-yl)ethyl) cyclohexyl)-6-fluoroquinoline;
6-fluoro-4-((1S,4s)-4-((R)-1-(5-(trifluoromethoxy)-1H-benzo[d]imidazol-2-yl)ethyl) cyclohexyl)quinolone;
2-((R)-1-((1s,4S)-4-(6-fluoroquinolin-4-yl)cyclohexyl) ethyl)-1H-benzo[d]imidazole-5-carbonitrile;
methyl 2-((R)-1-((1s,4S)-4-(6-fluoroquinolin-4-yl)cyclohexyl)ethyl)-1H-benzo [d]imidazole-5-carboxylate;
4-(((1s,4s)-4-(1-(6-chloro-1H-benzo[d]imidazol-2-yl) propyl)cyclohexyl)oxy)quinolone; or
4-(((1s,4s)-4-(1-(6-chloro-1H-benzo[d]imidazol-2-yl) propyl)cyclohexyl)oxy)quinolone;

or a pharmaceutically acceptable salt thereof, a stereoisomer thereof, a tautomer thereof, or a solvate thereof.

2. A pharmaceutical composition comprising a compound according to claim 1 and a pharmaceutically acceptable excipient.

3. The pharmaceutical composition of claim 2, further comprising ipilimumab, nivolumab, pembrolizumab or a combination thereof.

4. A method of treating cancer in a patient in need of such treatment comprising administering to the patient a therapeutically effective amount of a compound according to claim 1.

5. The method of claim 4, wherein the cancer is selected from brain cancers, skin cancers, bladder cancers, ovarian cancers, breast cancers, gastric cancers, pancreatic cancers, prostate cancers, colon cancers, blood cancers, lung cancers and bone cancers.

* * * * *

UNITED STATES PATENT AND TRADEMARK OFFICE
CERTIFICATE OF CORRECTION

PATENT NO. : 11,337,970 B2
APPLICATION NO. : 16/328449
DATED : May 24, 2022
INVENTOR(S) : Cherney et al.

It is certified that error appears in the above-identified patent and that said Letters Patent is hereby corrected as shown below:

On the Title Page

At Column 2, Line 3 (Other Publications), delete "phosphatidyleinositol" and insert therefor -- phosphatidylinositol --.

In the Claims

At Column 120, Line 38 (Claim 1), delete "cyclohexyl) quinolone;" and insert -- cyclohexyl)quinolone; --.

At Column 120, Line 40 (Claim 1), delete "[4',5':4,59 benzo" and insert -- [4',5':4,5]benzo --.

At Column 120, Line 51 (Claim 1), delete "benzo [d]" and insert -- benzo[d] --.

At Column 120, Line 55 (Claim 1), delete "[d] oxazol" and insert -- [d]oxazol --.

At Column 121, Line 7 (Claim 1), delete "cyclohexyl) oxy)" and insert -- cyclohexyl)oxy) --.

At Column 121, Line 13 (Claim 1), delete "1H -" and insert -- 1H- --.

At Column 121, Line 15 (Claim 1), delete "1H -" and insert -- 1H- --.

At Column 121, Line 17 (Claim 1), delete "ethyl) -" and insert -- ethyl)- --.

At Column 121, Line 34 (Claim 1), delete "trifluoropropyl) cyclohexyl)" and insert -- trifluoropropyl)cyclohexyl) --.

At Column 121, Line 41 (Claim 1), delete "propyl) -" and insert -- propyl)- --.

At Column 121, Line 44 (Claim 1), "naphthyridine" and insert -- naphthyridine; --.

Signed and Sealed this
Eleventh Day of October, 2022

Katherine Kelly Vidal
*Director of the United States Patent and Trademark Office*

CERTIFICATE OF CORRECTION (continued)
U.S. Pat. No. 11,337,970 B2

At Column 121, Line 46 (Claim 1), delete "ethyl) -" and insert -- ethyl)- --.

At Column 122, Line 2 (Claim 1), delete "benzo [d]" and insert -- benzo[d] --.

At Column 122, Line 10 (Claim 1), delete "ethyl) cyclohexyl)" and insert -- ethyl)cyclohexyl) --.

At Column 122, Line 14 (Claim 1), delete "ethyl) cyclohexyl)" and insert -- ethyl)cyclohexyl) --.

At Column 122, Line 16 (Claim 1), delete "ethyl) cyclohexyl)" and insert -- ethyl)cyclohexyl) --.

At Column 122, Line 18-19 (Claim 1), delete "benzo [d]" and insert -- benzo[d] --.

At Column 122, Line 19 (Claim 1), delete "ethyl) cyclohexyl)" and insert -- ethyl)cyclohexyl) --.

At Column 122, Line 21 (Claim 1), delete "ethyl) cyclohexyl)" and insert -- ethyl)cyclohexyl) --.

At Column 122, Line 25 (Claim 1), delete "benzo [d]" and insert -- benzo[d] --.